(12) United States Patent
Forehand et al.

(10) Patent No.: US 12,272,448 B1
(45) Date of Patent: *Apr. 8, 2025

(54) PREDICTIVE RESOURCE MANAGEMENT

(71) Applicant: C/HCA, Inc., Nashville, TN (US)

(72) Inventors: Tyler Forehand, Nashville, TN (US); Edmund Jackson, Nashville, TN (US); Nathan Watkins, Nashville, TN (US); J R Allen, Nashville, TN (US)

(73) Assignee: C/HCA, Inc., Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/415,505

(22) Filed: Jan. 17, 2024

Related U.S. Application Data

(63) Continuation of application No. 17/178,995, filed on Feb. 18, 2021, now Pat. No. 11,908,573.
(Continued)

(51) Int. Cl.
*G16H 40/20* (2018.01)

(52) U.S. Cl.
CPC .................................. *G16H 40/20* (2018.01)

(58) Field of Classification Search
CPC ......... G06Q 10/00–50/00; G16H 10/00–80/00
(Continued)

(56) References Cited

U.S. PATENT DOCUMENTS 5,497,141 A   3/1996   Coles et al.
5,508,912 A *   4/1996   Schneiderman ....... G16H 40/20
                                                             707/999.006
(Continued)

FOREIGN PATENT DOCUMENTS

WO        0154027 A1    7/2001
WO   2007059057 A2    5/2007
(Continued)

OTHER PUBLICATIONS

"About Crimson Continuum of Care", The Advisory Board Company, Available online At: http://www.advisory.com/technology/crimson-continuum-of-care/about-crimson-continuum-of-care, Jul. 7, 2014, 2 pages.
(Continued)

*Primary Examiner* — Alan S Miller
(74) *Attorney, Agent, or Firm* — Kory D. Christensen

(57) ABSTRACT

The techniques may include receiving patient data of patients of a service facility, each patient assigned to a service unit. In addition, the techniques may include inputting patient data into a classification model trained to output classifications. The techniques may include determining a classification for each patient. Moreover, the techniques may include assigning each patient to a patient group based at least in part on a classification common with members of the patient group. The techniques may include determining a recommendation associated with at least one of: (1) servicing a first service resource associated with a third service unit, or (2) procuring a second service resource associated with a fourth service unit. This recommendation can be based at least in part on the classifications. Further, the techniques may include presenting on a user device of a patient care provider for coordinating patient care among service units of the service facility.

20 Claims, 30 Drawing Sheets

Related U.S. Application Data

(60) Provisional application No. 62/978,155, filed on Feb. 18, 2020.

(58) Field of Classification Search
USPC .................. 370/200–916; 705/7.11–7.42
See application file for complete search history.

(56) References Cited

U.S. PATENT DOCUMENTS

| | | |
|---|---|---|
| 5,537,618 A | 7/1996 | Boulton et al. |
| 5,544,649 A | 8/1996 | David et al. |
| 5,584,024 A | 12/1996 | Shwartz |
| 5,735,285 A | 4/1998 | Albert et al. |
| 5,913,197 A | 6/1999 | Kameda |
| 5,937,387 A | 8/1999 | Summerell et al. |
| 5,991,728 A | 11/1999 | DeBusk et al. |
| 6,063,028 A * | 5/2000 | Luciano ............... G16H 50/50 600/300 |
| 6,117,073 A | 9/2000 | Jones et al. |
| 6,223,218 B1 | 4/2001 | Iijima et al. |
| 6,269,339 B1 | 7/2001 | Silver |
| 6,347,329 B1 | 2/2002 | Evans |
| 6,385,589 B1 | 5/2002 | Trusheim et al. |
| 6,629,937 B2 | 10/2003 | Watrous |
| 6,768,293 B2 | 7/2004 | Snaddon et al. |
| 6,824,052 B2 | 11/2004 | Walsh |
| 6,873,982 B1 | 3/2005 | Bates et al. |
| 6,934,292 B1 | 8/2005 | Ammitzboell |
| 6,937,150 B2 | 8/2005 | Medema et al. |
| 6,952,181 B2 | 10/2005 | Karr et al. |
| 6,976,013 B1 | 12/2005 | Mah |
| 6,978,263 B2 | 12/2005 | Soulanille |
| 7,013,326 B1 | 3/2006 | Suzuki et al. |
| 7,120,683 B2 | 10/2006 | Huang |
| 7,174,381 B2 | 2/2007 | Gulko et al. |
| 7,184,441 B1 | 2/2007 | Kadambi et al. |
| 7,237,205 B2 | 6/2007 | Sarel |
| 7,254,628 B2 | 8/2007 | Koops et al. |
| 7,263,551 B2 | 8/2007 | Belfiore et al. |
| 7,386,565 B1 | 6/2008 | Singh et al. |
| 7,509,263 B1 | 3/2009 | Fiedotin et al. |
| 7,519,826 B2 | 4/2009 | Carley |
| 7,570,989 B2 | 8/2009 | Baura et al. |
| 7,587,368 B2 | 9/2009 | Felsher |
| 7,603,413 B1 | 10/2009 | Herold et al. |
| 7,630,371 B2 | 12/2009 | Hernandez et al. |
| 7,630,986 B1 | 12/2009 | Herz et al. |
| 7,644,168 B2 | 1/2010 | Grieff et al. |
| 7,697,419 B1 | 4/2010 | Donthi |
| 7,707,289 B1 | 4/2010 | Skene et al. |
| 7,721,300 B2 | 5/2010 | Tipton et al. |
| 7,734,479 B2 | 6/2010 | Rosow et al. |
| 7,742,762 B1 | 6/2010 | Biere et al. |
| 7,743,303 B2 | 6/2010 | Nobunaga et al. |
| 7,757,268 B2 | 7/2010 | Gupta et al. |
| 7,769,600 B2 | 8/2010 | Iliff |
| 7,801,591 B1 | 9/2010 | Shusterman |
| 7,810,151 B1 | 10/2010 | Guruswamy |
| 7,835,923 B1 | 11/2010 | Rowley |
| 7,853,241 B1 | 12/2010 | Harrison |
| 7,890,349 B2 * | 2/2011 | Cole ............... G16H 40/20 705/3 |
| 8,005,692 B2 | 8/2011 | Karkanias et al. |
| 8,010,385 B1 | 8/2011 | Henderson |
| 8,042,158 B2 | 10/2011 | Larsen |
| 8,094,009 B2 | 1/2012 | Allen et al. |
| 8,165,893 B1 | 4/2012 | Goldberg et al. |
| 8,165,897 B2 | 4/2012 | Beraja et al. |
| 8,235,724 B2 | 8/2012 | Gilley et al. |
| 8,271,471 B1 | 9/2012 | Kamvar et al. |
| 8,291,468 B1 | 10/2012 | Chickering |
| 8,331,229 B1 | 12/2012 | Hu et al. |
| 8,452,630 B1 | 5/2013 | Fisher et al. |
| 8,475,370 B2 | 7/2013 | McCombie et al. |
| 8,550,996 B2 | 10/2013 | Parshuram et al. |
| 8,560,968 B1 | 10/2013 | Nair |
| 8,566,115 B2 | 10/2013 | Moore |
| 8,583,450 B2 | 11/2013 | Baker et al. |
| 8,594,776 B2 | 11/2013 | McCombie et al. |
| 8,595,792 B2 | 11/2013 | Azagury et al. |
| 8,600,777 B2 | 12/2013 | Schoenberg et al. |
| 8,600,895 B2 | 12/2013 | Felsher |
| 8,645,155 B2 | 2/2014 | Menon et al. |
| 8,660,857 B2 | 2/2014 | Ebadollahi et al. |
| 8,719,058 B2 | 5/2014 | Bonner et al. |
| 8,781,855 B2 | 7/2014 | Miller et al. |
| 8,825,786 B1 | 9/2014 | Webb, III et al. |
| 8,838,215 B2 | 9/2014 | John et al. |
| 8,868,616 B1 | 10/2014 | Otto et al. |
| 8,949,082 B2 | 2/2015 | Farooq et al. |
| 8,949,137 B2 | 2/2015 | Crapo et al. |
| 8,954,472 B1 | 2/2015 | Chapman et al. |
| 8,983,930 B2 | 3/2015 | Cheng et al. |
| 9,058,352 B2 | 6/2015 | Dudala |
| 9,060,266 B2 | 6/2015 | Kim et al. |
| 9,060,683 B2 | 6/2015 | Tran |
| 9,069,984 B2 | 6/2015 | Said et al. |
| 9,081,879 B2 | 7/2015 | Iliff |
| 9,100,483 B1 | 8/2015 | Snedden |
| 9,105,000 B1 | 8/2015 | White et al. |
| 9,158,932 B2 | 10/2015 | Ritter et al. |
| 9,201,985 B2 | 12/2015 | Elias et al. |
| 9,202,084 B2 | 12/2015 | Moore |
| 9,203,814 B2 | 12/2015 | Perez et al. |
| 9,244,978 B2 | 1/2016 | Alves et al. |
| 9,269,116 B2 | 2/2016 | Bulat |
| 9,281,993 B2 | 3/2016 | Kaminsky et al. |
| 9,391,973 B2 | 7/2016 | Fischer et al. |
| 9,396,232 B1 | 7/2016 | Kapoor et al. |
| 9,433,348 B2 | 9/2016 | Eshelman et al. |
| 9,454,577 B1 | 9/2016 | Kapoor et al. |
| 9,507,755 B1 | 11/2016 | Kerzner |
| 9,524,569 B2 | 12/2016 | Moore et al. |
| 9,525,606 B1 | 12/2016 | Staggs et al. |
| 9,542,530 B2 | 1/2017 | Nadarajah et al. |
| 9,560,119 B2 | 1/2017 | Udupi et al. |
| 9,576,263 B2 | 2/2017 | Beck et al. |
| 9,613,190 B2 | 4/2017 | Ford et al. |
| 9,690,538 B1 | 6/2017 | Doyle, III et al. |
| 9,710,600 B1 | 7/2017 | Dunleavy et al. |
| 9,715,835 B2 | 7/2017 | Mason et al. |
| 9,734,289 B2 | 8/2017 | Pecora |
| 9,734,298 B2 | 8/2017 | Hall et al. |
| 9,740,823 B2 | 8/2017 | Breazeale, Jr. |
| 9,754,335 B2 | 9/2017 | Jourdan et al. |
| 9,762,553 B2 | 9/2017 | Ford et al. |
| 9,779,407 B2 | 10/2017 | Adjaoute |
| 9,779,611 B1 | 10/2017 | Krayer et al. |
| 9,787,685 B2 | 10/2017 | Zhang et al. |
| 9,805,163 B1 | 10/2017 | Panch et al. |
| 9,811,438 B1 | 11/2017 | Barrett et al. |
| 9,847,911 B1 | 12/2017 | Gigandet et al. |
| 9,880,881 B1 | 1/2018 | Perez et al. |
| 9,892,380 B2 | 2/2018 | Naghshin et al. |
| 9,905,112 B1 | 2/2018 | Krayer et al. |
| 9,906,532 B2 | 2/2018 | Perez et al. |
| 9,973,455 B1 | 5/2018 | Fowler et al. |
| 9,979,780 B1 | 5/2018 | Faibish et al. |
| 10,027,653 B2 | 7/2018 | Kim |
| 10,033,702 B2 | 7/2018 | Ford et al. |
| 10,055,547 B2 | 8/2018 | Chari et al. |
| 10,095,471 B2 | 10/2018 | Dwivedi et al. |
| 10,121,389 B1 | 11/2018 | Mason et al. |
| 10,140,288 B2 | 11/2018 | Pestian et al. |
| 10,140,421 B1 | 11/2018 | Bernard et al. |
| 10,185,929 B2 | 1/2019 | Kharraz Tavakol et al. |
| 10,231,085 B1 | 3/2019 | Kumar et al. |
| 10,263,945 B1 | 4/2019 | Linkous et al. |
| 10,296,187 B1 | 5/2019 | Gregg et al. |
| 10,303,519 B1 | 5/2019 | Perez et al. |
| 10,311,442 B1 | 6/2019 | Lancaster |
| 10,311,701 B1 | 6/2019 | Krayer et al. |
| 10,319,056 B1 | 6/2019 | Perez et al. |
| 10,324,947 B2 | 6/2019 | Dey et al. |

(56) References Cited

U.S. PATENT DOCUMENTS

| | | |
|---|---|---|
| 10,325,070 B2 | 6/2019 | Beale et al. |
| 10,373,268 B1 | 8/2019 | Orphys et al. |
| 10,379,987 B1 | 8/2019 | Chari et al. |
| 10,380,181 B1 | 8/2019 | Morrow et al. |
| 10,412,028 B1 | 9/2019 | Gregg et al. |
| 10,425,355 B1 | 9/2019 | Manoukian et al. |
| 10,469,306 B1 | 11/2019 | Boles et al. |
| 10,505,935 B1 | 12/2019 | Perez et al. |
| 10,542,004 B1 | 1/2020 | Perez et al. |
| 10,594,578 B1 | 3/2020 | Staggs et al. |
| 10,628,180 B1 | 4/2020 | Swanger et al. |
| 10,642,958 B1 | 5/2020 | Perlin et al. |
| 10,652,164 B2 | 5/2020 | Garcia et al. |
| 10,665,348 B1 | 5/2020 | Krayer et al. |
| 10,672,251 B1 | 6/2020 | Krayer et al. |
| 10,795,795 B1 | 10/2020 | Chari et al. |
| 10,797,987 B1 | 10/2020 | Beacham |
| 10,812,426 B1 | 10/2020 | Gregg et al. |
| 10,817,342 B1 | 10/2020 | Perez et al. |
| 10,847,261 B1 | 11/2020 | Neumann |
| 10,862,921 B2 | 12/2020 | Ahad et al. |
| 10,931,509 B1 | 2/2021 | Boles et al. |
| 11,029,913 B1 | 6/2021 | Doyle, III et al. |
| 11,126,445 B1 | 9/2021 | Swanger et al. |
| 11,146,599 B1 | 10/2021 | Jackson et al. |
| 11,178,027 B1 | 11/2021 | Staggs et al. |
| 11,201,835 B1 | 12/2021 | Roberts et al. |
| 11,237,937 B1 | 2/2022 | Chari et al. |
| 11,276,293 B1 | 3/2022 | Krayer et al. |
| 11,283,690 B1 | 3/2022 | Mosier et al. |
| 11,283,726 B1 | 3/2022 | Houston et al. |
| 11,317,292 B1 | 4/2022 | Feldmann et al. |
| 11,347,789 B1 | 5/2022 | Morrow et al. |
| 11,374,847 B1 | 6/2022 | Beacham |
| 11,381,506 B1 | 7/2022 | Jindal et al. |
| 11,422,830 B1 | 8/2022 | Hefley |
| 11,431,595 B1 | 8/2022 | Staggs et al. |
| 11,451,622 B1 | 9/2022 | Perez et al. |
| 11,462,322 B1 | 10/2022 | Cuthbert et al. |
| 11,539,817 B1 | 12/2022 | Perez |
| 11,595,320 B1 | 2/2023 | Gregg et al. |
| 11,736,412 B1 | 8/2023 | Roberts et al. |
| 11,836,664 B2 | 12/2023 | Ackerman et al. |
| 11,908,573 B1 | 2/2024 | Forehand et al. |
| 2001/0042119 A1 | 11/2001 | Urano et al. |
| 2001/0051765 A1 | 12/2001 | Walker et al. |
| 2002/0007285 A1 | 1/2002 | Rappaport |
| 2002/0016719 A1 | 2/2002 | Nemeth et al. |
| 2002/0032583 A1 | 3/2002 | Joao |
| 2002/0065685 A1 | 5/2002 | Sasaki et al. |
| 2002/0077865 A1 | 6/2002 | Sullivan |
| 2002/0116453 A1 | 8/2002 | Todorov et al. |
| 2002/0128925 A1 | 9/2002 | Angeles |
| 2002/0178074 A1 | 11/2002 | Bloom |
| 2002/0178246 A1 | 11/2002 | Mayer |
| 2002/0193667 A1 | 12/2002 | McNair |
| 2003/0083903 A1 | 5/2003 | Myers |
| 2003/0105638 A1 | 6/2003 | Taira |
| 2003/0125609 A1 | 7/2003 | Becker |
| 2003/0154270 A1 | 8/2003 | Aranda, Jr. |
| 2003/0206116 A1 | 11/2003 | Weiner et al. |
| 2003/0215092 A1 | 11/2003 | Dick |
| 2003/0229645 A1 | 12/2003 | Mogi et al. |
| 2004/0006492 A1 | 1/2004 | Watanabe |
| 2004/0122702 A1* | 6/2004 | Sabol .................. G06Q 10/10 706/45 |
| 2004/0143458 A1 | 7/2004 | Pulkkinen et al. |
| 2004/0172222 A1 | 9/2004 | Simpson et al. |
| 2004/0243444 A1 | 12/2004 | Steusloff et al. |
| 2004/0247748 A1 | 12/2004 | Bronkema |
| 2004/0249674 A1 | 12/2004 | Eisenberg et al. |
| 2004/0249878 A1 | 12/2004 | Luick |
| 2004/0252870 A1 | 12/2004 | Reeves et al. |
| 2004/0254763 A1 | 12/2004 | Sakai et al. |
| 2004/0267570 A1 | 12/2004 | Becker |
| 2004/0267735 A1 | 12/2004 | Melham |
| 2005/0020903 A1 | 1/2005 | Krishnan et al. |
| 2005/0063365 A1 | 3/2005 | Mathew et al. |
| 2005/0067493 A1 | 3/2005 | Urken |
| 2005/0075902 A1* | 4/2005 | Wager .................. G16H 40/20 705/2 |
| 2005/0075970 A1 | 4/2005 | Doyle |
| 2005/0076110 A1 | 4/2005 | Mathew et al. |
| 2005/0113721 A1 | 5/2005 | Reed et al. |
| 2005/0137925 A1 | 6/2005 | Lakritz et al. |
| 2005/0144042 A1 | 6/2005 | Joffe et al. |
| 2005/0151640 A1 | 7/2005 | Hastings |
| 2005/0228691 A1 | 10/2005 | Paparo |
| 2005/0242928 A1 | 11/2005 | Kirkeby |
| 2005/0245249 A1 | 11/2005 | Wierman et al. |
| 2005/0288965 A1 | 12/2005 | Van Eaton et al. |
| 2006/0004745 A1 | 1/2006 | Kuhn et al. |
| 2006/0036729 A1 | 2/2006 | Sakaguchi et al. |
| 2006/0047552 A1 | 3/2006 | Larsen et al. |
| 2006/0047554 A1 | 3/2006 | Larsen et al. |
| 2006/0047704 A1 | 3/2006 | Gopalakrishnan |
| 2006/0067343 A1 | 3/2006 | Tagawa et al. |
| 2006/0100899 A1 | 5/2006 | Tajima |
| 2006/0111941 A1 | 5/2006 | Blom |
| 2006/0112050 A1 | 5/2006 | Miikkulainen et al. |
| 2006/0112247 A1 | 5/2006 | Ramany et al. |
| 2006/0129345 A1 | 6/2006 | Parvin et al. |
| 2006/0135855 A1 | 6/2006 | Alsafadi et al. |
| 2006/0136267 A1 | 6/2006 | Brackett et al. |
| 2006/0154642 A1 | 7/2006 | Scannell, Jr. |
| 2006/0168170 A1 | 7/2006 | Korzeniowski |
| 2006/0173708 A1 | 8/2006 | Vining et al. |
| 2006/0182324 A1 | 8/2006 | Motoki |
| 2006/0239219 A1 | 10/2006 | Haffner et al. |
| 2006/0240771 A1 | 10/2006 | Graves et al. |
| 2006/0241978 A1 | 10/2006 | Yoshii |
| 2006/0271409 A1 | 11/2006 | Rosenfeld et al. |
| 2006/0280181 A1 | 12/2006 | Brailas et al. |
| 2006/0282302 A1 | 12/2006 | Hussain |
| 2007/0005257 A1* | 1/2007 | Cheng .................. G06F 18/29 702/19 |
| 2007/0035403 A1 | 2/2007 | Krishna et al. |
| 2007/0067185 A1 | 3/2007 | Halsted |
| 2007/0094046 A1 | 4/2007 | Cobbs et al. |
| 2007/0129983 A1 | 6/2007 | Scherpbier et al. |
| 2007/0136743 A1 | 6/2007 | Hasek et al. |
| 2007/0143149 A1 | 6/2007 | Buttner et al. |
| 2007/0150314 A1 | 6/2007 | Abraham-Fuchs et al. |
| 2007/0179351 A1 | 8/2007 | Kil et al. |
| 2007/0185390 A1 | 8/2007 | Perkins et al. |
| 2007/0191688 A1 | 8/2007 | Lynn |
| 2007/0213599 A1 | 9/2007 | Siejko et al. |
| 2007/0230486 A1 | 10/2007 | Zafirov |
| 2007/0239484 A1 | 10/2007 | Arond et al. |
| 2007/0239490 A1 | 10/2007 | Sullivan |
| 2007/0250345 A1 | 10/2007 | Walker et al. |
| 2007/0258106 A1 | 11/2007 | Ishiyama et al. |
| 2007/0270671 A1 | 11/2007 | Gal |
| 2008/0021738 A1 | 1/2008 | Komiya et al. |
| 2008/0040160 A1 | 2/2008 | Scherpbier et al. |
| 2008/0058773 A1 | 3/2008 | John |
| 2008/0065580 A1 | 3/2008 | Spence et al. |
| 2008/0076637 A1 | 3/2008 | Gilley et al. |
| 2008/0091464 A1 | 4/2008 | Lipscher et al. |
| 2008/0094207 A1 | 4/2008 | Collins, Jr. et al. |
| 2008/0097792 A1 | 4/2008 | Marge |
| 2008/0147829 A1 | 6/2008 | Chang |
| 2008/0154691 A1 | 6/2008 | Wellman et al. |
| 2008/0154712 A1 | 6/2008 | Wellman |
| 2008/0155386 A1 | 6/2008 | Jensen |
| 2008/0162496 A1 | 7/2008 | Postrel |
| 2008/0164998 A1 | 7/2008 | Scherpbier et al. |
| 2008/0227063 A1 | 9/2008 | Kenedy et al. |
| 2008/0248781 A1 | 10/2008 | Cedo Perpinya et al. |
| 2008/0255880 A1 | 10/2008 | Beller et al. |
| 2008/0262869 A1 | 10/2008 | Bronn |
| 2008/0262883 A1 | 10/2008 | Weiss et al. |
| 2008/0269625 A1 | 10/2008 | Halperin et al. |
| 2008/0270189 A1 | 10/2008 | Howard |

(56) References Cited

U.S. PATENT DOCUMENTS

| | | |
|---|---|---|
| 2008/0294507 A1 | 11/2008 | Reiner |
| 2008/0312959 A1 | 12/2008 | Rose et al. |
| 2008/0319271 A1 | 12/2008 | Barnowski et al. |
| 2009/0006125 A1 | 1/2009 | Angell et al. |
| 2009/0027337 A1 | 1/2009 | Hildreth |
| 2009/0037224 A1 | 2/2009 | Raduchel |
| 2009/0037225 A1 | 2/2009 | Burchianti et al. |
| 2009/0043634 A1 | 2/2009 | Tisdale |
| 2009/0058635 A1 | 3/2009 | LaLonde et al. |
| 2009/0063187 A1 | 3/2009 | Johnson et al. |
| 2009/0089092 A1 | 4/2009 | Johnson et al. |
| 2009/0097623 A1 | 4/2009 | Bharadwaj |
| 2009/0099862 A1 | 4/2009 | Fireman et al. |
| 2009/0106225 A1 | 4/2009 | Smith et al. |
| 2009/0113560 A1 | 4/2009 | Kori et al. |
| 2009/0125332 A1 | 5/2009 | Martin |
| 2009/0125334 A1 | 5/2009 | Krishnan et al. |
| 2009/0125348 A1 | 5/2009 | Rastogi |
| 2009/0146822 A1 | 6/2009 | Soliman et al. |
| 2009/0154667 A1 | 6/2009 | Hao et al. |
| 2009/0164236 A1 | 6/2009 | Gounares et al. |
| 2009/0198733 A1 | 8/2009 | Gounares et al. |
| 2009/0204436 A1 | 8/2009 | Thorne et al. |
| 2009/0216558 A1 | 8/2009 | Reisman et al. |
| 2009/0228304 A1 | 9/2009 | Ciarniello et al. |
| 2009/0248828 A1 | 10/2009 | Gould et al. |
| 2009/0259495 A1 | 10/2009 | Rosenfeld |
| 2009/0274286 A1 | 11/2009 | O'Shaughnessy et al. |
| 2009/0275805 A1 | 11/2009 | Lane et al. |
| 2009/0299766 A1 | 12/2009 | Friedlander et al. |
| 2009/0322513 A1 | 12/2009 | Hwang et al. |
| 2009/0327689 A1 | 12/2009 | Lazar |
| 2010/0004948 A1 | 1/2010 | Toomey et al. |
| 2010/0025071 A1 | 2/2010 | Jeroense et al. |
| 2010/0036676 A1 | 2/2010 | Safdi et al. |
| 2010/0036903 A1 | 2/2010 | Ahmad et al. |
| 2010/0070295 A1 | 3/2010 | Kharraz Tavakol et al. |
| 2010/0082363 A1 | 4/2010 | Warner et al. |
| 2010/0082371 A1 | 4/2010 | Kamp et al. |
| 2010/0094648 A1 | 4/2010 | Seward |
| 2010/0094649 A1 | 4/2010 | White |
| 2010/0121654 A1 | 5/2010 | Portnoy et al. |
| 2010/0161353 A1 | 6/2010 | Mayaud |
| 2010/0169142 A1 | 7/2010 | Hinton et al. |
| 2010/0169424 A1 | 7/2010 | Gustafsson et al. |
| 2010/0169503 A1 | 7/2010 | Kollmansberger et al. |
| 2010/0198755 A1 | 8/2010 | Soll et al. |
| 2010/0217738 A1 | 8/2010 | Sarel |
| 2010/0217886 A1 | 8/2010 | Seren et al. |
| 2010/0222649 A1 | 9/2010 | Schoenberg |
| 2010/0235187 A1 | 9/2010 | Firminger et al. |
| 2010/0250271 A1 | 9/2010 | Pearce et al. |
| 2010/0250285 A1 | 9/2010 | Shelton |
| 2010/0268040 A1 | 10/2010 | Ben-Oren et al. |
| 2010/0292544 A1 | 11/2010 | Sherman et al. |
| 2010/0295685 A1 | 11/2010 | Parvin et al. |
| 2010/0298661 A1 | 11/2010 | McCombie et al. |
| 2010/0305966 A1 | 12/2010 | Coulter et al. |
| 2010/0332583 A1 | 12/2010 | Szabo |
| 2011/0001605 A1 | 1/2011 | Kiani et al. |
| 2011/0004491 A1 | 1/2011 | Sameh et al. |
| 2011/0046979 A1 | 2/2011 | Tulipano et al. |
| 2011/0054934 A1 | 3/2011 | Vesto et al. |
| 2011/0054946 A1 | 3/2011 | Coulter et al. |
| 2011/0060229 A1 | 3/2011 | Hulvershorn et al. |
| 2011/0105854 A1 | 5/2011 | Kiani et al. |
| 2011/0119088 A1 | 5/2011 | Gunn |
| 2011/0129131 A1 | 6/2011 | Avinash et al. |
| 2011/0153344 A1 | 6/2011 | Vesto |
| 2011/0161095 A1 | 6/2011 | Line et al. |
| 2011/0172550 A1 | 7/2011 | Martin et al. |
| 2011/0199214 A1* | 8/2011 | Gawlick ............... G16H 50/20 |
| | | 340/573.1 |
| 2011/0225114 A1 | 9/2011 | Gotthardt |
| 2011/0246220 A1 | 10/2011 | Albert |
| 2011/0286357 A1 | 11/2011 | Haris et al. |
| 2011/0288877 A1 | 11/2011 | Ofek et al. |
| 2011/0291837 A1 | 12/2011 | Rantala |
| 2011/0295078 A1 | 12/2011 | Reid et al. |
| 2011/0295621 A1* | 12/2011 | Farooq ............... G16H 50/20 |
| | | 705/3 |
| 2011/0295961 A1 | 12/2011 | Wilkes et al. |
| 2011/0313788 A1 | 12/2011 | Amland et al. |
| 2011/0320221 A1 | 12/2011 | Duffey-Rosenstein et al. |
| 2012/0004924 A1 | 1/2012 | Kachnowski et al. |
| 2012/0004925 A1 | 1/2012 | Braverman et al. |
| 2012/0011125 A1 | 1/2012 | Bousamra et al. |
| 2012/0035959 A1 | 2/2012 | Berdia |
| 2012/0047105 A1 | 2/2012 | Saigal et al. |
| 2012/0064006 A1 | 3/2012 | Yadav |
| 2012/0065987 A1 | 3/2012 | Farooq et al. |
| 2012/0078656 A1 | 3/2012 | Wennberg et al. |
| 2012/0089481 A1 | 4/2012 | Iozzia et al. |
| 2012/0095300 A1 | 4/2012 | McNair |
| 2012/0096065 A1 | 4/2012 | Suit et al. |
| 2012/0101847 A1 | 4/2012 | Johnson et al. |
| 2012/0109683 A1 | 5/2012 | Ebadollahi et al. |
| 2012/0112906 A1 | 5/2012 | Borke et al. |
| 2012/0117268 A1 | 5/2012 | Shaffer et al. |
| 2012/0117476 A1 | 5/2012 | Siegrist et al. |
| 2012/0124146 A1 | 5/2012 | Hsiao et al. |
| 2012/0130734 A1 | 5/2012 | White |
| 2012/0150252 A1 | 6/2012 | Feldman et al. |
| 2012/0157795 A1 | 6/2012 | Chiu et al. |
| 2012/0165620 A1 | 6/2012 | Tanis et al. |
| 2012/0180122 A1 | 7/2012 | Yan et al. |
| 2012/0182924 A1 | 7/2012 | Gaines et al. |
| 2012/0185267 A1 | 7/2012 | Kamen et al. |
| 2012/0209625 A1 | 8/2012 | Armstrong et al. |
| 2012/0215555 A1 | 8/2012 | Sharma et al. |
| 2012/0215560 A1 | 8/2012 | Ofek et al. |
| 2012/0215562 A1 | 8/2012 | James et al. |
| 2012/0224057 A1 | 9/2012 | Gill et al. |
| 2012/0226796 A1 | 9/2012 | Morgan |
| 2012/0232416 A1 | 9/2012 | Gilham et al. |
| 2012/0239671 A1 | 9/2012 | Chaudhri et al. |
| 2012/0265029 A1 | 10/2012 | Fahey |
| 2012/0286953 A1 | 11/2012 | Bousamra et al. |
| 2012/0303827 A1 | 11/2012 | Neystadt et al. |
| 2012/0316911 A1 | 12/2012 | Schwarz |
| 2012/0330683 A1 | 12/2012 | Ledwidge et al. |
| 2013/0017780 A1 | 1/2013 | Rose et al. |
| 2013/0024382 A1 | 1/2013 | Dala et al. |
| 2013/0041686 A1 | 2/2013 | Prywes |
| 2013/0045685 A1 | 2/2013 | Kiani |
| 2013/0054265 A1 | 2/2013 | Warner et al. |
| 2013/0054467 A1 | 2/2013 | Dala et al. |
| 2013/0060167 A1 | 3/2013 | Dracup et al. |
| 2013/0080903 A1 | 3/2013 | Barda et al. |
| 2013/0093829 A1 | 4/2013 | Rosenblatt et al. |
| 2013/0096649 A1 | 4/2013 | Martin et al. |
| 2013/0097093 A1 | 4/2013 | Kolber et al. |
| 2013/0124965 A1 | 5/2013 | Elias et al. |
| 2013/0144641 A1 | 6/2013 | Bessette |
| 2013/0150686 A1 | 6/2013 | Fronterhouse et al. |
| 2013/0151563 A1 | 6/2013 | Addepalli et al. |
| 2013/0166317 A1 | 6/2013 | Beardall et al. |
| 2013/0173305 A1 | 7/2013 | Hyde et al. |
| 2013/0179178 A1 | 7/2013 | Vemireddy et al. |
| 2013/0191158 A1 | 7/2013 | Fillmore |
| 2013/0204637 A1 | 8/2013 | Vanderveen et al. |
| 2013/0216989 A1 | 8/2013 | Cuthbert |
| 2013/0218588 A1 | 8/2013 | Kehr et al. |
| 2013/0218599 A1 | 8/2013 | Highley |
| 2013/0231947 A1 | 9/2013 | Shusterman |
| 2013/0231956 A1 | 9/2013 | Chaudhri et al. |
| 2013/0262135 A1 | 10/2013 | Nichols et al. |
| 2013/0268226 A1 | 10/2013 | Morfino et al. |
| 2013/0278414 A1 | 10/2013 | Sprigg et al. |
| 2013/0279497 A1 | 10/2013 | Verma et al. |
| 2013/0289424 A1 | 10/2013 | Brockway et al. |
| 2013/0297348 A1 | 11/2013 | Cardoza et al. |
| 2013/0304499 A1 | 11/2013 | Rangadass |
| 2013/0326055 A1 | 12/2013 | Chatterjee et al. |

(56) References Cited

U.S. PATENT DOCUMENTS

| | | |
|---|---|---|
| 2013/0332240 A1 | 12/2013 | Patri et al. |
| 2014/0012509 A1 | 1/2014 | Barber |
| 2014/0012843 A1 | 1/2014 | Soon-Shiong |
| 2014/0019157 A1 | 1/2014 | Nudd et al. |
| 2014/0022080 A1 | 1/2014 | Mayoras, Jr. |
| 2014/0025394 A1 | 1/2014 | Aoki et al. |
| 2014/0025809 A1 | 1/2014 | Steuperaert |
| 2014/0045156 A1 | 2/2014 | Alessandri et al. |
| 2014/0046940 A1 | 2/2014 | Thomson et al. |
| 2014/0058755 A1 | 2/2014 | Macoviak et al. |
| 2014/0067418 A1 | 3/2014 | Hyzy |
| 2014/0067427 A1 | 3/2014 | Demopulos |
| 2014/0068728 A1 | 3/2014 | Kim et al. |
| 2014/0074509 A1 | 3/2014 | Amarasingham et al. |
| 2014/0081667 A1 | 3/2014 | Joao |
| 2014/0085078 A1 | 3/2014 | Carnes |
| 2014/0085080 A1 | 3/2014 | Carnes |
| 2014/0108033 A1* | 4/2014 | Akbay .................... G16Z 99/00 705/2 |
| 2014/0108034 A1* | 4/2014 | Akbay ............. G06Q 10/06315 705/2 |
| 2014/0108035 A1 | 4/2014 | Akbay et al. |
| 2014/0135588 A1 | 5/2014 | Al-Ali et al. |
| 2014/0136223 A1 | 5/2014 | Phillips |
| 2014/0156225 A1 | 6/2014 | Dagnino et al. |
| 2014/0164005 A1 | 6/2014 | Merkin |
| 2014/0172459 A1* | 6/2014 | De Vries ................ G16H 10/60 705/3 |
| 2014/0180711 A1 | 6/2014 | Kamen et al. |
| 2014/0188895 A1 | 7/2014 | Wang et al. |
| 2014/0201315 A1 | 7/2014 | Jacob et al. |
| 2014/0222451 A1 | 8/2014 | Hall et al. |
| 2014/0223480 A1 | 8/2014 | Berry et al. |
| 2014/0226466 A1 | 8/2014 | Pettersson et al. |
| 2014/0228982 A1 | 8/2014 | Bharwani |
| 2014/0229955 A1 | 8/2014 | Holmes et al. |
| 2014/0249878 A1 | 9/2014 | Kaufman |
| 2014/0276552 A1 | 9/2014 | Nguyen, Jr. et al. |
| 2014/0278463 A1 | 9/2014 | Merry et al. |
| 2014/0278496 A1 | 9/2014 | Spencer |
| 2014/0279227 A1 | 9/2014 | Schoenberg |
| 2014/0279948 A1 | 9/2014 | Mahate et al. |
| 2014/0280678 A1 | 9/2014 | Nixon et al. |
| 2014/0282257 A1 | 9/2014 | Nixon et al. |
| 2014/0297301 A1* | 10/2014 | Rock .................... G06Q 10/103 705/2 |
| 2014/0304545 A1 | 10/2014 | Chen et al. |
| 2014/0306826 A1 | 10/2014 | Ricci |
| 2014/0316797 A1 | 10/2014 | Biernacki et al. |
| 2014/0316813 A1 | 10/2014 | Bauer |
| 2014/0350565 A1 | 11/2014 | Yacoby et al. |
| 2014/0350967 A1 | 11/2014 | Geleijnse et al. |
| 2014/0357312 A1 | 12/2014 | Davis et al. |
| 2014/0362709 A1 | 12/2014 | Kashyap et al. |
| 2014/0365264 A1 | 12/2014 | Smiley et al. |
| 2014/0372138 A1 | 12/2014 | Chari et al. |
| 2014/0372522 A1 | 12/2014 | Orona et al. |
| 2014/0379273 A1 | 12/2014 | Petisce et al. |
| 2014/0379851 A1 | 12/2014 | LeCroy et al. |
| 2015/0006192 A1 | 1/2015 | Sudharsan et al. |
| 2015/0026708 A1 | 1/2015 | Ahmed et al. |
| 2015/0034123 A1 | 2/2015 | Pressacco et al. |
| 2015/0047046 A1 | 2/2015 | Pavlyushchik |
| 2015/0052160 A1 | 2/2015 | Hussam |
| 2015/0052247 A1 | 2/2015 | Threefoot et al. |
| 2015/0054947 A1 | 2/2015 | Dawes |
| 2015/0066529 A1 | 3/2015 | Lattuca et al. |
| 2015/0070187 A1 | 3/2015 | Wiesner et al. |
| 2015/0082219 A1 | 3/2015 | Beck et al. |
| 2015/0089373 A1 | 3/2015 | Dwivedi et al. |
| 2015/0097701 A1 | 4/2015 | Al-Ali et al. |
| 2015/0099458 A1 | 4/2015 | Weisner et al. |
| 2015/0100943 A1 | 4/2015 | Gabel et al. |
| 2015/0106125 A1 | 4/2015 | Farooq et al. |
| 2015/0111187 A1 | 4/2015 | Loeb, Jr. et al. |
| 2015/0112696 A1 | 4/2015 | Kharraz Tavakol |
| 2015/0141771 A1 | 5/2015 | Inbar |
| 2015/0149560 A1 | 5/2015 | Lee |
| 2015/0154528 A1 | 6/2015 | Kharraz Tavakol |
| 2015/0163121 A1 | 6/2015 | Mahaffey et al. |
| 2015/0164437 A1 | 6/2015 | McCombie et al. |
| 2015/0193583 A1 | 7/2015 | McNair et al. |
| 2015/0213202 A1 | 7/2015 | Amarasingham et al. |
| 2015/0213206 A1 | 7/2015 | Amarasingham et al. |
| 2015/0213207 A1 | 7/2015 | Amarasingham et al. |
| 2015/0213217 A1 | 7/2015 | Amarasingham et al. |
| 2015/0213222 A1 | 7/2015 | Amarasingham et al. |
| 2015/0213223 A1 | 7/2015 | Amarasingham et al. |
| 2015/0213224 A1 | 7/2015 | Amarasingham et al. |
| 2015/0213225 A1 | 7/2015 | Amarasingham et al. |
| 2015/0219530 A1 | 8/2015 | Li et al. |
| 2015/0227714 A1 | 8/2015 | Hayakawa |
| 2015/0238270 A1 | 8/2015 | Raffy et al. |
| 2015/0244687 A1 | 8/2015 | Perez et al. |
| 2015/0257646 A1 | 9/2015 | Groeschke et al. |
| 2015/0269433 A1 | 9/2015 | Amtrup et al. |
| 2015/0279335 A1 | 10/2015 | Ripp et al. |
| 2015/0312127 A1 | 10/2015 | Leemet et al. |
| 2015/0335288 A1 | 11/2015 | Toth et al. |
| 2015/0339442 A1 | 11/2015 | Oleynik |
| 2015/0341231 A1 | 11/2015 | Khan |
| 2015/0347704 A1 | 12/2015 | Baronov et al. |
| 2015/0378528 A1 | 12/2015 | Ramanathan et al. |
| 2016/0000483 A1 | 1/2016 | Stone |
| 2016/0004831 A1 | 1/2016 | Carlson et al. |
| 2016/0013990 A1 | 1/2016 | Kulkarni et al. |
| 2016/0026762 A1 | 1/2016 | Radhakrishnan et al. |
| 2016/0027278 A1 | 1/2016 | Mcintosh et al. |
| 2016/0027289 A1 | 1/2016 | Hargis |
| 2016/0034986 A1 | 2/2016 | Ortiz |
| 2016/0042049 A1 | 2/2016 | Shilts et al. |
| 2016/0042135 A1* | 2/2016 | Hogan .................... G16Z 99/00 705/2 |
| 2016/0045167 A1 | 2/2016 | Gheeraert et al. |
| 2016/0058286 A1 | 3/2016 | Joshua et al. |
| 2016/0065629 A1 | 3/2016 | Emoff |
| 2016/0085914 A1 | 3/2016 | Douglass et al. |
| 2016/0086136 A1 | 3/2016 | Pidara et al. |
| 2016/0094410 A1 | 3/2016 | Anwar et al. |
| 2016/0098525 A1 | 4/2016 | Maheshwari et al. |
| 2016/0098542 A1 | 4/2016 | Costantini et al. |
| 2016/0105316 A1 | 4/2016 | Guntaka et al. |
| 2016/0110502 A1 | 4/2016 | Bronson et al. |
| 2016/0125168 A1* | 5/2016 | Aagesen ................ G16H 10/60 705/3 |
| 2016/0125680 A1 | 5/2016 | White et al. |
| 2016/0132372 A1 | 5/2016 | Anderson et al. |
| 2016/0139782 A1 | 5/2016 | Scott et al. |
| 2016/0157113 A1 | 6/2016 | Row, II et al. |
| 2016/0162532 A1 | 6/2016 | Zhang et al. |
| 2016/0171452 A1 | 6/2016 | Brown |
| 2016/0174913 A1 | 6/2016 | Somanath et al. |
| 2016/0182614 A1 | 6/2016 | Udupi et al. |
| 2016/0188799 A1 | 6/2016 | Borras |
| 2016/0188832 A1 | 6/2016 | Kramer |
| 2016/0191314 A1 | 6/2016 | Russell et al. |
| 2016/0218918 A1 | 7/2016 | Chu et al. |
| 2016/0239614 A1 | 8/2016 | Siva |
| 2016/0246941 A1 | 8/2016 | Miller et al. |
| 2016/0248926 A1 | 8/2016 | Yasuda |
| 2016/0254964 A1 | 9/2016 | Benc |
| 2016/0277255 A1 | 9/2016 | Dasgupta et al. |
| 2016/0301577 A1 | 10/2016 | Lane |
| 2016/0321406 A1 | 11/2016 | Timmerman et al. |
| 2016/0321430 A1 | 11/2016 | Eckman et al. |
| 2016/0342753 A1 | 11/2016 | Feazell |
| 2016/0360466 A1 | 12/2016 | Barak et al. |
| 2016/0366468 A1 | 12/2016 | Seo |
| 2017/0017761 A1 | 1/2017 | Tsugo |
| 2017/0019264 A1 | 1/2017 | Nugent et al. |
| 2017/0048110 A1 | 2/2017 | Wu et al. |
| 2017/0054758 A1 | 2/2017 | Maino et al. |
| 2017/0063826 A1 | 3/2017 | Sundaresan et al. |
| 2017/0068792 A1 | 3/2017 | Reiner |

(56) References Cited

U.S. PATENT DOCUMENTS

| | | | |
|---|---|---|---|
| 2017/0083626 A1 | 3/2017 | Kensel et al. | |
| 2017/0085447 A1 | 3/2017 | Chen et al. | |
| 2017/0103181 A1 | 4/2017 | Czerska | |
| 2017/0109479 A1 | 4/2017 | Vemireddy et al. | |
| 2017/0116373 A1 | 4/2017 | Ginsburg et al. | |
| 2017/0161433 A1 | 6/2017 | Perretta | |
| 2017/0169173 A1* | 6/2017 | Snow, Jr. | G16H 40/20 |
| 2017/0187577 A1 | 6/2017 | Nevrekar et al. | |
| 2017/0236281 A1 | 8/2017 | Dacosta | |
| 2017/0277829 A1 | 9/2017 | Weggler et al. | |
| 2017/0293988 A1 | 10/2017 | Goyal | |
| 2017/0308648 A1 | 10/2017 | Clarke et al. | |
| 2017/0308649 A1 | 10/2017 | Lodhia et al. | |
| 2017/0310605 A1 | 10/2017 | Garcia et al. | |
| 2017/0323064 A1 | 11/2017 | Bates | |
| 2017/0364043 A1 | 12/2017 | Ganti et al. | |
| 2017/0366558 A1 | 12/2017 | Liu | |
| 2017/0372443 A1* | 12/2017 | Katsuda | G16H 50/20 |
| 2018/0075108 A1 | 3/2018 | Park et al. | |
| 2018/0107879 A1 | 4/2018 | Laput et al. | |
| 2018/0122499 A1 | 5/2018 | Austin et al. | |
| 2018/0152411 A1 | 5/2018 | Lee et al. | |
| 2018/0174680 A1 | 6/2018 | Sampath et al. | |
| 2018/0181716 A1 | 6/2018 | Mander et al. | |
| 2018/0182471 A1* | 6/2018 | Yelton | G16H 50/70 |
| 2018/0182475 A1 | 6/2018 | Cossler et al. | |
| 2018/0183663 A1 | 6/2018 | Teeter et al. | |
| 2018/0219842 A1 | 8/2018 | Bellala et al. | |
| 2018/0225311 A1 | 8/2018 | Bandopadhyay et al. | |
| 2018/0261070 A1 | 9/2018 | Stevens et al. | |
| 2018/0314802 A1* | 11/2018 | Dreyer | G16H 40/63 |
| 2018/0315182 A1* | 11/2018 | Rapaka | G06T 7/0012 |
| 2018/0330115 A1 | 11/2018 | Felton | |
| 2018/0351791 A1 | 12/2018 | Nagarajan et al. | |
| 2018/0364692 A1 | 12/2018 | Bradbury et al. | |
| 2018/0365121 A1 | 12/2018 | Harneja et al. | |
| 2018/0367396 A1 | 12/2018 | Kompella et al. | |
| 2018/0367412 A1 | 12/2018 | Sethi et al. | |
| 2019/0081850 A1 | 3/2019 | Nazar et al. | |
| 2019/0132256 A1 | 5/2019 | Wada et al. | |
| 2019/0133445 A1 | 5/2019 | Eteminan et al. | |
| 2019/0180868 A1* | 6/2019 | Makram | G06N 20/00 |
| 2019/0228379 A1 | 7/2019 | Shimada et al. | |
| 2019/0231280 A1 | 8/2019 | Tudor | |
| 2019/0266056 A1 | 8/2019 | Wu | |
| 2019/0318026 A1 | 10/2019 | Joseph et al. | |
| 2019/0354914 A1 | 11/2019 | Nicholas | |
| 2019/0378619 A1* | 12/2019 | Meyer | G16H 50/70 |
| 2019/0386891 A1 | 12/2019 | Chitalia et al. | |
| 2020/0013490 A1* | 1/2020 | Rumoro | G16H 10/60 |
| 2020/0098461 A1 | 3/2020 | Macoviak et al. | |
| 2020/0104998 A1 | 4/2020 | Dacosta | |
| 2020/0221951 A1 | 7/2020 | Amble et al. | |
| 2020/0244533 A1 | 7/2020 | Gopalarathnam | |
| 2020/0296053 A1 | 9/2020 | Garcia et al. | |
| 2020/0320178 A1 | 10/2020 | Gallagher | |
| 2020/0403855 A1 | 12/2020 | Sarood et al. | |
| 2021/0064812 A1 | 3/2021 | Walkingshaw et al. | |
| 2021/0105518 A1 | 4/2021 | Kannan et al. | |
| 2021/0168455 A1 | 6/2021 | Campbell et al. | |
| 2021/0209249 A1 | 7/2021 | Hoffer | |
| 2021/0224634 A1 | 7/2021 | Chen et al. | |
| 2022/0028503 A1* | 1/2022 | Bull | G16H 20/70 |
| 2022/0175325 A1 | 6/2022 | Fukushima et al. | |
| 2022/0385581 A1 | 12/2022 | Delos Reyes et al. | |

FOREIGN PATENT DOCUMENTS

| | | |
|---|---|---|
| WO | 2011143817 A1 | 11/2011 |
| WO | 2012004634 A1 | 1/2012 |
| WO | 2012160567 A1 | 11/2012 |
| WO | 2021087317 A1 | 5/2021 |

OTHER PUBLICATIONS

"Aggregations", Elasticsearch Reference [6.5], Elastic Co Website, Available online at: https://www.elastic.co/guide/en/elasticsearch/reference/current/search-aggregations.html, Accessed from internet on Jan. 17, 2019, pp. 1-7.

"Ask a Doctor Online", Lybrate website, Available Online at: https://www.lybrate.com/, Accessed from Internet on Jan. 25, 2019, pp. 1-98.

"Blue Cross/Blue Shield, Find a Doctor Website", Available Online at: https://www.bcbs.com/find-a-doctor, Accessed from internet on Jan. 25, 2019, 1 page.

"Bucket Aggregations", Elasticsearch Reference [6.5], Elastic Co., Website, Available Online at: https://www.elastic.co/guide/en/elasticsearch/reference/current/search-aggregations-bucket.html, Accessed from Internet on Jan. 17, 2019, pp. 1-6.

"Doctor.com website", Available Online at: https://www.doctor.com/, Accessed from Internet on Jan. 25, 2019, 5 pages.

"Healthgrade Find a Doctor Website", Available online at: https://www.healthgrades.com/find-a-doctor, Accessed from Internet on Jan. 25, 2019, 6 pages.

"Random Scoring", Elasticsearch: The Definitive Guide [2.x], Elastic Co Website, Available online at: https://www.elastic.co/guide/en/elasticsearch/guide/currenU/random-scoring.html, Accessed from Internet on Jan. 17, 2019, pp. 1-6.

"The Power Behind 'Patient-Powered Search'", ZocDoc Website, Available online at: https://www.zocdoc.com/about/blog/tech/power-behind-patientpowered-search/, Accessed from Internet on Jan. 25, 2019, pp. 1-13.

"Yellow Pages Website", Available Online at: https://www.yellowpages.com/, Accessed from Internet on Jan. 25, 2019, 4 pages.

U.S. Appl. No. 14/172,736, "Advisory Action", Nov. 19, 2015, 6 pages.

U.S. Appl. No. 14/172,736, "Final Office Action", Jul. 30, 2015, 23 pages.

U.S. Appl. No. 14/172,736, "First Action Interview Office Action Summary", May 29, 2014, 5 pages.

U.S. Appl. No. 14/172,736, "First Action Interview Pilot Program Pre-Interview Communication", Mar. 21, 2014, 6 pages.

U.S. Appl. No. 14/172,736, "Non-Final Office Action", Aug. 10, 2016, 11 pages.

U.S. Appl. No. 14/172,736, "Non-Final Office Action", Dec. 10, 2014, 23 pages.

U.S. Appl. No. 14/172,736, "Notice of Allowance", Apr. 12, 2017, 13 pages.

U.S. Appl. No. 14/304,604, "Advisory Action", Aug. 30, 2016, 4 pages.

U.S. Appl. No. 14/304,604, "Final Office Action", Nov. 16, 2017, 11 pages.

U.S. Appl. No. 14/304,604, "Final Office Action", Mar. 3, 2015, 12 pages.

U.S. Appl. No. 14/304,604, "Final Office Action", May 12, 2016, 17 pages.

U.S. Appl. No. 14/304,604, "First Action Interview Office Action Summary", Jun. 7, 2017, 4 pages.

U.S. Appl. No. 14/304,604, "First Action Interview Office Action Summary—2 Mo", Sep. 17, 2014, 6 pages.

U.S. Appl. No. 14/304,604, "First Action Interview Pilot Program Pre-Interview Communication", Dec. 20, 2016, 4 pages.

U.S. Appl. No. 14/304,604, "First Action Interview Pilot Program Pre-Interview Communication", Jul. 30, 2014, 5 pages.

U.S. Appl. No. 14/304,604, "Non-Final Office Action", Sep. 14, 2015, 16 pages.

U.S. Appl. No. 14/304,604, "Notice of Allowance", Apr. 17, 2018, 9 pages.

U.S. Appl. No. 14/630,393, "Non-Final Office Action", Apr. 30, 2015, 13 pages.

U.S. Appl. No. 14/630,393, "Notice of Allowance", Jul. 29, 2015, 14 pages.

U.S. Appl. No. 14/843,747, "Final Office Action", Apr. 26, 2016, 12 pages.

U.S. Appl. No. 14/843,747, "First Action Interview Office Action Summary", Feb. 12, 2016, 6 pages.

(56) References Cited

OTHER PUBLICATIONS

U.S. Appl. No. 14/843,747 , "First Action Interview Pilot Program Pre-Interview Communication", Nov. 23, 2015, 5 pages.
U.S. Appl. No. 14/843,747 , "Notice of Allowance", Aug. 11, 2016, 8 pages.
U.S. Appl. No. 14/954,249 , "Non-Final Office Action", Jun. 28, 2017, 33 pages.
U.S. Appl. No. 14/954,249 , "Notice of Allowance", Oct. 20, 2017, 10 pages.
U.S. Appl. No. 14/957,911 , "Notice of Allowance", Jan. 24, 2019, 9 pages.
U.S. Appl. No. 14/967,027 , "Final Office Action", Aug. 8, 2019, 12 pages.
U.S. Appl. No. 14/967,027 , "Non-Final Office Action", Jul. 12, 2018, 12 pages.
U.S. Appl. No. 14/967,027 , "Non-Final Office Action", Jan. 25, 2019, 14 pages.
U.S. Appl. No. 14/967,027 , "Notice of Allowance", Dec. 23, 2019, 5 pages.
U.S. Appl. No. 14/974,438 , "Final Office Action", Nov. 5, 2018, 38 pages.
U.S. Appl. No. 14/974,438 , "Final Office Action", Dec. 4, 2019, 45 pages.
U.S. Appl. No. 14/974,438 , "Non-Final Office Action", May 14, 2018, 35 Pages.
U.S. Appl. No. 14/974,438 , "Non-Final Office Action", Apr. 1, 2019, 41 pages.
U.S. Appl. No. 14/974,438 , "U.S. Appl. No.", Dec. 18, 2015, 79 pages.
U.S. Appl. No. 14/989,520 , "Final Office Action", Nov. 26, 2018, 41 pages.
U.S. Appl. No. 14/989,520 , "Final Office Action", Dec. 5, 2019, 46 pages.
U.S. Appl. No. 14/989,520 , "Non Final Office Action", May 31, 2018, 30 pages.
U.S. Appl. No. 14/989,520 , "Non-Final Office Action", Apr. 5, 2019, 46 pages.
U.S. Appl. No. 14/989,520 , "U.S. Appl. No.", Jan. 6, 2016, 72 pages.
U.S. Appl. No. 14/990,076 , "Restriction Requirement", Jun. 28, 2018, 6 pages.
U.S. Appl. No. 14/990,076 , "U.S. Appl. No.", Jan. 7, 2016, 96 pages.
U.S. Appl. No. 15/156,503 , "Final Office Action", Sep. 12, 2019, 36 pages.
U.S. Appl. No. 15/156,503 , "Non-Final Office Action", Mar. 18, 2019, 35 pages.
U.S. Appl. No. 15/156,503 , "Notice of Allowance", Jan. 10, 2020, 25 pages.
U.S. Appl. No. 15/286,397 , "Advisory Action", Apr. 13, 2018, 4 Pages.
U.S. Appl. No. 15/286,397 , "Final Office Action", Nov. 28, 2017, 27 pages.
U.S. Appl. No. 15/286,397 , "Final Office Action", Jan. 23, 2019, 38 pages.
U.S. Appl. No. 15/286,397 , "First Action Interview Office Action Summary", Jun. 5, 2017, 32 pages.
U.S. Appl. No. 15/286,397 , "First Action Interview Pilot Program Pre-Interview Communication", Feb. 15, 2017, 25 pages.
U.S. Appl. No. 15/286,397 , "Non Final Office Action", Jun. 12, 2018, 27 Pages.
U.S. Appl. No. 15/286,397 , "Notice of Allowance", May 7, 2019, 26 pages.
U.S. Appl. No. 15/299,617 , "Notice of Allowance", Feb. 24, 2017, 8 pages.
U.S. Appl. No. 15/357,745 , "Non-Final Office Action", Feb. 9, 2017, 20 pages.
U.S. Appl. No. 15/357,745 , "Notice of Allowance", Nov. 21, 2016.
U.S. Appl. No. 15/357,745 , "Notice of Allowance", May 24, 2017, 14 pages.
U.S. Appl. No. 15/357,770 , "First Action Interview Office Action Summary", Apr. 25, 2017, 5 pages.
U.S. Appl. No. 15/357,770 , "First Action Interview Pilot Program Pre-Interview Communication", Feb. 9, 2017, 5 pages.
U.S. Appl. No. 15/369,434 , "First Action Interview Office Action Summary", Jul. 9, 2019, 5 pages.
U.S. Appl. No. 15/369,434 , "First Action Interview Pilot Program Pre-Interview Communication", Apr. 15, 2019, 3 pages.
U.S. Appl. No. 15/369,434 , "Notice of Allowance", Nov. 6, 2019, 7 pages.
U.S. Appl. No. 15/476,243 , "Non-Final Office Action", Jul. 3, 2017, 6 pages.
U.S. Appl. No. 15/476,243 , "Notice of Allowance", Dec. 28, 2017, 16 pages.
U.S. Appl. No. 15/479,011 , "Advisory Action", Mar. 12, 2018, 4 pages.
U.S. Appl. No. 15/479,011 , "Final Office Action", Nov. 16, 2017, 39 pages.
U.S. Appl. No. 15/479,011 , "Non Final Office Action", Jul. 11, 2018, 45 Pages.
U.S. Appl. No. 15/479,011 , "Non-Final Office Action", May 31, 2017, 26 pages.
U.S. Appl. No. 15/479,011 , "Notice of Allowance", Jan. 3, 2019, 18 pages.
U.S. Appl. No. 15/594,383 , "Notice of Allowance", Sep. 14, 2017, 28 pages.
U.S. Appl. No. 15/627,125 , "Advisory Action", Jul. 13, 2020, 5 pages.
U.S. Appl. No. 15/627,125 , "Final Office Action", Feb. 26, 2020, 14 pages.
U.S. Appl. No. 15/627,125 , "Non-Final Office Action", Oct. 1, 2019, 13 pages.
U.S. Appl. No. 15/627,125 , "Non-Final Office Action", Aug. 13, 2020, 14 pages.
U.S. Appl. No. 15/627,125 , "Notice of Allowance", Feb. 2, 2021, 7 pages.
U.S. Appl. No. 15/684,747 , "Notice of Allowance", Oct. 19, 2017, 15 pages.
U.S. Appl. No. 15/844,098 , "Notice of Allowance", Jan. 9, 2019, 9 pages.
U.S. Appl. No. 15/844,098 , "Supplemental Notice of Allowability", Apr. 24, 2019, 2 pages.
U.S. Appl. No. 15/888,919 , "Corrected Notice of Allowability", Jun. 10, 2019, 12 pages.
U.S. Appl. No. 15/888,919 , "Corrected Notice of Allowability", Apr. 2, 2019, 19 pages.
U.S. Appl. No. 15/888,919 , "First Action Interview Office Action Summary", Jul. 3, 2018, 5 pages.
U.S. Appl. No. 15/888,919 , "First Action Interview Pilot Program Pre-Interview Communication", Apr. 16, 2018, 6 pages.
U.S. Appl. No. 15/888,919 , "Notice of Allowance", Oct. 17, 2018, 16 pages.
U.S. Appl. No. 15/896,788 , "First Action Interview Office Action Summary", Feb. 11, 2018, 6 pages.
U.S. Appl. No. 15/896,788 , "First Action Interview Pilot Program Pre-Interview Communication", Jan. 11, 2019, 6 pages.
U.S. Appl. No. 15/896,788 , "Notice of Allowance", Jul. 17, 2019, 24 pages.
U.S. Appl. No. 15/902,897 , "Corrected Notice of Allowability", Apr. 26, 2019, 2 pages.
U.S. Appl. No. 15/902,897 , "Non-Final Office Action", Nov. 21, 2018, 16 pages.
U.S. Appl. No. 15/902,897 , "Notice of Allowance", Jan. 24, 2019, 9 pages.
U.S. Appl. No. 15/980,575 , "Notice of Allowance", Sep. 5, 2019, 12 pages.
U.S. Appl. No. 16/041,578 , "First Action Interview Office Action Summary", Nov. 23, 2018, 15 pages.
U.S. Appl. No. 16/041,578 , "First Action Interview Pilot Program Pre-Interview Communication", Sep. 28, 2018, 13 pages.
U.S. Appl. No. 16/041,578 , "Notice of Allowance", Mar. 28, 2019, 11 pages.

(56) References Cited

OTHER PUBLICATIONS

U.S. Appl. No. 16/170,379, "Non-Final Office Action", Feb. 1, 2019, 12 pages.
U.S. Appl. No. 16/170,379, "Notice of Allowance", Jun. 27, 2019, 8 pages.
U.S. Appl. No. 16/358,282, "Corrected Notice of Allowability", Mar. 5, 2020, 8 pages.
U.S. Appl. No. 16/358,282, "Final Office Action", Sep. 26, 2019, 15 pages.
U.S. Appl. No. 16/358,282, "Non-Final Office Action", May 28, 2019, 13 pages.
U.S. Appl. No. 16/358,282, "Notice of Allowance", Jan. 14, 2020, 13 pages.
U.S. Appl. No. 16/397,369, "Notice of Allowance", Jun. 23, 2020, 9 pages.
U.S. Appl. No. 16/451,547, "Non-Final Office Action", Aug. 10, 2021, 28 pages.
U.S. Appl. No. 16/451,547, "Notice of Allowance", Jan. 27, 2022, 19 pages.
U.S. Appl. No. 16/510,674, "First Action Interview Pilot Program Pre-Interview Communication", Apr. 8, 2020, 6 pages.
U.S. Appl. No. 16/510,674, "Notice of Allowance", May 20, 2020, 18 pages.
U.S. Appl. No. 16/534,417, "Advisory Action", Aug. 8, 2022, 4 pages.
U.S. Appl. No. 16/534,417, "Advisory Action", Sep. 28, 2021, 4 pages.
U.S. Appl. No. 16/534,417, "Final Office Action", May 25, 2021, 35 pages.
U.S. Appl. No. 16/534,417, "Final Office Action", May 9, 2022, 37 pages.
U.S. Appl. No. 16/534,417, "Non-Final Office Action", Jun. 26, 2020, 28 pages.
U.S. Appl. No. 16/534,417, "Non-Final Office Action", Nov. 4, 2020, 31 pages.
U.S. Appl. No. 16/534,417, "Non-Final Office Action", Dec. 7, 2021, 33 pages.
U.S. Appl. No. 16/534,417, "Non-Final Office Action", Sep. 1, 2022, 39 pages.
U.S. Appl. No. 16/534,417, "U.S. Appl. No.", Aug. 7, 2019, 103 pages.
U.S. Appl. No. 16/545,998, "Notice of Allowance", Dec. 12, 2019, 11 pages.
U.S. Appl. No. 16/580,114, "Notice of Allowance", Oct. 23, 2020, 10 pages.
U.S. Appl. No. 16/586,376, "Advisory Action", Jan. 18, 2022, 4 pages.
U.S. Appl. No. 16/586,376, "Final Office Action", Oct. 6, 2021, 11 pages.
U.S. Appl. No. 16/586,376, "Non-Final Office Action", Feb. 11, 2022, 14 pages.
U.S. Appl. No. 16/586,376, "Non-Final Office Action", Jun. 23, 2021, 3 pages.
U.S. Appl. No. 16/586,376, "Notice of Allowance", Aug. 9, 2022, 7 pages.
U.S. Appl. No. 16/586,376, "U.S. Appl. No.", Sep. 27, 2019, 164 pages.
U.S. Appl. No. 16/700,010, "Advisory Action", Mar. 17, 2021, 4 pages.
U.S. Appl. No. 16/700,010, "Corrected Notice of Allowability", Aug. 31, 2022, 10 pages.
U.S. Appl. No. 16/700,010, "Final Office Action", Jan. 10, 2022, 13 pages.
U.S. Appl. No. 16/700,010, "Final Office Action", Oct. 16, 2020, 21 pages.
U.S. Appl. No. 16/700,010, "First Action Interview Office Action Summary", Jun. 4, 2020, 5 pages.
U.S. Appl. No. 16/700,010, "First Action Interview Pilot Program Pre-Interview Communication", Feb. 21, 2020, 4 pages.
U.S. Appl. No. 16/700,010, "Non-Final Office Action", Aug. 23, 2021, 12 pages.
U.S. Appl. No. 16/700,010, "Notice of Allowance", May 24, 2022, 14 pages.
U.S. Appl. No. 16/709,248, "First Action Interview Pilot Program Pre-Interview Communication", Feb. 13, 2020, 4 pages.
U.S. Appl. No. 16/709,248, "Notice of Allowance", May 18, 2020, 16 pages.
U.S. Appl. No. 16/782,042, "Final Office Action", Nov. 17, 2020, 11 pages.
U.S. Appl. No. 16/782,042, "First Action Interview Office Action Summary", Jul. 8, 2020, 12 pages.
U.S. Appl. No. 16/782,042, "First Action Interview Pilot Program Pre-Interview Communication", Apr. 7, 2020, 9 pages.
U.S. Appl. No. 16/782,042, "Notice of Allowance", Jun. 1, 2021, 18 pages.
U.S. Appl. No. 16/809,370, "First Action Interview Office Action Summary", Feb. 24, 2021, 4 pages.
U.S. Appl. No. 16/809,370, "First Action Interview Pilot Program Pre-Interview Communication", Dec. 18, 2020, 4 pages.
U.S. Appl. No. 16/809,370, "Notice of Allowance", Jul. 13, 2021, 18 pages.
U.S. Appl. No. 16/849,193, "Notice of Allowance", May 19, 2021, 7 pages.
U.S. Appl. No. 16/883,765, "Notice of Allowance", Aug. 9, 2021, 28 pages.
U.S. Appl. No. 16/883,858, "Non-Final Office Action", Dec. 5, 2023, 15 pages.
U.S. Appl. No. 16/883,858, "U.S. Appl. No.", May 26, 2020, 112 pages.
U.S. Appl. No. 16/888,937, "Corrected Notice of Allowability", Jan. 13, 2022, 3 pages.
U.S. Appl. No. 16/888,937, "Non-Final Office Action", Jul. 26, 2021, 9 pages.
U.S. Appl. No. 16/888,937, "Notice of Allowance", Nov. 10, 2021, 11 pages.
U.S. Appl. No. 17/020,586, "Notice of Allowance", Nov. 10, 2021, 11 pages.
U.S. Appl. No. 17/061,850, "Non-Final Office Action", May 4, 2021, 13 pages.
U.S. Appl. No. 17/061,850, "Notice of Allowance", Sep. 17, 2021, 11 pages.
U.S. Appl. No. 17/061,851, "Non-Final Office Action", Oct. 28, 2021, 10 pages.
U.S. Appl. No. 17/061,851, "Notice of Allowance", Feb. 15, 2022, 5 pages.
U.S. Appl. No. 17/075,993, "Notice of Allowance", May 13, 2022, 11 pages.
U.S. Appl. No. 17/137,055, "Non-Final Office Action", Mar. 30, 2023, 24 pages.
U.S. Appl. No. 17/137,055, "Notice of Allowance", Oct. 4, 2023, 10 pages.
U.S. Appl. No. 17/137,055, "U.S. Appl. No.", Dec. 29, 2020, 123 pages.
U.S. Appl. No. 17/141,414, "Final Office Action", May 19, 2023, 32 pages.
U.S. Appl. No. 17/141,414, "Non-Final Office Action", Oct. 27, 2022, 29 pages.
U.S. Appl. No. 17/141,414, "Non-Final Office Action", Dec. 12, 2023, 34 pages.
U.S. Appl. No. 17/159,700, "Final Office Action", Nov. 29, 2023, 21 pages.
U.S. Appl. No. 17/159,700, "Non-Final Office Action", Apr. 26, 2023, 26 pages.
U.S. Appl. No. 17/178,995, "Corrected Notice of Allowability", Jan. 24, 2024, 2 pages.
U.S. Appl. No. 17/178,995, "Non-Final Office Action", Jun. 30, 2023, 23 pages.
U.S. Appl. No. 17/178,995, "Notice of Allowance", Oct. 12, 2023, 10 pages.
U.S. Appl. No. 17/181,025, "Non-Final Office Action", Oct. 12, 2021, 27 pages.

(56) References Cited

OTHER PUBLICATIONS

U.S. Appl. No. 17/181,025, "Notice of Allowance", Mar. 2, 2022, 8 pages.
U.S. Appl. No. 17/194,138, "Notice of Allowance", Apr. 6, 2022, 11 pages.
U.S. Appl. No. 17/338,380, "Advisory Action", Nov. 3, 2022, 4 pages.
U.S. Appl. No. 17/338,380, "Final Office Action", Aug. 19, 2022, 13 pages.
U.S. Appl. No. 17/338,380, "Non-Final Office Action", Mar. 15, 2022, 12 pages.
U.S. Appl. No. 17/338,380, "Non-Final Office Action", Dec. 13, 2022, 14 pages.
U.S. Appl. No. 17/338,380, "U.S. Appl. No.", Jun. 3, 2021, 117 pages.
U.S. Appl. No. 17/364,502, "Notice of Allowance", Sep. 20, 2021, 15 pages.
U.S. Appl. No. 17/475,647, "Final Office Action", Aug. 4, 2023, 25 pages.
U.S. Appl. No. 17/475,647, "Non-Final Office Action", Dec. 29, 2022, 24 pages.
U.S. Appl. No. 17/475,647, "U.S. Appl. No.", Sep. 15, 2021, 89 pages.
U.S. Appl. No. 17/487,934, "Final Office Action", Apr. 28, 2023, 9 pages.
U.S. Appl. No. 17/487,934, "Non-Final Office Action", Oct. 12, 2022, 10 pages.
U.S. Appl. No. 17/487,934, "Non-Final Office Action", Oct. 26, 2023, 10 pages.
U.S. Appl. No. 17/487,934, "U.S. Appl. No.", Sep. 28, 2021, 127 pages.
U.S. Appl. No. 17/499,424, "Notice of Allowance", Apr. 13, 2022, 11 pages.
U.S. Appl. No. 17/521,689, "Notice of Allowance", Mar. 31, 2023, 11 pages.
17/523, 190, "Non-Final Office Action", Jun. 20, 2023, 24 pages.
U.S. Appl. No. 17/748,976, "U.S. Appl. No.", May 19, 2022, 82 pages.
U.S. Appl. No. 18/176,311, "Non-Final Office Action", Mar. 13, 2024, 15 pages.
U.S. Appl. No. 18/176,314, "Non Final Office Action", Jul. 19, 2023, 16 pages.
U.S. Appl. No. 18/176,314, "Notice of Allowance", Feb. 15, 2024, 8 pages.
U.S. Appl. No. 18/176,314, "Notice of Allowance", Jan. 4, 2024, 9 pages.
Gulshan et al., "Development and Validation of a Deep Learning Algorithm for Detection of Diabetic Retinopathy in Retinal Fundus Photographs", Jama, vol. 316, No. 22, Dec. 13, 2016, pp. 2402-2410.
Haque et al., "Towards Vision-Based Smart Hospitals: A System for Tracking and Monitoring Hand Hygiene Compliance", Proceedings of the 2nd Machine Learning for Healthcare Conference, PMLR, vol. 68, Apr. 24, 2018, pp. 1-13.
Jiang et al., "How to Find your Appropriate Doctor, An Integrated Recommendation Framework in Big Data Context", IEEE Symposium on Computational Intelligence in Healthcare and e-health (CICARE), Dec. 2014, 5 pages.
Lee et al., "A Privacy-Enabled Architecture for an RFID-Based Location Monitoring System", Proceedings of the 7th ACM International Symposium on Mobility Management and Wireless Access, Oct. 26, 2009, pp. 128-131.
Lichtenthal, "Quick Guide to Cardiopulmonary Care", Edwards Life Sciences, 2010, 188 page.
McGee et al., "Quick Guide to Cardiopulmonary Care", 2nd Edition, Edwards Critical Care Education, 2010, 100 pages.
Ramezani et al., "Diagnostic Information for Compliance Checking of Temporal Compliance Requirements", Lecture Notes in Computer Science, vol. 7908, Jun. 2013, pp. 1-16.
Wang et al., "Learning to Rank with Selection Bias in Personal Search", Google Inc., Mountain View, CA 94043, Jul. 17-21, 2016, 10 pages.
Yao et al., "Leveraging Complex Event Processing for Smart Hospitals Using RFID", Singapore Management University Institutional Knowledge at Singapore Management University, Journal of Network and Computer Applications, vol. 34, No. 3, May 2011, pp. 799-810.
Yumoto et al., "Finding Rare Web Pages by Relevancy and Atypicality in a Category", Biomedical Soft Computing and Human Sciences, vol. 22, No. 1, Aug. 2013, pp. 9-18.

\* cited by examiner

```
                                                                    ← 2300
```

┌─────────────────────────────────────────────────────────────┐
│ RECEIVE USER DATA ASSOCIATED WITH A USER OF A SERVICE FACILITY, THE │
│ SERVICE FACILITY INCLUDING A PLURALITY OF SERVICE UNITS, THE USER BEING │
│ ASSIGNED TO A FIRST SERVICE UNIT OF THE PLURALITY OF SERVICE UNITS 2302 │
└─────────────────────────────────────────────────────────────┘
                               ↓
┌─────────────────────────────────────────────────────────────┐
│ DETERMINE, BY A CLASSIFICATION MODEL, A CLASSIFICATION FOR THE USER │
│ THAT IS ASSOCIATED WITH A PREDICTED FUTURE CONDITION OF THE USER 2304 │
└─────────────────────────────────────────────────────────────┘
                               ↓
┌─────────────────────────────────────────────────────────────┐
│ ASSIGN THE USER TO A USER GROUP BASED ON THE CLASSIFICATION 2306 │
└─────────────────────────────────────────────────────────────┘
                               ↓
┌─────────────────────────────────────────────────────────────┐
│ DETERMINE A RECOMMENDATION FOR THE USER, THE RECOMMENDATION │
│ ASSOCIATED WITH ASSIGNING THE USER TO A SECOND SERVICE UNIT OF THE │
│ PLURALITY OF SERVICE UNITS  2308 │
└─────────────────────────────────────────────────────────────┘
                               ↓
┌─────────────────────────────────────────────────────────────┐
│ PROVIDE THE RECOMMENDATION FOR PRESENTATION ON A USER DEVICE OF A │
│ USER SERVICE PROVIDER 2310 │
└─────────────────────────────────────────────────────────────┘

FIG. 23

```
┌─────────────────────────────────────────────────────────────┐
│ RECEIVE A PLURALITY OF IMAGES THAT IDENTIFIES A BED CLEANING │
│ PROCESS OF A BED, THE BED CLEANING PROCESS PERFORMED WITHIN  │
│ A PORTION OF A SERVICE UNIT OF A SERVICE FACILITY 2402       │
└─────────────────────────────────────────────────────────────┘
                              │
                              ▼
┌─────────────────────────────────────────────────────────────┐
│ INPUT THE PLURALITY OF USER DATA INTO A CLASSIFICATION MODEL │
│ THAT IS TRAINED TO DETERMINE A STATUS OF THE BED BASED AT    │
│ LEAST IN PART ON THE PLURALITY OF IMAGES 2404                │
└─────────────────────────────────────────────────────────────┘
                              │
                              ▼
┌─────────────────────────────────────────────────────────────┐
│ DETERMINE, BY THE CLASSIFICATION MODEL, THE STATUS OF THE    │
│ BED 2406                                                     │
└─────────────────────────────────────────────────────────────┘
                              │
                              ▼
┌─────────────────────────────────────────────────────────────┐
│ ASSIGN THE BED TO A BED GROUP BASED AT LEAST IN PART ON THE  │
│ DETERMINED STATUS OF THE BED 2408                            │
└─────────────────────────────────────────────────────────────┘
                              │
                              ▼
┌─────────────────────────────────────────────────────────────┐
│ GENERATE A VISUAL REPRESENTATION OF THE ASSIGNED BED GROUP   │
│ OF THE BED WITHIN THE SERVICE UNIT 2410                      │
└─────────────────────────────────────────────────────────────┘
                              │
                              ▼
┌─────────────────────────────────────────────────────────────┐
│ PROVIDE THE VISUAL REPRESENTATION TO A USER DEVICE OF A USER │
│ SERVICE PROVIDER 2412                                        │
└─────────────────────────────────────────────────────────────┘
```

┌─────────────────────────────────────────────────────────────────┐
│ RECEIVE USER DATA ASSOCIATED WITH A USER OF A SERVICE UNIT OF A │
│ SERVICE FACILITY, THE SERVICE UNIT BEING ONE OF A PLURALITY OF  │
│ SERVICE UNITS OF THE SERVICE FACILITY, EACH SERVICE UNIT        │
│ ASSOCIATED WITH AT LEAST ONE CLINICIAN 2502                     │
└─────────────────────────────────────────────────────────────────┘
                                 │
                                 ▼
┌─────────────────────────────────────────────────────────────────┐
│ MAINTAIN AT LEAST ONE TASK ASSOCIATED WITH USER SERVICE FOR THE │
│ USER AND ASSIGNED TO THE AT LEAST ONE CLINICIAN, THE AT LEAST   │
│ ONE TASK ASSOCIATED WITH A TIMER THAT CORRESPONDS TO A TARGET   │
│ TIMEFRAME IN WHICH THE TASK SHOULD BE PERFORMED 2504            │
└─────────────────────────────────────────────────────────────────┘
                                 │
                                 ▼
┌─────────────────────────────────────────────────────────────────┐
│ DETERMINING, BY A PREDICTION MODEL, A FIRST RISK THAT THE AT    │
│ LEAST ONE TASK WILL NOT BE PERFORMED WITHIN THE TARGET          │
│ TIMEFRAME 2506                                                  │
└─────────────────────────────────────────────────────────────────┘
                                 │
                                 ▼
┌─────────────────────────────────────────────────────────────────┐
│ CLASSIFYING, BY THE SERVICE VISUALIZATION SYSTEM, THE SERVICE   │
│ UNIT AS A HOT SPOT BASED AT LEAST IN PART ON THE FIRST RISK 2508│
└─────────────────────────────────────────────────────────────────┘
                                 │
                                 ▼
┌─────────────────────────────────────────────────────────────────┐
│ DETERMINING A RECOMMENDATION THAT A SECOND CLINICIAN BE ASSIGNED│
│ TO THE SERVICE UNIT, THE SECOND CLINICIAN CURRENTLY ASSIGNED TO │
│ ANOTHER SERVICE UNIT OF THE PLURALITY OF SERVICE UNITS 2510     │
└─────────────────────────────────────────────────────────────────┘
                                 │
                                 ▼
┌─────────────────────────────────────────────────────────────────┐
│ PROVIDING THE RECOMMENDATION FOR PRESENTATION ON A USER DEVICE  │
│ OF A USER SERVICE COORDINATOR FOR USE IN COORDINATING CLINICIAN │
│ ASSIGNMENTS AMONG THE PLURALITY OF SERVICE UNITS OF THE SERVICE │
│ FACILITY 2512                                                   │
└─────────────────────────────────────────────────────────────────┘
```

RECEIVE USER DATA ASSOCIATED WITH A USER OF A SERVICE FACILITY, THE USER BEING ASSIGNED TO A SERVICE UNIT OF A PLURALITY OF SERVICE UNITS OF THE SERVICE FACILITY 2802

DETERMINE A CLASSIFICATION FOR THE USER BASED AT LEAST IN PART ON THE USER DATA, THE CLASSIFICATION ASSOCIATED WITH A CONDITION OR TREATMENT STATUS OF THE USER FOR WHICH SPECIALIZED SERVICE FOR THE USER IS BENEFICIAL DURING AN EMERGENCY EVENT 2804

ASSIGN THE USER TO A USER GROUP BASED AT LEAST IN PART ON THE CLASSIFICATION OF THE USER 2806

DETERMINE A RECOMMENDATION FOR PROVIDING THE SPECIALIZED SERVICE FOR THE USER BASED AT LEAST IN PART ON THE ASSIGNED USER GROUP 2808

PROVIDE THE RECOMMENDATION FOR PRESENTATION ON A USER DEVICE OF A USER SERVICE PROVIDER FOR USE IN COORDINATING USER SERVICE FOR THE USER 2810

FIG. 28

```
                                                              ← 2900
┌─────────────────────────────────────────────────────────────────┐
│ RECEIVE USER DATA ASSOCIATED WITH A USER OF A SERVICE FACILITY, │
│ THE USER BEING ASSIGNED TO A SERVICE UNIT OF A PLURALITY OF     │
│ SERVICE UNITS OF THE SERVICE FACILITY 2902                      │
└─────────────────────────────────────────────────────────────────┘
                                 │
                                 ▼
┌─────────────────────────────────────────────────────────────────┐
│ DETECT AN OCCURRENCE OF A CLINICAL TRIGGER OF A PLURALITY OF    │
│ CLINICAL TRIGGERS BASED AT LEAST IN PART ON THE USER DATA, THE  │
│ PLURALITY OF CLINICAL TRIGGERS RESPECTIVELY ASSOCIATED WITH     │
│ ONE OR MORE INFECTION RISK INDICATORS 2904                      │
└─────────────────────────────────────────────────────────────────┘
                                 │
                                 ▼
┌─────────────────────────────────────────────────────────────────┐
│ DETERMINE A CLASSIFICATION FOR THE USER BASED AT LEAST IN PART  │
│ ON THE OCCURRENCE OF THE CLINICAL TRIGGER 2906                  │
└─────────────────────────────────────────────────────────────────┘
                                 │
                                 ▼
┌─────────────────────────────────────────────────────────────────┐
│ ASSIGN THE USER TO A USER GROUP BASED AT LEAST IN PART ON THE   │
│ CLASSIFICATION OF THE USER 2908                                 │
└─────────────────────────────────────────────────────────────────┘
                                 │
                                 ▼
┌─────────────────────────────────────────────────────────────────┐
│ DETERMINE A RECOMMENDATION FOR TREATING THE USER BASED AT       │
│ LEAST IN PART ON THE ASSIGNED USER GROUP 2910                   │
└─────────────────────────────────────────────────────────────────┘
                                 │
                                 ▼
┌─────────────────────────────────────────────────────────────────┐
│ PROVIDE THE RECOMMENDATION FOR PRESENTATION ON A USER DEVICE    │
│ OF A USER SERVICE PROVIDER FOR USE IN COORDINATING USER SERVICE │
│ FOR THE USER 2912                                               │
└─────────────────────────────────────────────────────────────────┘
```

FIG. 29

PREDICTIVE RESOURCE MANAGEMENT

CROSS-REFERENCE TO RELATED APPLICATIONS

This application is a continuation of U.S. patent application Ser. No. 17/178,995 filed on Feb. 18, 2021, which claims the benefit of and priority to U.S. Provisional Application No. 62/978,155, filed Feb. 18, 2020, both of which are hereby incorporated by reference in their entirety for all purposes.

BACKGROUND

The amount of data generated each day continues to grow. In some environments, some of this data may be stored, while a majority of it may be evaluated and abandoned or ignored. Users and computing devices are beginning to rely more and on this data to make decisions. This may be especially true when the data is introduced as part of an operational flow. However, the time required to sort through stored data can create inefficiencies and the fact that other data may typically be ignored or abandoned may create undesirable outcomes.

SUMMARY

Exemplary embodiments of the disclosure provide systems and methods for coordinating service for a user assigned to a service facility based at least in part classifying users and/or resources of the service facility into respective groupings. In some embodiments, a visual representation of one or more of these groupings may be presented in association with providing recommendations for coordinating service for the user. According to an aspect of the disclosure, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer—implemented method. The computer—implemented method also includes receiving, by a service visualization (SV) system, user data associated with a user of a plurality of users, the user assigned to a service unit of a plurality of service units of a service facility, the user data maintained by a service management system of a service organization, and the service facility being one of a plurality of service facilities affiliated with the service organization. The method also includes inputting, by the service visualization system, the user data into a classification model of the service visualization system. The method also includes determining, by the classification model, a classification for the user, the classification corresponding to at least one of a condition or service status of the user. The method also includes assigning, by the service visualization system, the user to a user group based at least in part on the classification of the user, the classification being common with members of the user group. The method also includes determining, by the service visualization system, resource status data corresponding to a status of a resource of the service facility, the resource associated with the assigned service unit. The method also includes assigning, by the service visualization system, the resource to a resource group based at least in part on the resource status, the resource status being common with members of the resource group. The method also includes generating, by the service visualization system, a visual representation of at least a portion of the assigned service unit of the service facility based at least in part on the assigned user group of the user and the assigned resource group of the resource. The method also includes providing, by the service visualization system, the visual representation to a user device of a user service provider for use in coordinating user service for the user among service units of the service facility. Other embodiments of this aspect include corresponding computer systems, apparatus, and computer programs recorded on one or more computer storage devices, each configured to perform the actions of the methods.

Other objects, advantages, and novel features of the present disclosure will become apparent from the following detailed description of the disclosure when considered in conjunction with the accompanying drawings.

BRIEF DESCRIPTION OF THE DRAWINGS

Various examples in accordance with the present disclosure will be described with reference to the drawings, in which:

FIG. 23 illustrates another process for coordinating user service based on user and/or resource classifications, according to at least one example;

FIG. 24 illustrates another process for coordinating user service based on user and/or resource classifications, according to at least one example;

FIG. 25 illustrates another process for coordinating user service based on user and/or resource classifications, according to at least one example;

FIG. 28 illustrates another process for coordinating user service based on user and/or resource classifications, according to at least one example;

FIG. 29 illustrates another process for coordinating user service based on user and/or resource classifications, according to at least one example.

DETAILED DESCRIPTION

Figure 1:
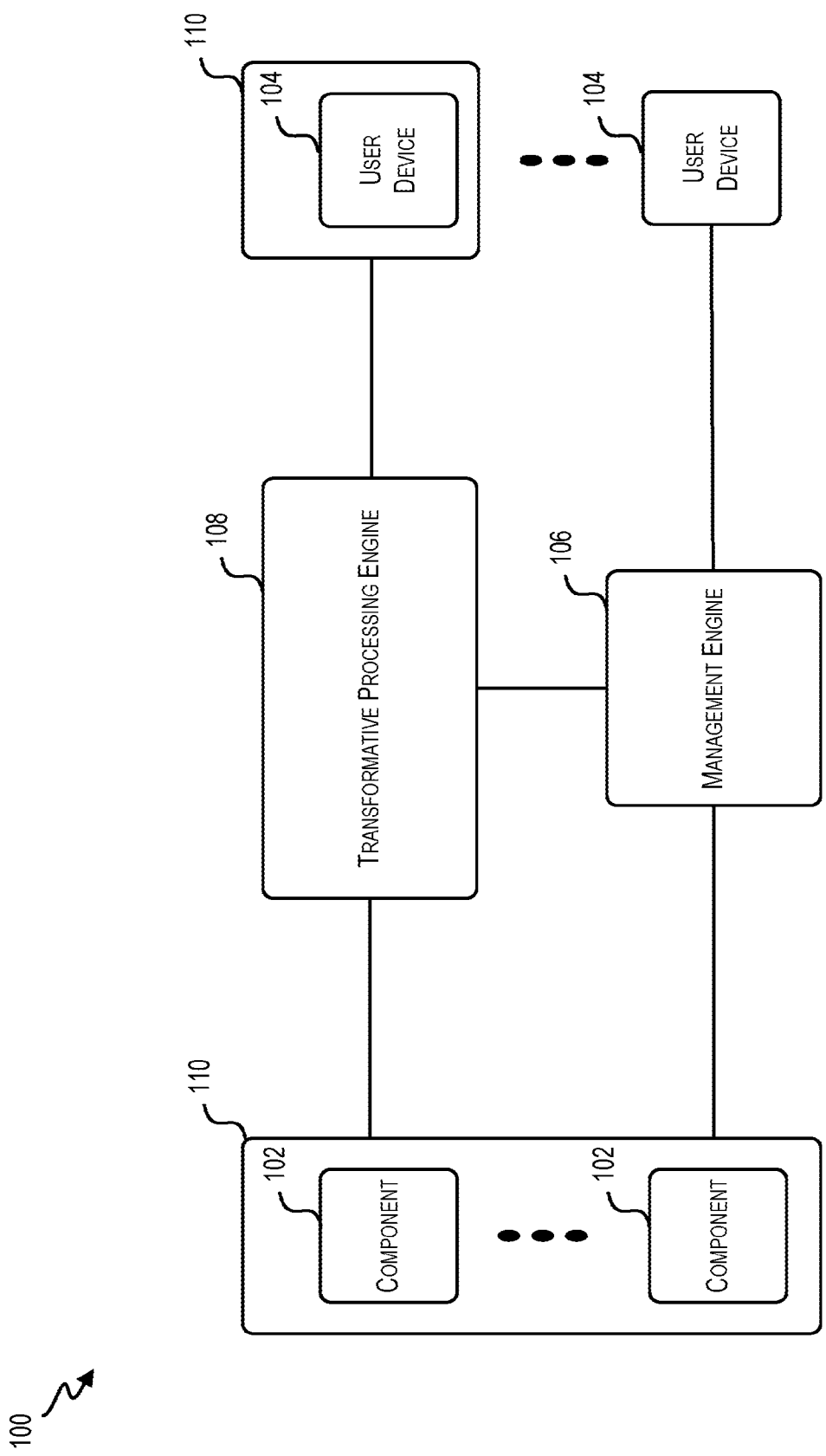
FIG. 1 is an example block diagram illustrating an interaction system in which techniques relating to coordinating user service based on user and/or resource classifications may be implemented, according to at least one example.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In one example, a service visualization (SV) system provides support for a user service provider (USP) that is providing service for users within a service organization (which may also be known as a "service system" or "enterprise"). The enterprise may include a plurality of divisions, and each division may include one or more service facilities. For example, the enterprise may geographically organized within the United States (U.S.), whereby there is a division per state, county, or the like. Each division may include one or more service facilities, for example, including clinics, labs, nursing facilities, rehabilitation centers, home health agencies, and any other user service center where a user may receive service by a service provider. A service facility may contain one or more service units, and a given service unit may, itself, contain one or more service units. In one example, a service unit may correspond to a department within the facility (e.g., an emergency department (ED), a surgery department, etc.). The given department may include one or more branches (e.g., a holding room, an operating room (OR), a waiting room, an emergency room (ER), etc.), each of which may be a service unit. Each branch may contain one or more beds, whereby a user may be assigned to a bed for receiving service. A nurse may be assigned to service for one or more users within a branch, and, the set of users/beds (e.g., resources) assigned to the nurse may form another service unit. It should be understood that any suitable hierarchical grouping of service units may be utilized for performing embodiments of the present disclosure (e.g., grouping by beds, types of users, clinicians, service type, departments, service facilities, divisions, enterprise level, etc.).

The service organization may maintain a service management computer system, which coordinates user service and records across the service organization (e.g., via one or multiple Electronic Medical Record (EMR) system(s)). In some examples, the service management system may further include (or be associated with) the SV system. In some cases, the USP may be an executive or administrator of the enterprise (e.g., at an enterprise level, division level, or service facility level). In some cases, the USP may be a clinician such as clinical nurse consultant (CNC), a user navigator, a user service coordinator, a floor nurse, a specialty nurse, a physician, or other type of service professional.

Typically, a service facility (e.g., a clinic) will admit a user for one or more conditions. For example, a user may check in to the ED of the service facility, where they may first be placed in a waiting room. When a bed becomes available (e.g., after a used (or "dirty") bed is cleaned), the user may be transferred to an emergency room of the ED, and then assigned to a bed. The user may then have one or more procedures performed (e.g., blood lab work, x-rays, other service, etc.). After a clinician becomes available and consults with the user (e.g., after reviewing the lab work performed), the user may be discharged or admitted to the service facility for further service. For example, if the user's condition is not severe, but requires recovery time, the user may be admitted to a service-surgical ("Med/Surg") unit, which is a different service unit from the ED. However, if the user's condition is severe, the user may be admitted to an intensive service (service) unit (ICU) for further service and/or monitoring. In some cases, once the user has been treated and a clinician determines that the user may be discharged, the clinician may issue a discharge order for the user. After the user has received a final consultation and/or finished with any remaining procedures (e.g., completed paperwork, disconnected from an intravenous therapy drip (IV), etc.), the user may be discharged. To facilitate improved user outcomes and improve overall coordination of user service throughout one or more service facilities, an SV system may provide a USP a visual representation of users and/or service resources (e.g., beds, nurses, service equipment, etc.) within service units of a service facility. As discussed further herein, the visual representation may be customized to display different views, depending on the type of USP (e.g., a facility administrator, a floor nurse, an emergency management coordinator, etc.). The visual representation may display various types of data about users and/or service resources, which may be used to monitor and/or predict aspects of a user's service journey while they are treated in one or more service units of the service facility.

In one example, an SV system provides a visual representation of one or more service units of a service facility for use in coordinating user service for one or more users assigned to each service unit. For example, the SV system may receive data input from one or more sources (e.g., an EMR system associated with the service facility, ED discharge system, etc.) that are used to provide a visual representation of users and/or service resources of the service facility. The visual representation may be presented on a graphical user interface (GUI) of a USP. In some examples, the visual representation may be used to visualize census data for each user in one or more service units of the service facility. For example, users may be grouped and visually represented according to various parameters (e.g., by department, by clinician assignment, by priority, etc.). The census data may correspond to any suitable information about the users and/or service resources, including, but not limited to, a resource status (e.g., a clean bed/dirty bed, a workload status of a clinician assigned to a user), a user status (e.g., discharge orders already submitted by clinician, an indicator that a user has special needs), etc. The data that is used to generate the visual representation may be received in substantially real-time (e.g., within 5 seconds, 10 seconds, 30 seconds, 1 minute, or 5 minutes of entry into the system). The data input may include user data of a user, whereby the user data may include various data elements (e.g., past service history, user demographics, vital statistics, medications, lab orders, radiology and/or pathology reports, etc.). The user data may be input into a classification model of the SV system, whereby the classification model may classify the user according to a condition (e.g., type of illness, special needs) and/or service status of the user (e.g., waiting for admission, ready for discharge). Based on the user's classification, the SV system may assign the user to a user group. For example, users who have a certain type of special need (e.g., requiring helicopter transport in the event of an emergency) may be grouped into a particular user group. In some examples, the particular user group may be associated with a distinguishing (e.g., unique) visual indicator (e.g., a color-filled circle, a square shape, a pattern within a circle, a circle with a colored outline, etc.). Another data input may also include resource data corresponding to a status of resources (e.g., a location of resources (e.g., within a particular service unit), a type of resources, etc.). Similar to the user data, one or more resources that have a common resource status (e.g., a clean bed, a dirty bed) may be assigned to the same resource group. The resource group may also have a distinguishing indicator. Based at least in part on the assigned user groups and the assigned resource groups, the SV system may generate a visual representation of at least a portion of a service unit of the service facility. For example, the SV system may generate a visual representation of users in a branch of the ED who already have discharge orders and are awaiting discharge. In another example, the visual representation may also include an indication of which beds within the branch are clean or dirty. It should be understood that the visual representation may correspond to any suitable representation (e.g., a hierarchical representation displaying one or more service units within a service unit). The SV system may then provide the visual representation for presentation on a user device of a USP for use in coordinating service (e.g., among users and/or resources of the one or more service units represented). For example, a USP determine that one or more beds need to be cleaned so that users in a waiting room may be checked in and assigned a bed. In another example, the USP may determine that a clinician should be reassigned to a particular service unit, to accelerate the user discharge process for users already scheduled for discharge.

In another example, the SV system may provide recommendations to a USP for improving user throughput within a service facility. For example, the SV system may be associated with a prediction model (also known as a "classification" model, which may employ one or more machine learning (ML) algorithms) that is trained to predict a condition and/or service status of a user. The SV system may receive user data for a user (of a plurality of users) of a service facility, and then input the user data into the prediction model. The service facility may include a plurality of service units. The prediction model may then output a classification for the user that is associated with at least one of: (1) a predicted admission to a first service unit (e.g., the ICU) of the plurality of service units, or (2) a predicted discharge (e.g., within 24 hours) from a second service unit (e.g., the ED) of the plurality of service units. The prediction model may generate a classification for each user and then the SV system may assign users to user groups based on common classifications (e.g., a predicted discharge), similar to as described above. The SV system may then generate recommendations for one or more users, whereby a recommendation may be associated with at least one of: (1) servicing a first service resource (e.g., a bed) associated with a third service unit, or (2) procuring a second service resource (e.g., a nurse) associated with a fourth service unit. In some examples, the recommendation may be generated based at least in part on the classifications for the plurality of users. The SV system may then provide the recommendations for presentation on a user device of a USP for use in coordinating user service. In some examples, the recommendations may be presented based on the assigned user groups. For example, the SV system may recommend that users in the ED who are classified as being predicted to be discharged within the next 2 hours should be assigned to the same user group. The SV system may further determine that users in this user group should receive an elevated priority for being consulted by a clinician, to accelerate the discharge process. This may be recommended because the system also determines that the ED waiting room has a large number of people waiting for a bed. The SV system may then provide a customized view (e.g., including visual indicators corresponding to the assigned user group) that includes recommendations for improving user throughput and reducing chokepoints as users are treated within one or more service units of the service facility. It should be understood that, as described further herein, this customized view may be one of multiple possible customized views. Each of these customized views may be generated by the SV system using different (or similar) data inputs, and may present different types of visual presentations that are respectively customized for a particular user. For example, a facility floor manager responsible for assigning nurses to users may utilize a different view than a facility administrator who is planning for emergency evacuation procedures. Although each customized view may show different types of data (e.g., predicted user admission, predicted user discharge, etc.), the SV system may standardize a presentation of elements within each visual presentation (e.g., using similar elements to depict service units, users, and or service resources). It should also be understood that, as described herein, recommendations may be presented in any suitable way (e.g., a graphical depiction, text, etc.). Recommendations for user assignments (and/or re-assignments) between service units may also span not only a single service facility, but also across service facilities (e.g., within an enterprise). For example, the system may recommend that a user be transferred to another service facility where there are open beds available.

In another example, the SV system may provide recommendations for assigning a user to a service unit of a service facility. For example, a user may be checked in to an ED of a service facility. Typically, if the user's condition warrants the user being admitted as an inpatient, the user may be admitted to a Med/Surg service unit for service and recovery. However, the user may present certain symptoms and/or conditions that may be latent, and/or a future severity of the condition may not be easily ascertainable by a clinician during an ED visit. In these examples, it may be beneficial to determine as early as possible that the user may benefit from more intensive service (e.g., in an ICU) than they might otherwise receive in the Med/Surg service unit. Here, a prediction model of an SV system may utilize user data to predict a future condition or service status of the user. The user may be assigned to a user group (e.g., users likely to require intensive service), and the SV system may further determine a recommendation associated with assigning the user to another service unit of the service facility (e.g., the ICU). In one example, a customized recommendation may be provided for each user of the user group (e.g., depending on other characteristics (e.g., special needs) of each user). The recommendations may be provided for presentation on a user device of a USP to be used for identifying which users are candidates for being reassigned to another service unit (e.g., the ICU). By recommending that the user be assigned to a more appropriate service unit (e.g., ICU) earlier in the user's journey (e.g., rather than having to be transferred later from the Med/Surg unit to the ICU), an SV system may help to improve user outcomes.

In another example, the SV system may predict bed availability within a service unit of a service facility. For example, the SV system may receive a plurality of images from a camera that identifies a bed cleaning process of a bed within the service unit. For example, the bed cleaning process may correspond to a service resource (e.g., an Environmental Services (EVS) technician) involved in cleaning a bed (e.g., changing sheets, wiping the bed with disinfectants, etc.). The bed cleaning process may be performed within a portion of the service unit (e.g., a room of the ED), whereby the portion is within a field of view of the camera. The SV system may determine a status of the bed based at least in part on the plurality of images. For example, the SV system may recognize at least one of: (1) the EVS technician (e.g., via facial recognition), (2) a movement of the EVS technician within the portion of the service unit, or (3) a duration of time that the EVS technician is detected or not detected within the portion of the service unit. Based on this recognition, the SV system may determine the status of a particular bed (e.g., clean, needs cleaning, occupied, or unoccupied). The SV system may assign the particular bed to a bed group based at least in part on the determined status. The SV system may then generate a visual representation of beds within the assigned bed group (e.g., a white circle indicating that a bed is clean), and then provide that visual representation to a user device of a USP (e.g., a floor nurse manager). The USP may utilize this visual representation to determine, for example, which beds are available for assigning a user to a bed within a particular service unit, and/or which beds need to be cleaned (e.g., to make room for other users in other service units that may be waiting). In at least this way, the SV system may improve upon conventional systems that may rely on human input to determine a bed status, and instead provide real-time feedback to be used for updating the visual representation provided to the USP. This may also improve user throughput.

In another example, the SV system may provide recommendations for coordinating assignments of clinicians with users. For example, one or more users may be assigned to a service unit of a service facility, and the service unit may be associated with a clinician (e.g., a floor nurse who is assigned to the one or more users). The SV system may maintain at least one task associated with user service for at least one user (e.g., based on user data received), whereby the task is assigned to the clinician. For example, a user with sepsis may require a specific drug to be administered by the clinician within one hour. A timer may be associated with the task. The timer may correspond to a target timeframe in which the task should be performed. Based at least in part on task timers associated with tasks that are assigned to clinicians, the SV system may be able to identify (e.g., predict) one or more "hot spots." A hot spot may indicate a service unit (e.g., and/or associated clinician) that may require more resources in order to accomplish the work for each task in a timely fashion. For example, the SV system may determine a risk that at least one task may not be performed within the target timeframe (e.g., based on time data for similar previously completed tasks). This may be because the currently assigned nurse is overloaded with many tasks of high priority. The SV system may then classify the service unit as a hot spot based at least in part on the risk. The SV system may then provide a recommendation, for example, that another clinician (e.g., another nurse) be assigned to the service unit, to help mitigate the risk. For example, the SV system may determine that another service unit is at low risk for being a hot spot, and therefore, may recommend that a clinician from the other service unit be reassigned to the hot spot. In this way, the SV system may provide recommendations for effectively allocating resources.

In another example, the SV system may provide recommendations for efficiently scheduling service rooms (e.g., operating rooms) of a service facility. For example, the SV system may receive scheduling data for a user of a service facility. The scheduling data may indicate a clinician (e.g., a surgeon) that will perform a particular procedure (e.g., hip replacement surgery) for the user on a particular day. The service facility may include a plurality of service rooms, and each service room may be a candidate for performing the procedure. Each candidate service room may be associated with a service room profile that indicates a list of procedures scheduled on the particular data for the respective service room (e.g., including the type of procedure, the operating physician, the user identity, etc.). The SV system may input the scheduling data into a prediction model that is trained to predict a duration of the particular procedure. For example, the prediction model may be trained based at least in part on at least one of: (1) durations of previous procedures performed by the clinician that are substantially equivalent to the procedure, or (2) durations of previous procedures performed by other clinicians (e.g., within the service facility or enterprise) that are substantially equivalent to the procedure. Based at least in part on the predicted duration of the particular procedure and the service room profiles of candidate service rooms, the SV system may generate a recommendation for scheduling the procedure in a particular candidate service room. In one example, the recommendation may include at least one of: (1) a room identifier for the particular candidate service room, (2) a start time, or (3) a time duration of the procedure. In this way, the SV system may more efficiently schedule service rooms for procedures.

In another example, the SV system may provide recommendations for coordinating user service based on user readmission data. For example, a user may be assigned to a service unit of a service facility (e.g., the waiting room, the ED, etc.). The SV system may receive user data associated with the user, similar to as described above (e.g., including historical service/admission data, user characteristics such as age, BMI, etc.). A classification model of the SV system may determine a classification for the user based at least in part on the user data. For example, the classification may indicate at least one of: (1) that upon admission for a present condition, the user would be a considered a readmitted user, or (2) a risk of readmission within a predefined time period (e.g., within 7 days, 30 days, etc.) following a discharge of the user from the service facility. In the first case, this classification may be useful for a clinician that is determining how to best prioritize a user waiting to be checked in (e.g., assigning the user to a particular service unit). In the second case, the classification may be useful, for example, to determine that the user should receive proactive follow-up service following discharge, to reduce the likelihood of being readmitted. For example, if a user has a high risk of readmission, a pharmacy may be automatically called, to alert them that a user will need a prescription to be filled. Once the classification is determined, the SV system may assign the user to a user group based at least in part on the classification. The SV system may further determine a recommendation for treating the user. In some cases, the recommendation may be common for all users within the assigned user group. In other cases, the recommendation may be tailored for each user. The SV system may then provide the recommendation (e.g., via a color code, etc.) for presentation on a user device of a USP.

In another example, the SV system may provide recommendations for coordinating user service based on emergency preparedness data. For example, a user may be assigned to a service unit of a service facility (e.g., the waiting room, the ED, etc.). The SV system may receive user data associated with the user. For example, the user data may indicate that a user has certain characteristics for which specialized service may be beneficial (or required). For example, the user may be immobilized and/or otherwise require special service in the event of an emergency that requires evacuation from the service facility. In another example, the user may be connected to an intravenous (IV) drip, and may require special service in the event of an emergency. A classification model of the SV system may classify the user based at least in part on the user data. The classification may be associated with a condition or service status of the user for which specialized service for the user is beneficial during an emergency event. Once the classification is determined, the SV system may assign the user to a user group based at least in part on the classification. The SV system may further determine a recommendation for assigning specialized service for the user. In some cases, the recommendation may be common for all users within the assigned user group. In other cases, the recommendation may be tailored for each user. In one example, the recommendation for specialized service may be associated with at least one of: (1) a resource to be used for treating the user during the emergency event (e.g., a wheelchair, a specialized service bed, a helicopter, ambulance, medication, etc., (2) a navigation path suitable for evacuating the user (e.g., a path within the service facility), or (3) assigning the user to a second service unit of the plurality of service units based at least in part on the suitable navigation path (e.g., a closer room to an exit door). The SV system may then provide the recommendation (e.g., via a color code, etc.) for presentation on a user device of a USP. These recommendations may be useful in a variety of situations, including, but not limited to, an active crime situation, a natural disaster, or a service emergency.

In another example, the SV system may provide recommendations for coordinating user service based on service triggers associated with a user condition. For example, a user may be assigned to a first service unit of a plurality of service units of a service facility. The SV system may receive user data associated with the user. In one example, the user data may indicate that the user has a Foley catheter inserted into their bladder. In another example, the user data may indicate, not only that the user has a Foley catheter inserted, but also that they are presenting with a fever. The SV system may determine an occurrence of one or more service triggers based at least in part on the user data. A service trigger may correspond to a rule (or mechanism) that is activated when one or more conditions are met. For example, using the example above, a trigger may correspond to a rule that activates upon detecting that a user has a Foley catheter inserted. Another trigger be associated with the user presenting with a fever. The SV system may determine a classification for the user based at least in part on the occurrence of one or more service triggers. For example, a user who only triggers on one condition (e.g., catheter inserted) may be classified as being at a first risk (e.g., a lower risk) for a acquiring an infection (e.g., a catheter-associated urinary tract infection (CAUTI)). Meanwhile, a user who triggers on two conditions may be classified as being at a second risk (e.g., a higher risk) for a acquiring an infection (e.g., catheter inserted, and presenting with a fever). It should be understood that any suitable types of triggers and associated risks and/or classifications may be used to perform embodiments described herein. Upon classifying the user, the SV system may assign the user to a user group, similar to as described above. The SV system may then determine a recommendation for treating the user based at least in part on the assigned group. In some examples, the recommendation may be associated with at least one of: (1) a priority for treating the user, (2) a specialized service for the user (e.g., antibiotic service), or (3) assigning the user to a second service unit (e.g., an ICU) of the plurality of service units based at least in part on the specialized service (e.g., to isolate the user from other users and thereby reduce the risk of infection). The SV system may then provide the recommendation (e.g., via a color code, etc.) for presentation on a user device of a USP for use in coordinating user service for the user. In some examples, by presenting these recommendations through a visual representation (e.g., similar to as described above), the SV system may make it easier for USP's to identify and triage at-risk users within service units of a service facility (or division, enterprise, etc.).

In another example, the SV system may provide recommendations for coordinating palliative service for a user. For example, a user may be assigned to a service unit of a plurality of service units of a service facility. The SV system may receive user data associated with the user. The user data may include characteristics of the user, for example, a user's age, a severity of the user's condition, a likelihood of recovery, etc. A classification model of the SV system may be trained to output a classification for the user based at least in part on the user data. In some examples, the classification may be associated with an indication that the user is a candidate for receiving palliative service. Similar to as described above, the SV system may assign the user to a user group based at least in part on the classification. The SV system may also determine a recommendation for treating the user based at least in part on the assigned user group. The recommendation may be associated with at least one of: (1) assigning specialized palliative service to be provided for the user (e.g., in addition to existing curative and/or preventative service), or (2) providing support to an associated kin of the user (e.g., one or more family members, close friends, etc.). The SV system may then provide the recommendation for presentation on a user device of a USP for use in coordinating palliative service for the user and/or the user's kin. As described above, the presentation may include a visual representation that indicates the user group of the user, for more efficient identification and triage of the user.

The present disclosure provides several technical advantages over existing solutions that improve the functioning of the computer system in which a SV system is implemented. For example, conventional techniques do not provide a real-time hierarchical visual representation (e.g., via GUI) of the status and/or activities occurring (e.g., among users, clinicians and/or other resources) within one or more service units within a service facility. These conventional techniques also do not provide one or more customized views that surface user service recommendations within the real-time visual representation, whereby the user service recommendations may be based on one or more predictive models (e.g., a trained neural network, boosted decision tree, etc.). By providing these customized visual representations, embodiments may reduce the amount of time needed to triage and/or determine user service. For example, conventional systems may require multiple messages to be transmitted between clinicians and/or user service coordinators to gather and collate data so that an informed user service decision may be made. In many cases, the data collated may be stale or otherwise irrelevant/inaccurate by the time a decision is made. Embodiments of the present disclosure may lead to quicker and more accurate decisions, in part by reducing the number of messages that are transmitted between clinicians, and providing the data to decision makers on a real-time basis. This may, in turn, lead to better communication with the user and increased user satisfaction. By reducing the total number of messages required per user, multiplied over a large number of users in a service system, this may improve network efficiency (e.g., increasing available bandwidth) and increase computing resources available to the computer system. This may also lead to improved memory utilization because the number of messages required for processing and storage is reduced. Additionally, because the system and associated prediction models are trained using the largest and most relevant datasets available (i.e., those maintained in the world's largest service data warehouse), the predictions made using the described system (e.g., classifications and/or resulting triggers) are more precise and more accurate than those made by prior art systems trained using smaller datasets. For example, these datasets may be drawn from user data including a large corpus of user records, clinician notes, blood samples, etc. Additionally, because of the higher quality of the prediction models, fewer computing resources are required to make the predictions as would be required using conventional techniques.

Referring first to FIG. 1, a block diagram of an example of an interaction system 100 is illustrated. Generally, in interaction system 100, data can be generated at one or more system components 102 and/or user devices 104. Management engine 106 can manage the flow of communications within interaction system. Transformative processing engine 108 can receive, intercept, track, integrate, process, and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102, and/or data in a corresponding communication received from a user device.

As another example, a user device 104 can be configured to detect input received at an interface of the device. The input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect input requesting particular data, to generate a request communication (e.g., to be sent to transformative processing engine), to receive the requested data and/or to present the received data.

The depicted engines, devices and/or components can communicate over one or more networks. A network of one or more networks can include a wired network (e.g., fiber, Ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or focus. Exemplary types of facilities include server farm facilities, web-server facilities, data-storage facilities, telecommunication facilities, service facilities, and/or operational facilities. For example, a first facility may include a structure at a first location at which one or more resources (e.g., computational resources, equipment resources, laboratory resources, and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another example, different facilities may include resources of similar or same types but may vary in terms of, for example, accessibility, location, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing, and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client, or receiving a service from the client.

In some examples, one or more components 102 and one or more user devices 104 may communicate with transformative processing engine 108 and management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., management engine 106, an entity device, and/or a user device) and/or locally or remotely stored. In some examples, transformative processing engine 108 receives data in a particular format (e.g., the HL7 format) or conforming to any other suitable format and/or is configured to transform received data to conform to the particular format.

One or more components 102 of facility 110 can include and/or has access to a local or remote memory for storing generated data. In some examples, the data is stored by one or more servers local to facility 110. The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from a component (or facility), the record service can identify a corresponding record and update the record to include the data (or processed version thereof). In some examples, the record service provides data to transformative processing engine 108.

Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private, and/or proprietary network or protocols. The use of one or more private and/or proprietary protocols can promote secure transfer of data.

Figure 2:
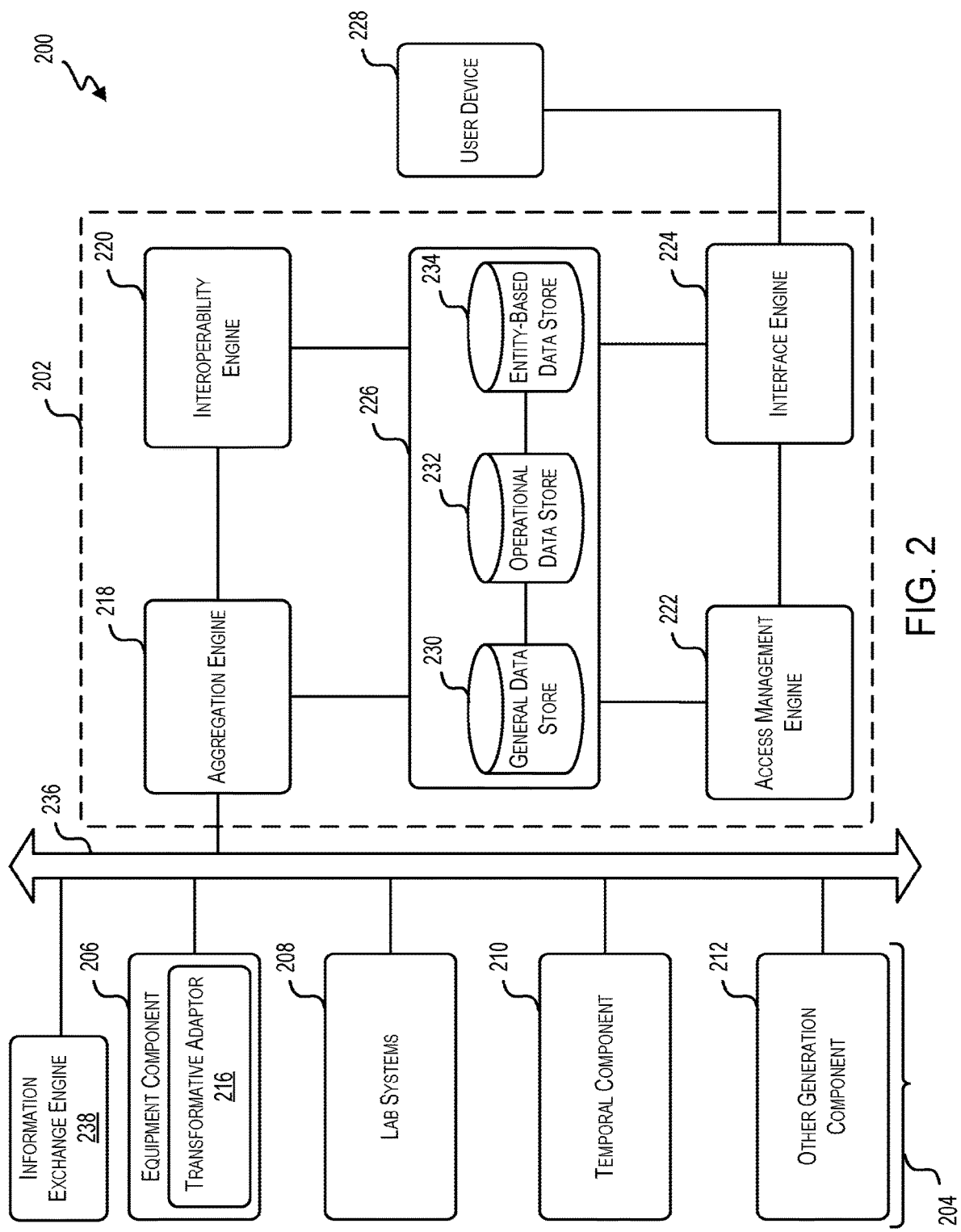
FIG. 2 is an example block diagram illustrating an interaction system in which techniques relating to coordinating user service based on user and/or resource classifications may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 include an equipment component 206, a lab systems component 208, a temporal component 210, and other generation component 212. One or more generation components 204 are examples of one or more components 102 discussed with reference to FIG. 1. In some examples, the data may pass to the transformative processing engine 202 via an information exchange service bus 236 (e.g., an enterprise service bus). In some examples, only a portion of the is passed via the information exchange service bus 236, while other portions are passed directly to the transformative processing engine 202 without first passing over the information exchange service bus 236.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design-making large amounts of data, in many different originating formats available to various types of users, via one or more interfaces. At least a portion of the data generated by the generation components 204 may be provided to the transformative processing engine 202. In some examples, each generation component 204 includes an agent that executes on the generation components 204 and determines which data to send to the transformative processing engine 202 and other engines described herein. In some examples, the generation components 204 provide data to the transformative processing engine 202 via a messaging bus (e.g., an information exchange service bus 236). The messaging bus, which may be included in the transformative processing engine 202 or separate, is able to see data that moves throughout the interaction system 200. The information exchange service bus 236 also includes a subscription registry that can be used to manage subscriptions to the information exchange service bus 236 for certain data (e.g., data having certain characteristics). The information exchange service bus 236 may send and/or direct data to certain other entities when appropriate as indicated by subscription records in the registry.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Temporal component 210 may include any suitable computing devices used with respect to interaction system 200. For example, temporal component 210 can be configured to allocate a resource to a particular entity during a particular temporal window. Temporal component 210 can monitor a schedule for the resource and can identify one or more available temporal windows that may be secured by a particular entity. Upon receiving an indication, temporal component 210 may update a schedule of a resource to reflect that a particular temporal window is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the location and other details about the component or the user device. In some examples, the component and the user device may include global positioning chips that are configured to determine a geolocation.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine, and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, and the like. Access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

As described herein, an information exchange engine 238 shares a network connection with the information exchange service bus 236. The information exchange engine 238 is configured to monitor data (e.g., messages) that is passed over the information exchange service bus 236 and, from the monitored data, select certain portions to provide to one or more authorized user devices. The information exchange engine 238 is also configured to route inbound messages and route outbound messages, as described herein. The information exchange engine 238 is also configured to generate customized messages based on dependent user data.

Figure 3:
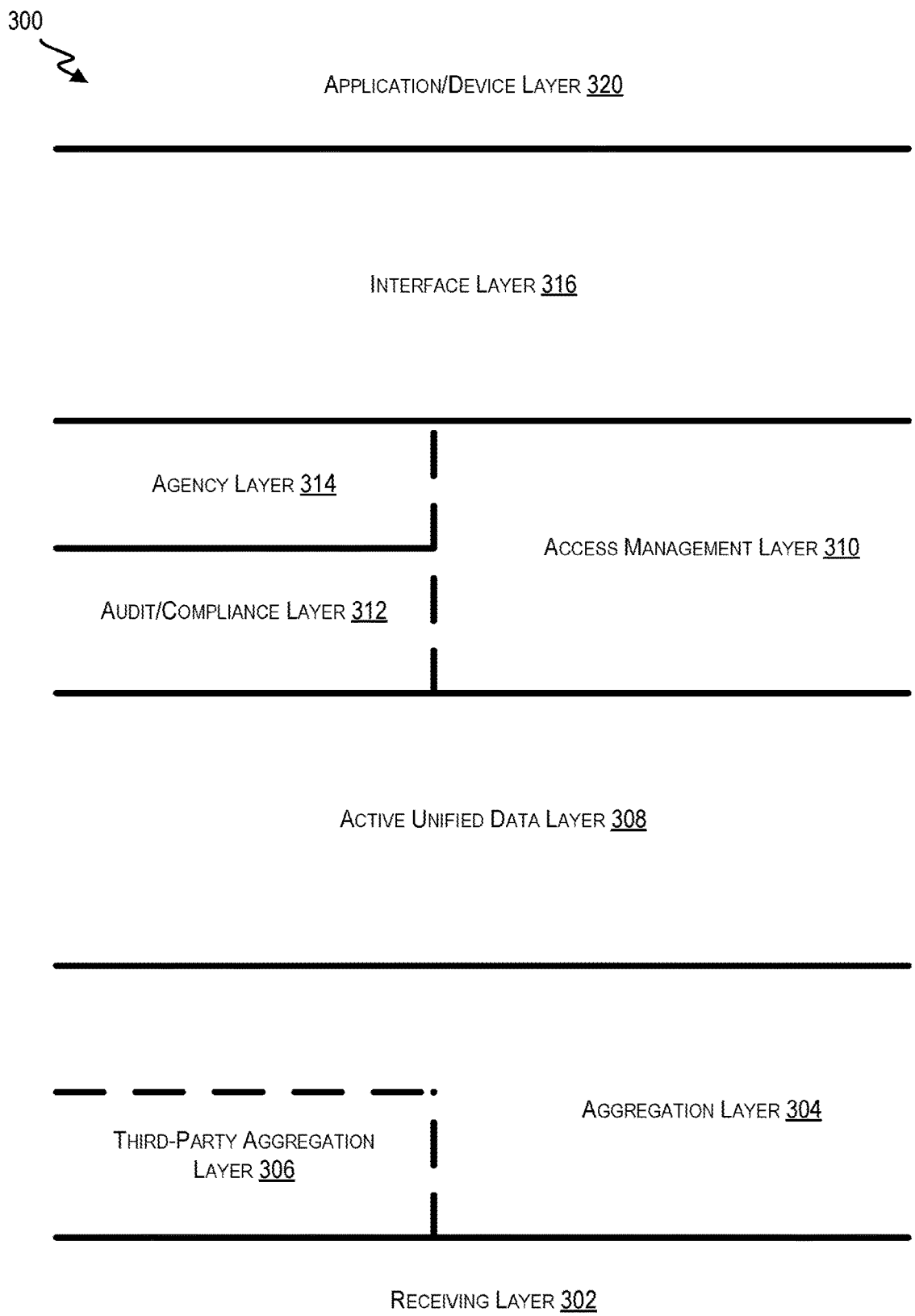
FIG. 3 is an example schematic model illustrating a network communication model in which techniques relating to coordinating user service based on user and/or resource classifications may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum, or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties.

Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
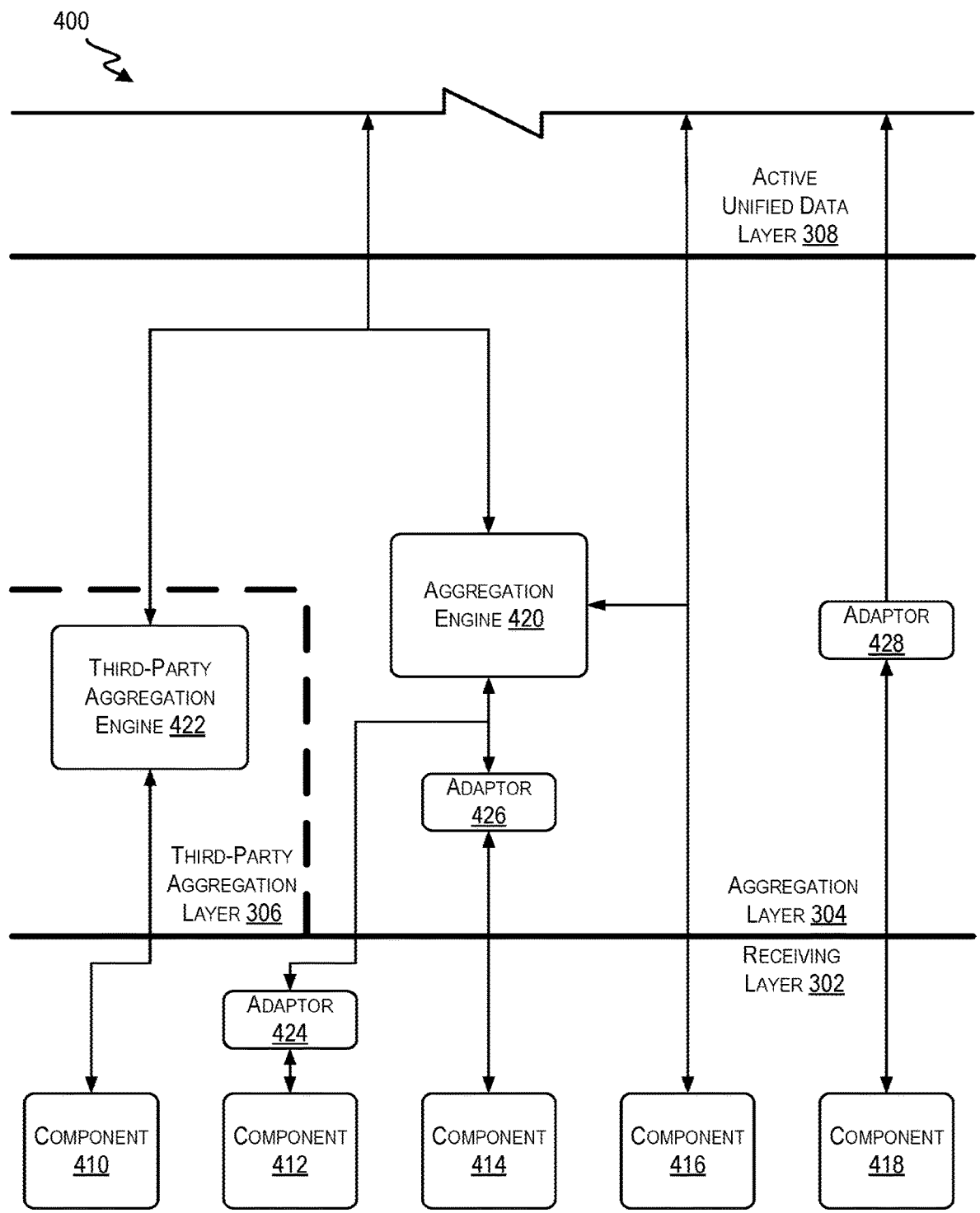
FIG. 4 is an example schematic model illustrating an aspect of the network communication model of FIG. 3 in more detail.

Turning next to FIG. 4, a diagram 400 is shown that depicts a portion of architecture stack 300 according to at least one example. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

The diagram 400 also includes the information exchange service bus 236 and the information exchange engine 238. As introduced herein, messages passing through the aggregation layer 304 can pass over the information exchange service bus 236. In this manner, the information exchange engine 238 can access the messages, route the messages, and/or customize the messages.

Figure 5:
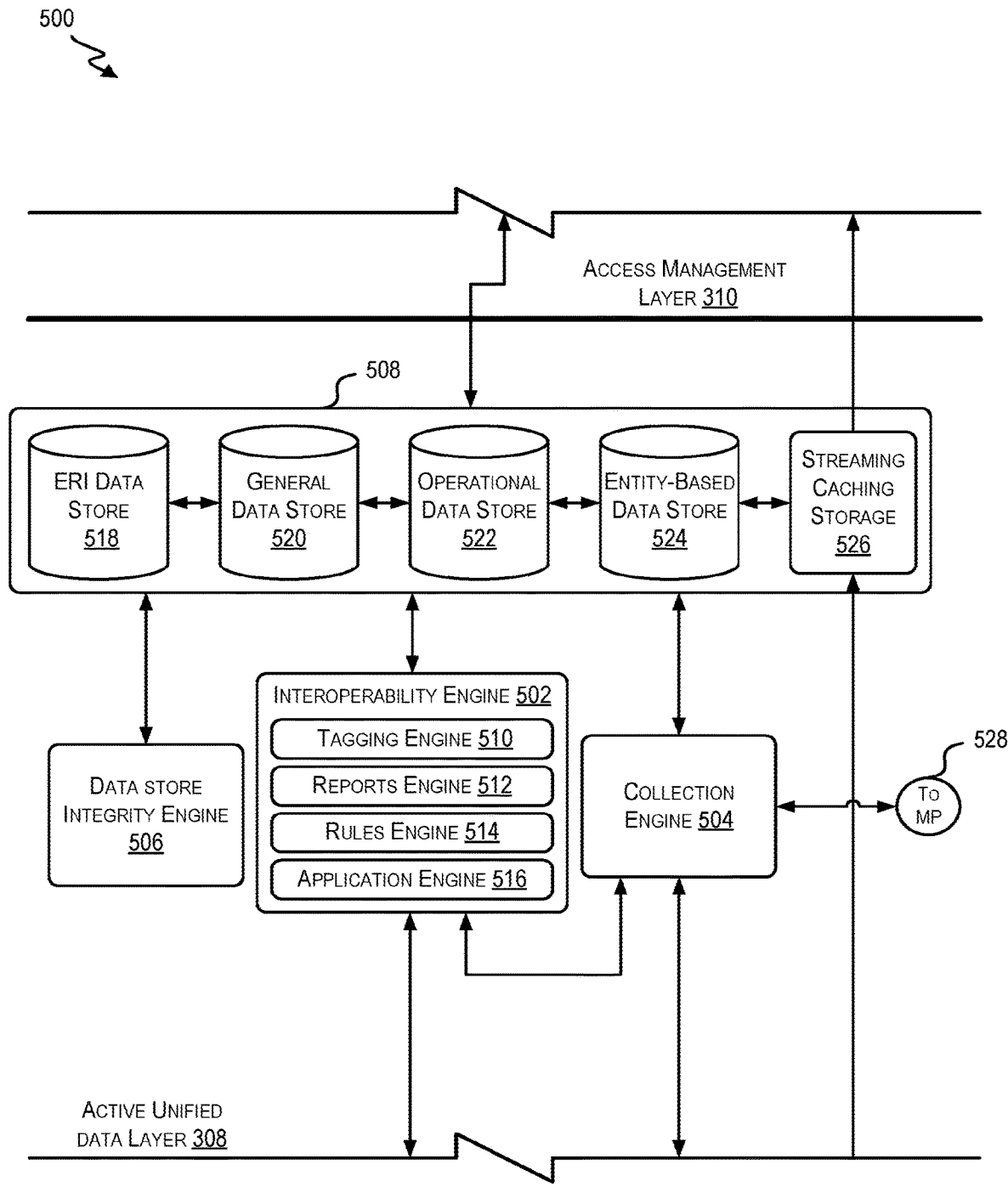
FIG. 5 is an example schematic model illustrating an aspect of the network communication model of FIG. 3 in more detail.

Referring next to FIG. 5, a diagram 500 is shown that depicts a portion of architecture stack 300 according to at least one example. In particular, diagram 500 includes active unified data layer 308 and a portion of access management layer 310. Active unified data layer 308, as illustrated in diagram 500, includes an interoperability engine 502 (e.g., interoperability engine 220), a collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304.

In some examples, the table also includes information for tracking the progress of the message from an origination node to a destination node. For example, typically when a message (e.g., any communication of data) is first received by transformative processing engine 108 (e.g., interoperability engine 502), management engine 106 (e.g., collection engine 504 of management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to management engine 106 that it saw the message. In this manner, management engine 106 may track messages from end-to-end for the life of the message.

In one example, the messages are requests. The requests may be generated based om user input at one of the components. The requests may be received by transformative processing engine 108 and integrated into the system. In some examples, management engine 106 may be notified that the requests have been received and may therefore be configured to generate message IDs for each request. These message IDs may then be associated with each of the requests. As the requests continue to move throughout the interaction system (e.g., away from transformative processing engine 108), management engine 106 may track their movement using the message IDs. If one of the requests does not arrive at its destination, management engine 106 may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, management engine 106 (e.g., collection engine 504 of management engine 106) may receive the message and/or message identifier directly from one of components 410-418. For example, one of components 410-416 may be configured to generate the unique message identifier and/or communicate directly with management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, collection engine 504 provides unique message identifiers to other elements of the interaction system to monitor the messages as they move throughout the interaction system. Collection engine 504 also provides a portion of the unique message identifiers to a management platform (indicated by a circle 528) for further analysis of the message identifiers. Such analyses may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("ERI data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within ERI record data store 518 is retained data. In some examples, the information within ERI record data store 518 is organized according to entity identifying information. Thus, ERI record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. In some examples, the operational data store 522 includes data pertaining to decision making as discussed herein and other data typically used.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
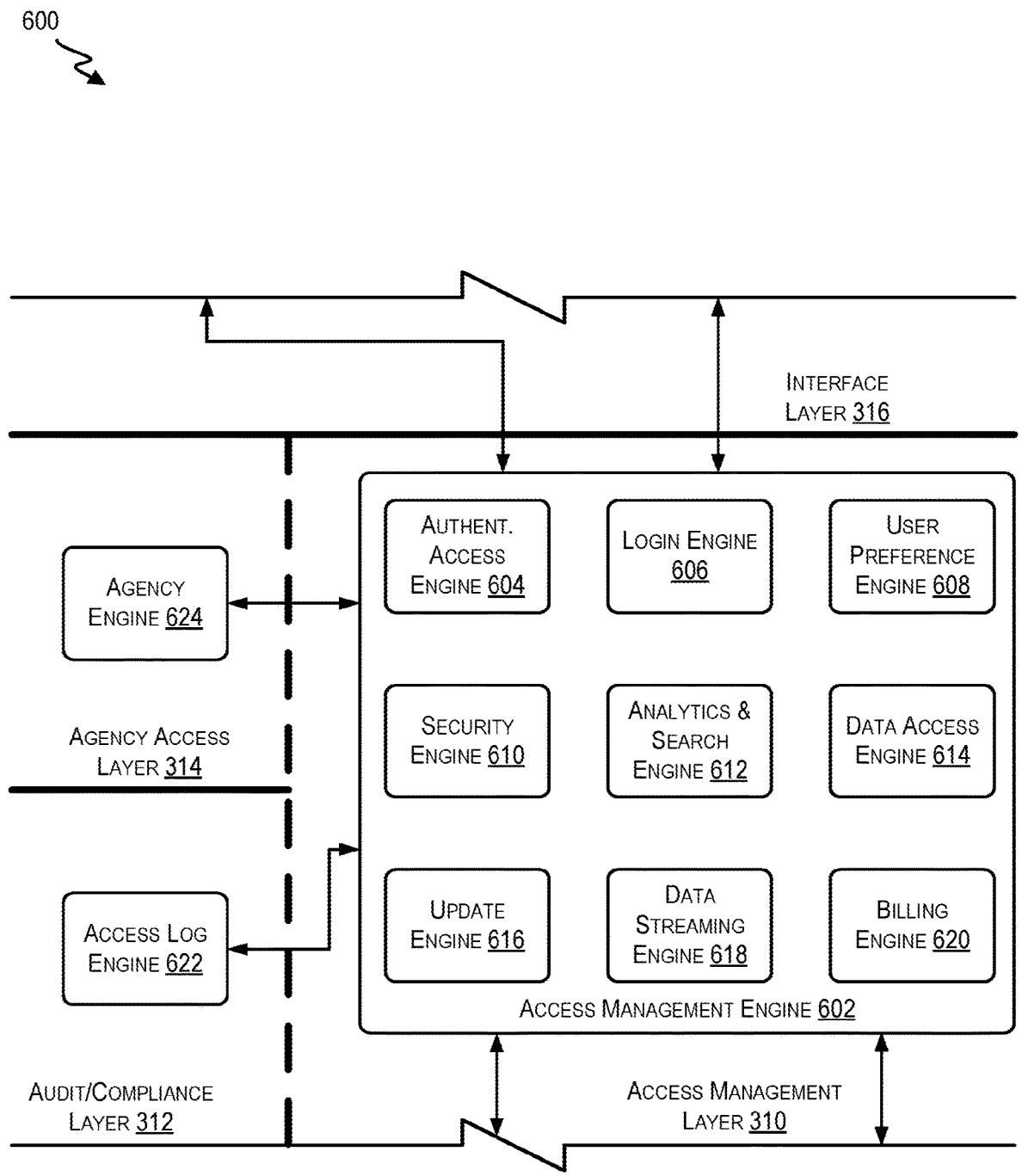
FIG. 6 is an example schematic model illustrating an aspect of the network communication model of FIG. 3 in more detail.

FIG. 6 shows a diagram 600 which depicts a portion of architecture stack 300 according to at least one example. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions, and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. In some examples, agency engine 624 may be used to track one or more performance indicators identified by a government agency and/or to provide report instances of defined types of events. In some examples, a university is an agency that uses agency engine 624 to collect data pertaining to one or more studies. Agency engine 624 can collect the pertinent data, potentially format and/or analyze the data, and facilitate transmission of the data to the appropriate agency.

Figure 7:
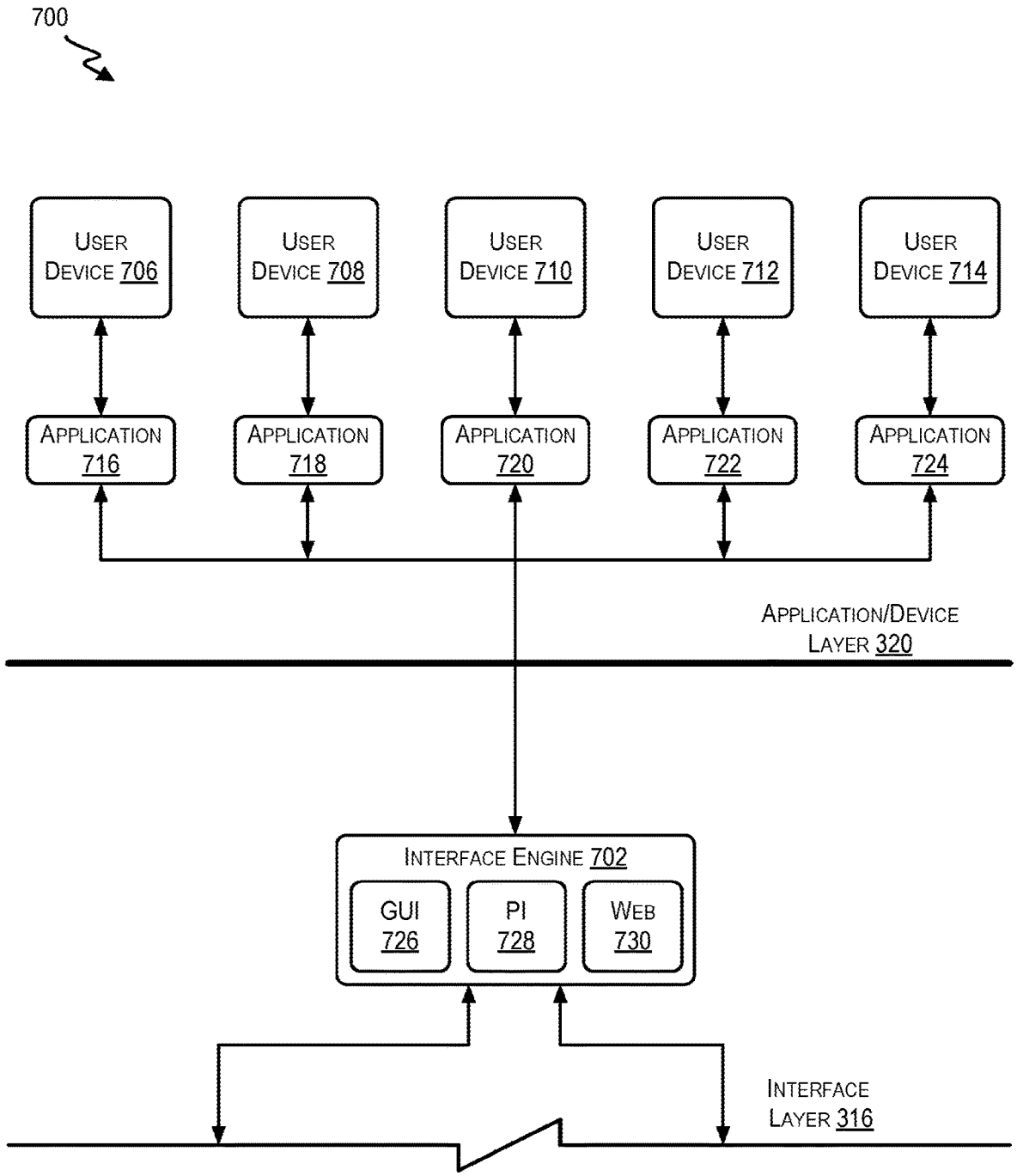
FIG. 7 is an example schematic model illustrating an aspect of the network communication model of FIG. 3 in more detail.

FIG. 7 shows a diagram 700 which depicts a portion of architecture stack 300 according to at least one example. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 706-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for a particular entity. In some examples, application 720 may present different data depending on a focus of the entity and protected information associated with the entity. In this manner, application 720 adapts and automatically adjusts depending on the context in which the entity is using the application. Application 720 may be configured to receive input, adjust presentations, present unprompted alerts, adjust display of content, move more relevant content to the foreground, move less relevant content to the background, and/or populate forms for the entity.

In another example, application 722 may be specific for nurses or types of nurses. In this example, application 722 may include dashboards, widgets, windows, icons, and the like that are customized to individual nurses. Similar to the example discussed above pertaining to the user, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data. In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
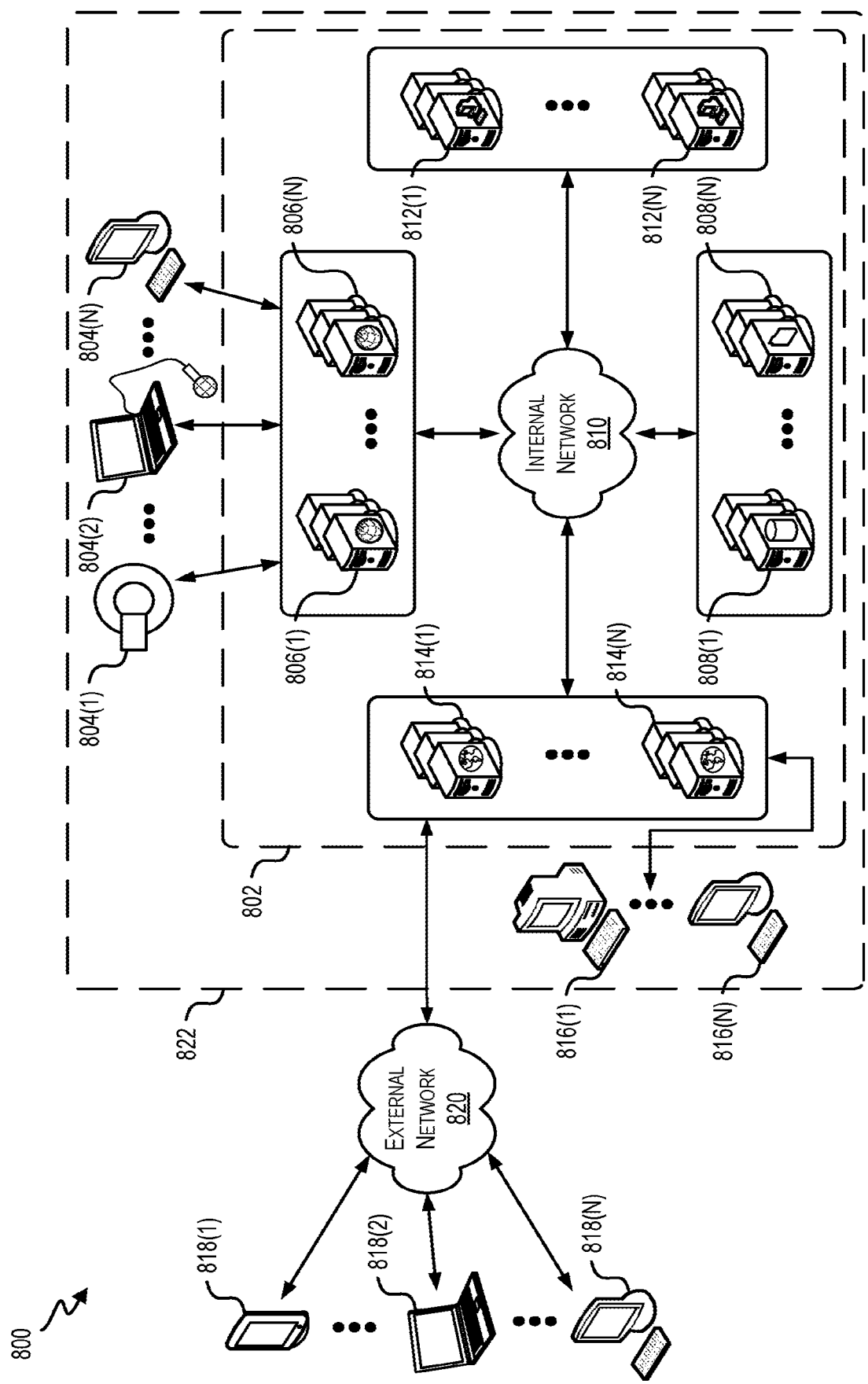
FIG. 8 is an example schematic architecture illustrating an interaction system in which techniques relating to coordinating user service based on user and/or resource classifications may be implemented, according to at least one example.

Turning now to FIG. 8, an interaction system 800 is shown according to at least one example. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

Figure 9:
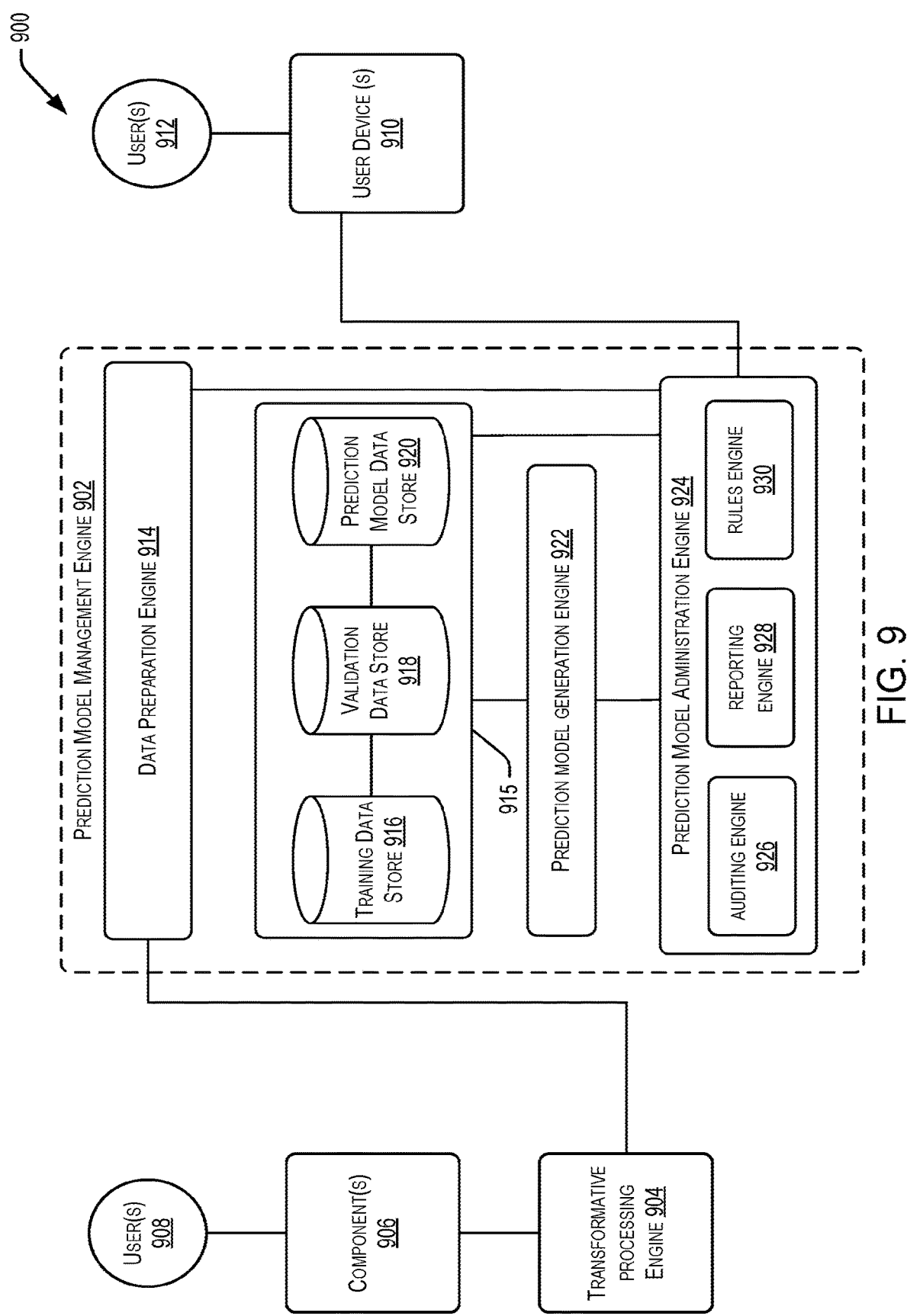
FIG. 9 is an example architecture illustrating a system in which techniques relating to coordinating user service based on user and/or resource classifications may be implemented, according to at least one example.

Turning now to FIG. 9, a block diagram of an example of a service provider prediction system 900 is shown, according to at least one example. In some examples, the service provider prediction system 900 may be a component of (or connected to) a service management system (e.g., a service provider network) that is affiliated with a service organization. The service organization may include one or more service (e.g., service) facilities, which may each transmit data to the service management system. The service management system, as described in the systems and methods depicted in later figures, may include one or more other components as described in reference to FIGS. 1-8, described herein. For example, the service provider prediction system 900 of FIG. 9 includes a prediction model management engine 902. The service provider prediction system 900 further includes a transformative processing enginetransformative processing engine 904. The transformative processing enginetransformative processing engine 904 is an example of the transformative processing enginetransformative processing engine 108 discussed with reference to FIG. 1. The service provider prediction system 900 also includes one or more generation components 906, which may be similar to the one or more generation components 204 discussed with reference to FIG. 2. In some examples, the generation components 906 may receive data input from one or more users 908 (e.g., clinicians, service technicians, etc.). The service provider prediction system 900 also includes one or more user devices 910 used by users 912 (e.g., user service providers (USP's) such as service nurse consultants, facility administrators, physicians, etc.). The user device(s) 910 may be similar to user device 228 of FIG. 2 and/or user device 104 of FIG. 1. The transformative processing enginetransformative processing engine 904 and the user device(s) 910 may communicate with the prediction model management engine 902 using any suitable network connectivity device, as described earlier. It should be understood that one or more of the components described in reference to FIG. 9 may be implemented on the same device or different devices. For example, as described herein, a prediction model (which may also be known as a "classifier," "classification model," and/or "segmentation model) may be trained on one device and the later executed on another device.

In some examples, the transformative processing enginetransformative processing engine 904 may receive service-related data generated by the generation components 906 (e.g., a lab systems component 208, service equipment component 206, service component 212, etc.). The service-related data (e.g., lab results) may be collected from one or more sources. For example, the service-related data may be connected from different service facilities of a service organization (e.g., from one or more Electronic Medical Record (EMR) systems respectively associated with different service facilities). In another example, the service-related data could be collected from one or more entities affiliated with the different service facilities (e.g., insurance companies, contractors, other service providers, etc.). The data can further include an identification of a user and/or other user-pertinent information (e.g., user service records, service history, genetic data, biometric data, actual or suspected diagnosis, and/or demographic information). The transformative processing enginetransformative processing engine 904 may receive the data in any suitable format and may transform the data into a format that is suitable for reception by the prediction model management engine 902. For example, the prediction model management engine 902 may access the transformed data via the interface engine 224 of the transformative processing enginetransformative processing engine 904. Data may be received by the prediction model management engine 902 using any suitable cadence, including being received in substantially real-time (e.g., once a day, once an hour, once every minute, every few seconds, etc.). The data may be received (directly or indirectly) via either push or pull technology. In some examples, newly received data may be used to update (e.g., retrain) one or more prediction models of the prediction model management engine 902.

The prediction model management engine 902 includes a data preparation engine 914, a prediction model generation engine 922, a prediction model administration engine 924, and a data store 915. Generally, the data preparation engine 914 is configured to receive and process service-related data from the transformative processing enginetransformative processing engine 904. In some examples the data preparation engine 914 may prepare (e.g., further transform and/or segment) service-related data so that the data may be used to train and validate a prediction model. For example, a data set of service-related data may be split into different subsets by the data preparation engine 914. A training data subset may be generated that is used to train a particular prediction model (e.g., by adjusting the weights between interconnected nodes of a neural network). In some examples, the same (or similar) training data subset may be used to train one or more prediction models utilizing different algorithms, and then a best model may be chosen. A cross-validation subset may also be generated and used to compare the performances of prediction algorithms that were created based on the training set. The cross-validation subset may be a separate set of data that is held back from training the model, and may be used to minimize over-fitting of data (e.g., verifying that any increase in accuracy achieved over the training data set is not due to over fitting). A test subset (e.g., separate from the training subset and cross-validation subset) may also be used to determine how a particular prediction algorithm will perform on new data. In some examples, any suitable segmenting of data received from the transformative processing enginetransformative processing engine 904 may be determined by the data preparation engine 914 for training a prediction model.

As discussed further herein, different types of algorithms (e.g., machine learning algorithms, heuristic algorithms, etc.) may be used to generate prediction models. For example, the prediction model management engine 902 may perform supervised or unsupervised learning to generate prediction models. Typically, especially in the case of supervised learning, as part of the training and validation processes, ground truth labels may be created for data samples and included in (or alongside) one or more of the subsets of data determined by the data preparation engine 914. A ground truth label may refer to information that is provided by direct observation, as opposed to information provided by inference. The ground truth label may be used to measure the accuracy of a training data set's classification. For example, a prediction model may be trained to predict whether a user has a particular condition (e.g., cancer) or status (e.g., likely to be discharged within 24 hours). This prediction may be associated with a present and/or future condition or status. A ground truth label for a particular user may be determined based on an actual observed outcome of the particular user's condition (e.g., a physician confirms that the user has cancer). The training sample for that user may include other data (e.g., blood analysis, biometric data, etc.), which may be used as input to train a prediction model. The prediction that is output by the prediction model may be compared against the ground truth label to determine the accuracy of the prediction, and the comparison results may be used to adjust (e.g., learn) weights and/or parameters of the model accordingly.

In some examples, the data preparation engine 914 may perform semantic tagging and indexing of service-related data (e.g., categorizing data). The data preparation engine 914 may also determine if gaps exist in the pool of data samples, whereby new data should be obtained to increase training coverage. For example, some users' service records may omit an attribute (e.g., Body Mass Index (BMI)) which may be determined to be an important feature for training a particular prediction model. In this case, the data preparation engine 914 may tag these records as requiring attention and transmit a notification to a user device of a system administrator for further action. The data preparation engine 914 may also perform feature engineering, which may involve further transforming and/or extracting the data into a different form that is suitable for training a particular prediction model. For example, the data preparation engine 914 may receive raw data corresponding to pixels of an image (e.g., of a portion of a user's body, a movement of a clinician within a service room). The data preparation engine 914 may then perform one or more operations to analyze the pixels of the image to generate a new feature from the raw data (e.g., a level of skin redness). This new feature may then be used as one of the inputs to a machine learning algorithm (e.g., predicting a type of condition). It should be understood that, in some cases, the data preparation engine 914 may execute a previously generated prediction model in order to engineer a feature that may in turn be used to train another prediction model.

From the data preparation engine 914, data may flow to the data store 915. The data store (and any other data store discussed herein) may include one or more data stores, which may be distributed throughout two or more different locations (e.g., present on different devices, which can include devices of different entities and/or a cloud server). In some examples, the data store 915 includes a training data store 916, a validation data store 918, and a prediction model data store 920. Within each of the data stores 916, 918, and 920 is stored prediction model-related data. In some examples, the structure of one or more of the data stores 916, 918, or 920 may be similar to data store 226. The training data store 916 may contain training data that is used to train a prediction model. The training data may include multiple samples (e.g., based on user service records), and may include ground truth data for each sample. Different sets of training data may be created from the multiple samples (e.g., generating a new training data set on a predetermined time interval). The different training data sets may also be training data subsets that are randomly generated from an overall pool of training data samples, so as to reduce the risk of overfitting. The validation data store 918 may contain training data that is used to validate a prediction model. For example, the validation data store 918 may contain cross-validation and/or test data subsets that are generated from the pool of training data samples. The training data stored in the validation data store 918 may be determined and further curated based at least in part on the composition of the training data sets in the training data store (e.g., generating disjoint sets of data for increased accuracy during validation and testing). The prediction model data store 920 may contain one or more prediction models, which may be either trained or untrained prediction models. The trained prediction models may be generated from the prediction model generation engine 922, discussed further below. The prediction model data store 920 may further include parameters that may be used to train (or update) a prediction model. As a non-limiting example, this may include a type of loss function, a learning rate (e.g., how much to adjust data weights after each training iteration), a subsample size (e.g., indicating how many training samples should be used to train a new model), a number of nodes (e.g., in the case of a neural network), a number of leaves/levels (e.g., in the case of a decision tree), a number of trees (e.g., in the case of a boosted decision tree model), etc.

The prediction model generation engine 922 is configured to generate one or more trained prediction models based at least in part on data from the data store 915. A trained prediction model may be trained to identify which set of one or more categories a new observation (e.g., data from user's service record) belongs. In the case of supervised learning, this may be based on the training set of data containing observations whose category membership is known (e.g., a user who is known to have a particular cancer, which observation may be recorded as a ground truth label). In the case of unsupervised learning, this may be based on grouping data into categories based on some measure of inherent similarity or distance (e.g., clustering). In either type of learning, a trained prediction model may classify an observation as a binary classification (e.g., patent has or does not have a particular condition or service status) or a multiclass classification (e.g., user has probability of having a particular type of condition of several possible types of conditions). In some examples, a trained prediction model may use observation data to output one or more classifications (e.g., assessments) about one or more respective aspects regarding a user's condition (e.g., a likelihood of illness, a type of injury, a severity of injury, etc.) and/or service status (e.g., likely to require admission to an intensive service unit (ICU), likely to be discharged within 24 hours, likely to require readmission within 7 days, etc.). Each of these one or more classifications may be either binary or multiclass classifications. The classifications may include one or more values (e.g., a binary value, or a real number (between 0-1)) that indicate a likelihood of a particular classification being an accurate assessment.

The prediction model generation engine 922 may utilize one or more artificial intelligence techniques to generate a prediction model. As used herein, the term "artificial intelligence" (AI) refers to any suitable computer-implemented artificial intelligence technique including, but not limited to, machine learning (ML) (supervised or unsupervised), natural language processing, machine perception, computer vision, affective computing, statistical learning and classification, Bayesian network models and Kalman filters, reinforcement learning including neural networks (e.g., convolutional neural networks (CNNs), recurrent neural networks (RNNs) such as Long short-term memory (LSTM), etc.), search algorithms and optimization algorithms (including evolutionary computing), heuristic-based algorithms, and automated reasoning. Non-limiting examples of classification algorithms include use of hidden Markov models, decision trees (e.g., boosting decision trees, random forests), support vector machines, etc.

The prediction model administration engine 924 may be utilized to configure the prediction model management engine 902. In some examples, the prediction model administration engine 924 may include an auditing engine 926, a reporting engine 928, and a rules engine 930. The auditing engine 926 may include elements for tracking and monitoring the performance of a prediction model. For example, the auditing engine 926 may be configured (e.g., by a user device 910) to monitor precision and recall values, F1 scores, specificity values (and/or relative statistical data associated with a confusion matrix) for a prediction model over time, as new data is received and input into the prediction model. The reporting engine 928 may include elements for generating one or more reports that are consumable by a user 912 via a user device 910. For example, the reporting engine 928 may execute one or more trained prediction models to generate a report for a one or more users. The report may indicate, for each user, a predicted classification of the user based on current user data (e.g., whether the user has a particular condition or not). The report may include other information (e.g., user demographics, user admission data, etc.), which may assist a user service coordinator in determining a course of service for the user. The reports engine 928 may also output reports on a periodic basis that indicate the performance of one or more prediction models, which may be used to determine whether a model should be retrained with updated data. The rules engine 930 may determine one or more rules for managing aspects of the prediction model management engine. For example, the rules engine 930 may receive input from a user device 910 that is used to configure the data preparation engine (e.g., add a new feature to the list of predictive features being tagged). The rules engine 930 may also be used to configure aspects of the data store 915 (e.g., controls for determining which data should be grouped into a training subset versus a test and/or cross-validation subset, how large a training sample subset should be, etc.). The rules engine 930 may also be used to configure aspects of the prediction model generation engine 922. For example, the rules engine 930 may receive input indicating when a new prediction model should be generated (e.g., on a predetermined cadence, using one or more ML algorithms with particular parameters, etc.). The rules engine 903 may also be used to determine one or more heuristics that may be used as input to the prediction model generation engine 922. For example, one heuristic may indicate that if a user has previously missed more than one scheduled appointment, then they may be more likely to miss future appointments (e.g., and thus may be a good candidate for receiving a reminder call from a USP about future appointments). The heuristics may be determined by a human (e.g., a USP) and input into the rules engine 930, or may be determined automatically(e.g., by the prediction model generation engine 922). For example, the prediction model generation engine 922 may be trained to recognize patterns and make inferences based on those patterns (e.g., if a person misses more than three appointments, they are highly likely to miss future appointments). These inferences may be formulated into rules used to generate a prediction model.

Figure 10:
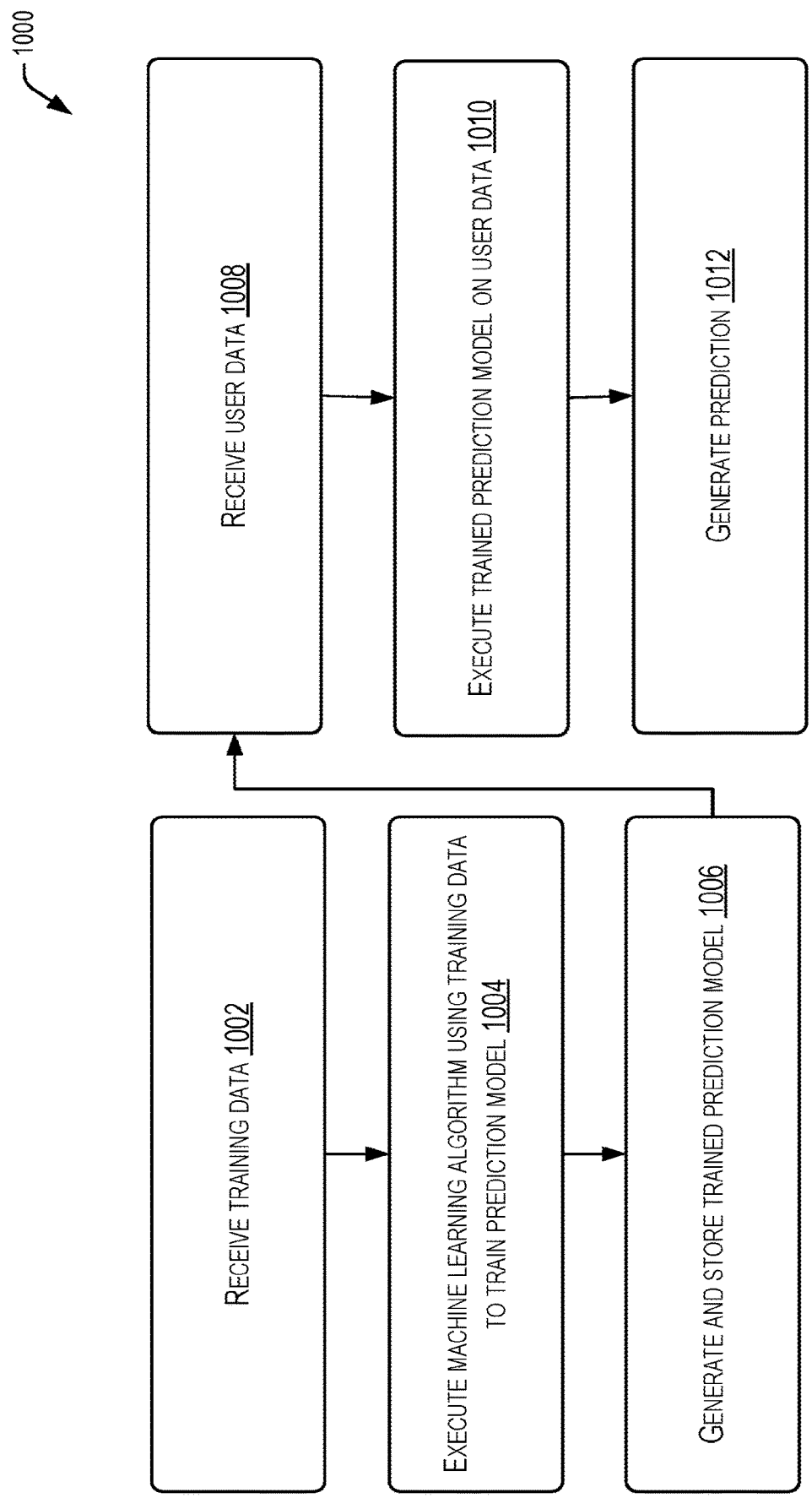
FIG. 10 is an example flowchart illustrating a process for classifying users and/or resources, according to at least one example.

Turning to FIG. 10, an example flow diagram 1000 is depicted for a computer system training a prediction model and executing the trained prediction model. The flow diagram may proceed in two phases: a training phase (blocks 1002-1006) and an execution phase that follows the training phase (blocks 1008-1012). In some embodiments, the computer system that performs the process 1000 may correspond to the service provider prediction system 900 of FIG. 9.

Some or all of the flow 1000 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Additionally, these processes are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

The example flow 1000 may start at block 1002, whereby the system may receive training data. In some examples, the training data may be generated from one or more generation components 204 (e.g., lab systems, service components, service provider systems, etc.). In some examples, the one or more generation components 204 may belong to different service providers (e.g., different service facilities) within a service organization. In some examples, the training data may be received from other sources outside the service organization (e.g., third party entities, government organizations). The training data may be associated with and/or derived from user data of users, for example, derived from user electronic service records. In some examples, a training data sample of the training data may include a plurality of data points that identify characteristics of a user, diagnoses made by service providers, associated service plans for the user made by the providers, associated outcomes of the user based on those service plans, health indicators for the user, laboratory test results (e.g., from blood, urine, and/or other tests), a service status of the user (e.g., recently discharged, completed round three of chemotherapy service, recently was administered a particular medication, etc.), and other suitable information. In some examples, the training data may indicate not only historical service data, corresponding to previous admissions of the user, but may also include present admission data, corresponding to a present admission of the user for a condition. The user data may be received in any suitable form, including structured and/or unstructured user data. Structured data may be data that is organized and formatted in a way that is directly searchable (e.g., in a relational database). Examples of structured user data may include user service records, test results, chart information, etc. Unstructured data may have no (or limited) pre-defined format or organization. Examples of unstructured data may include a clinician's notes, service images, user feedback/correspondence, etc. In general, both structured and unstructured data may be formatted in any suitable way, including, but not limited to, text, audio, video, digital images, and numerical values. The training data may be processed and/or transformed into a suitable form for training a prediction model, for example, by data preparation engine 914. In some examples, this may involve semantically tagging the data, segmenting the data into different subsets (e.g., training sets, cross-validation subsets, testing subsets, etc.), performing feature engineering to generate one or more features for training the prediction model, etc. The training data may be stored in a data store (e.g., data store 915) for future use in training a prediction model.

At block 1004, the system may execute a machine learning algorithm using the training data to train a prediction model. Any suitable machine learning algorithm may be used to train the prediction model, including supervised learning algorithms (e.g., logistic regressions, neural networks), unsupervised learning algorithms (e.g., K-means, Apriori algorithm), and/or reinforcement learning algorithms (e.g., Markov decision processes).

In a first non-limiting example of a supervised learning algorithm, a neural network machine learning algorithm may be used to generate a prediction model using a set of inputs (e.g., training data) that includes one or more features, which in some cases may be measurable properties derived from user data (e.g., blood cell count, blood pressure, age, etc.). Any suitable number of features may be used as input to generate the prediction model. Using this technique, the set of inputs may be used as an input layer and the set of outputs may be used as an output layer. In this technique, the input layer may be connected to the output layer via one or more hidden layers. Each layer may include a set of one or more nodes, whereby each node may represent a piece of information. The generated prediction model may include a number of interconnections between the hidden layers and the input layer and/or output layer (e.g., between nodes of the different layers), each of which may be assigned a numeric weight generated based on a pattern identified between the set of input values and the set of output values. The weight may be tuned (e.g., based on a training dataset), rendering the artificial neural network adaptive to inputs and capable of learning. Generally, the hidden layer(s) allows knowledge about the input nodes of the input layer to be shared among the output nodes of the output layer. To do so, a transformation f is applied to the input nodes through the hidden layer. The artificial neural network may also use a cost function to find an optimal solution (e.g., an optimal transformation function). The optimal solution represents the situation where no solution has a cost less than the cost of the optimal solution. In an example, the cost function includes a mean-squared error function that minimizes the average squared error between an output f (x) (e.g., a prediction, given training data input x) and a target value y (e.g., a ground truth value) over the example pairs (x, y). In some embodiments, a backpropagation algorithm that uses gradient descent to minimize the cost function may be used to train the artificial neural network. In this example, one or more parameters (e.g., which also may be known as "hyperparameters") may be used to administer the training process. For example, these parameters may include determining how many hidden layers of nodes to use between the input layer and the output layer, and how many nodes each layer should use. In this example, the collection of nodes and determined weights (e.g., based on training data) between interconnections of nodes between the different layers may form the trained model. Once the artificial neural network (i.e., prediction model) has been generated, it may be used to predict one or more events (e.g., regarding a user's present and/or future condition and/or service status) upon receiving input (e.g. user data).

In a second non-limiting example, a boosted decision tree technique may be used to generate a prediction model using a set of inputs (e.g., training data) that includes one or more features. Each feature may directly correspond a data point (e.g., BMI, blood pressure, etc.), or be derived from one or more data points, similar to as described earlier. This technique is also a supervised learning method and may utilize a labeled dataset with ground truth data. A pre-trained decision tree may receive a set of input features as input and then split the input data based on those features. For example, a given node in a decision tree may split (e.g., determine an outcome) based on the respective values of one or more input features input to the given node. The selection at each node of what is the next best feature to split on may be performed based at least in part on determining which features maximize information gain and/or to minimize entropy, and may be chosen as part of a (e.g., recursive) learning/training process used to generate the decision tree. The process may be repeated until a stop condition is met (e.g., the process reaches the depth of the tree, no more information gain, etc.). Terminal nodes of the decision tree may represent a class (e.g., segment) label (e.g., the user has a particular condition) or probability (e.g., probability that user has a particular condition), which may correspond to a prediction outcome. In some examples, the outcome may be a continuous variable.

Using a boosted decision tree technique, multiple weak learners (e.g., an ensemble of decision trees) may be combined into a strong classifier. In some examples, each new decision tree may be created iteratively with respect to a distribution (e.g., associated with ground truth data from a training data set), and new trees may be generated based at least in part on previous trees. On each iteration, the new tree's prediction from a data sample may be given a weight relative to its accuracy. In some examples, the ensemble output (from the multiple trees) may be a weighted sum that may be compared against the ground truth. Additionally, after each iteration, each data sample (e.g., including one or more features from the data sample) may also be given a weight based the decision tree's misclassification. In this way, the more often a data sample is misclassified, the more important the data sample (and/or individual features of the data sample) becomes. The process of training the ensemble of decision trees that collectively predict an outcome (i.e., "boosting") may also include minimizing a cost function, which, similar to above, may include a function that measures the distance between the ground truth (y) and an output f(x) (e.g., to minimize the mean-squared error).

Based at least in part on the relative weight of the output of each decision tree in an ensemble and/or the relative weights of data samples, the system may be able to determine a relative importance of features among the set of features that are represented in the ensemble of decision trees (e.g., represented by the positioning of each node within a respective decision tree and the splitting behavior assigned to the node). In some examples, the relative importance among features may represent which feature is likely to result in the most information gain among other features. The system may also be able to determine, based at least in part on the splits determined for each node in the ensemble of trees, classifier decision boundaries. A classifier decision boundary is a decision boundary that partitions an underlying vector space into two sets (e.g., user has the condition, or the user does not have the condition). In some examples, a classifier decision boundary may be determined by an ensemble of classifiers (e.g., a boosted decision tree model) based at least in part on respective values (e.g., a range of values) for one or more features of the plurality of features that are input into the model. In a simplified example, one feature may be age, and another feature may be BMI of a user. For a particular condition, the model may determine that for an age range of 60 years old or more, and a BMI range 15-17, a user would be classified as having a particular condition. In some examples, multiple classifier decision boundaries may be determined from a boosted decision tree model, which may be collectively used as input to determine a final prediction. For example, one classifier decision boundary may determine, from one set of features, that the user is likely to have a condition with a first probability. Another classifier decision boundary may determine, from another set of features, that the user is likely to have (or not have) the condition with a second probability. The first and second probabilities may be combined together to determine a final probability (e.g., prediction). In some examples, this combining process may be represented within the trained boosted decision tree model using ensemble modeling. Similar to the neural network example, one or more parameters may be used to administer the training process. For example, these parameters may include determining a maximum depth of a tree, a maximum number of leaves, a maximum number of features (e.g., from the full set of features) that may be used to build a given tree, a minimum number of samples required to make a new leaf, etc.). Once the (boosted) decision tree prediction model has been generated, it may be used to predict one or more events (e.g., regarding a user's present and/or future condition).

While two possible examples of prediction models were mentioned above, it should be understood that any suitable prediction model may be utilized. Typically, the system will receive training data (e.g., service-related data received from the service organization) that is used to train the prediction model by learning characteristics (e.g., patterns and/or relationships, for example via heuristic algorithms) from the training data and thereby determining properties (e.g., weights) of the model. The system may also determine one or more parameters that may be used in training the model, whereby the parameters may be determined based on the type (e.g., structure) of model chosen (e.g., neural network, decision tree, linear regression, naive Bayes, etc.). In some examples, one or more prediction models may be executed together (e.g., using an ensemble modeling) to obtain better predictive performance. Additionally, in some examples, the output of one prediction model may be used as an input (e.g., as a feature) to another predictive model for generating a prediction. For example, a first prediction model may be a neural network (e.g., a natural language processing (NLP) model) that may be trained to receive as input clinician notes of a report (e.g., a pathology report that includes text-based unstructured data input). In some examples, the NLP model may utilize a word2vec model (e.g., a continuous bag-of-word (CBOW) model or a skip-gram (SG) model). The word2vec model may be used to learn word embeddings in order to determine semantic meanings of words within the clinician notes. The NLP model may be trained similar to as described herein (e.g., based on a corpus of clinicians notes compiled from clinicians throughout the enterprise). The NLP model may be trained to recognize words from the report and predict a likelihood of a particular condition (e.g., breast cancer). The output of the first prediction model may be used as a feature input to a second prediction model (e.g., a boosted decision tree model) that may predict a particular stage of the user condition (e.g., stage 1 breast cancer) with a certain probability score. In yet another example, the trained classification model may be used to generate more than one score for a given set of user data (e.g., utilizing one or more sub-models). Each score may correspond to a level of confidence in a respective classification. It should be understood that different models may be trained using different training data, and may accordingly assign different weights to interconnections between nodes for the respective model. Also, each model may be associated with one or more classification thresholds, as discussed below, which may differ (or be similar) between models.

At block 1006, the system may generate and store the trained prediction model 1006. The generated prediction model may include any suitable data structures utilized from block 1004 to train the prediction model, as well as learned information during the training process (e.g., a meaning assigned to a node, a position of the node within the model, a weight value for a node, etc.). In some examples, the parameters used to train the given prediction model may also be stored, for example, to be later used in updating the model. For example, the prediction model administration engine 924 may perform an audit of the prediction model, and, based on the results of the audit, determine that one or more parameters used to train the model should be adjusted (e.g., increasing the maximum number of leaves). The trained prediction model may be stored in the prediction model store 920.

At block 1008, at a later time following the generation/storage of the prediction model at block 1006, the system may receive user data (e.g., including structured or unstructured user data) for use in generating a prediction about a user (e.g., for classifying (or "segmenting") the user). In some examples, the user data may correspond to current information about a particular user (e.g., service records for a present admission to a service facility). Similar to the training data, the user data may also include a plurality of data points that identify characteristics of the particular user. In this case, however, instead of the data being used to train a prediction model, it will be used as input into the already-trained prediction model for use in generating a prediction about the condition of the user (e.g., for the present admission). In some examples, one or more of the plurality of data points of the user data may correspond to (and/or be used to derive) features by which the prediction model was trained to make predictions.

At block 1010, the system may execute the trained prediction model on the received user data. As described earlier, the system may use the user data for the particular user to extract features that are used as input to the prediction model (e.g., to an input layer of a neural network, root node of a decision tree, etc.).

At block 1012, the system may execute the trained prediction model to generate a prediction about the user (e.g., classifying the user as having a particular condition or service status). In some examples, the prediction may correspond to an assessment about a present condition or potential future condition (or service status) of the user. In some examples, the assessment may include data associated with a plurality of conditions of the user (e.g., multiple injuries on the body). In the case where the prediction corresponds to an assessment about a present condition, the prediction may indicate a likelihood that the user has a particular present condition. In the case where the prediction corresponds to an assessment about a potential future condition, the prediction may indicate a likelihood that the user will develop the potential future condition. As a non-limiting example, a potential future condition may correspond to the existence an illness affecting the user, a severity and/or stage of the illness, a likelihood that another related illness or condition may develop, etc. In some examples, the prediction may correspond to a probability score (e.g., between 0-1). In some examples, and as described herein, the prediction may correspond to a classification of a likely group to which the user belongs (e.g., Stage 1, Stage 2, Stage 3, etc.). For example, the prediction may include a plurality of probabilities that respectively correspond to a likelihood of the user's illness being at a particular stage (e.g., Stage 1=0.23, Stage 2=0.64, Stage 3=0.13). As referenced herein, depending on the context, a "prediction" may be used interchangeably with a "probability score." In some examples, the prediction may be classified based on whether or not a probability score included within the prediction matches (e.g., equals or exceeds) a predefined threshold value (or "classification threshold"). For example, a user with a probability score of at least 80% may be deemed to be "High Risk." In another example, a user with a probability score of at least 80% may be determined to be classified with a particular condition with high confidence. This classification based at least in part on the predefined threshold value may be built into the trained prediction model (e.g., part of the training process), or may be a separate computation that follows the prediction model outputting one or more scores. In some examples, the trained prediction model may output different probability scores respectively for varying degrees of specificity for a particular condition. For example, the trained prediction model may output a score of 85% that corresponds to a confidence level that the user has "cancer." The model may further output a score of 70% that the corresponds to a confidence level that the user has "breast cancer." The model may further output a score of 55% that corresponds to a confidence level that the user has "stage 3 breast cancer." As updated user data is received by the trained prediction model, the respective scores may be updated accordingly.

The systems, processes, and models described with reference to FIGS. 1-10 may be used to implement the techniques described herein with reference to later figures. For example, data communication may be performed within the aggregation layer 304 or the active unified data layer 308. In some examples, messages originate at one of the components 410-418 (e.g., generation components 204) and are streamed to the data store 508. These messages may be intercepted by the collection engine 504 or any other suitable interceptor device and shared with the service visualization (SV) system described herein.

Figure 11:
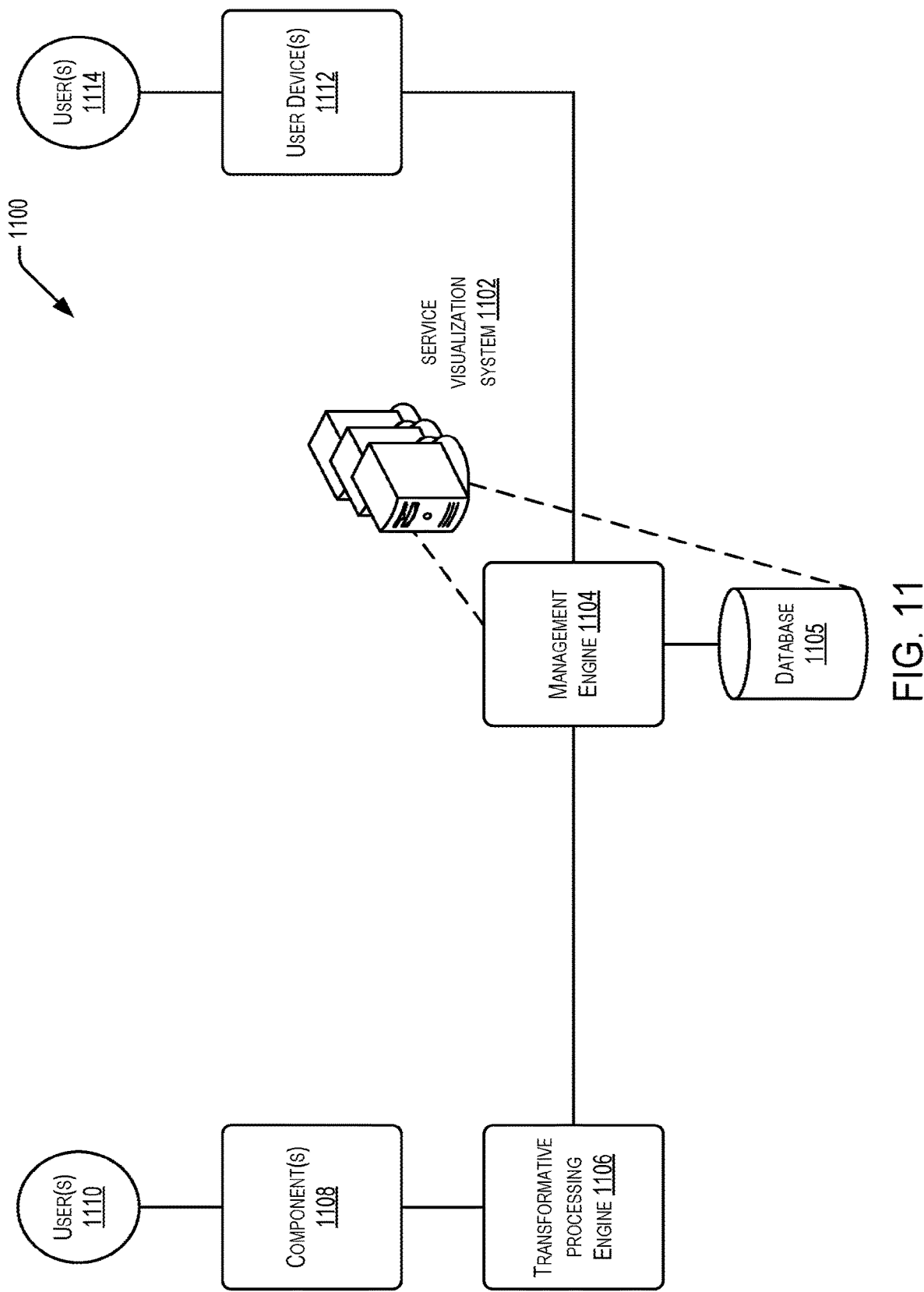
FIG. 11 is an example architecture illustrating a system in which techniques relating to coordinating user service based on user and/or resource classifications may be implemented, according to at least one example.

Turning now to FIG. 11, a service visualization (SV) architecture 1100 is shown, in accordance with at least one example. The SV architecture 1100 may be implemented using elements of the systems, networks, and models of FIGS. 1-10. For example, the SV architecture 1100 may include similar elements as service provider prediction system 900 of FIG. 9. For example, the SV architecture 1100 may include a SV system 1102, which includes a management engine 1104 (e.g., prediction model management engine 902) and a database 1105 (e.g., included within data store 915). The SV architecture 1100 may further include a transformative processing enginetransformative processing engine 1106 (e.g., similar to transformative processing enginetransformative processing engine 202 of FIG. 2). The transformative processing enginetransformative processing engine 1106 may be configured to receive and process data from one or more generation components 1108 (e.g., similar to generation components 204 of FIG. 2), which may in turn receive input from one or more generation users 1110 (e.g., user service providers (USP's), users, and/or other service professionals) to generate service-related data. The SV architecture 1100 may further include one or more user devices 1112 (e.g., similar to user device 228), which may be used to interact with users 1114 (e.g., USP's and/or other service professionals).

In some examples, the SV system 1102 may be configured to receive data from the transformative processing enginetransformative processing engine 1106 and utilize the data to generate one or more predictions (e.g., which may also be described as "classifications" or "segmentations"). These predictions may be associated with any suitable service-related entity (e.g., a user condition, a user service status, a service resource status, etc.). In some examples, these predictions may be used as input for further action/analysis by the SV system 1102 (e.g., recommending a particular service for a user). The transformative processing engine 1106, described in detail herein, can process and store data used by a SV system 1102 to implement the techniques described herein. For example, the management engine 1104 of the SV system 1102 may receive service-related data (e.g., user data, resource data) from the transformative processing engine 1106 and use the data to train one or more prediction models. In one example, user data may include user service records, interaction data (e.g., between the user and a USP), feedback data, outcome data, and the like. The user data may be representative of users within a population. At a later time, the management engine 1104 may receive current user data (e.g., for a currently admitted user or a user waiting for check-in), which is input into one of the trained prediction models. The trained prediction model may then output a prediction (e.g., a score for a user corresponding to a level of confidence of a classification of the user). The SV system 1102 may further analyze the prediction to determine one or more recommendations for treating the user. In some examples, the predictions (and/or the resulting recommendations based on the predictions) may be displayed for visual presentation on a user device 1112 of a user 1114. The visual presentation may be in any suitable form. For example, the visual presentation may present the classifications (e.g., predictions) and/or recommendations using text, images, shapes, colors, etc.

The database 1105 is accessible by the management engine 1104, and may be similar to (or connected to) data store 915 of FIG. 9 and/or data store 226 of FIG. 2. The database 1105 may include data from a transformative processing engine 1106, and the management engine 1104 may use such data to generate a prediction. For example, the data may include training data and testing data (e.g., to test the prediction models). The database 1105 can be distributed or otherwise made available to multiple users. In some examples, the database 1105 may be centralized. In other examples, the database 1105 may be decentralized (e.g., a database per division or per service facility). In some examples, the database 1105 may store multiple prediction models. It should be understood that, although in the embodiments described herein, multiple types of prediction models may be described, the functions performed by the one or more prediction models may also be performed within a single prediction model or any suitable combination of models, as described in reference to FIGS. 9 and 10. The prediction models, as described herein, can be initialized using data mined from the data store of the transformative processing engine 1106.

The SV system 1102 may be affiliated with a service management system of a service organization (e.g., enterprise), whereby the service management system may also be implemented using similar elements of the systems, networks, and models of FIGS. 1-10. For example, the service management system may be a centralized system for performing techniques described herein. The centralized system may aggregate service-related data (e.g., via the transformative processing engine 1106) from a plurality of affiliated service facilities of the service organization into a data store (e.g., data store 226) for further processing by the SV system 1102. For example, individual service facilities of the plurality of affiliated service facilities of the service organization may, respectively, be associated with one or more data stores (e.g., EMR systems, emergency department discharge systems, third-party provider systems, etc.). Data from one or more of these data stores may be aggregated and processed by the centralized system.

Examples described herein provide different systems and methods for supporting a USP (e.g., a nurse, user navigator, user navigation coordinator, physician, administrator, facility executive) in the process of coordinating user service. The systems and methods provided are suitable to support a USP in a variety of environments and contexts. For example, some environments may involve coordinating user service across an entire enterprise or a division of the enterprise that contains multiple service facilities. Another environment involves coordinating service among users in a single service facility, and/or users within a particular service unit (e.g., emergency department) within the single service facility. In another example of a particular context, the system may help the USP coordinate service for a user at the time of admission to a service facility, while the user is receiving service during their stay, or post-discharge. These various environments and contexts will be discussed herein below.

Figure 12:
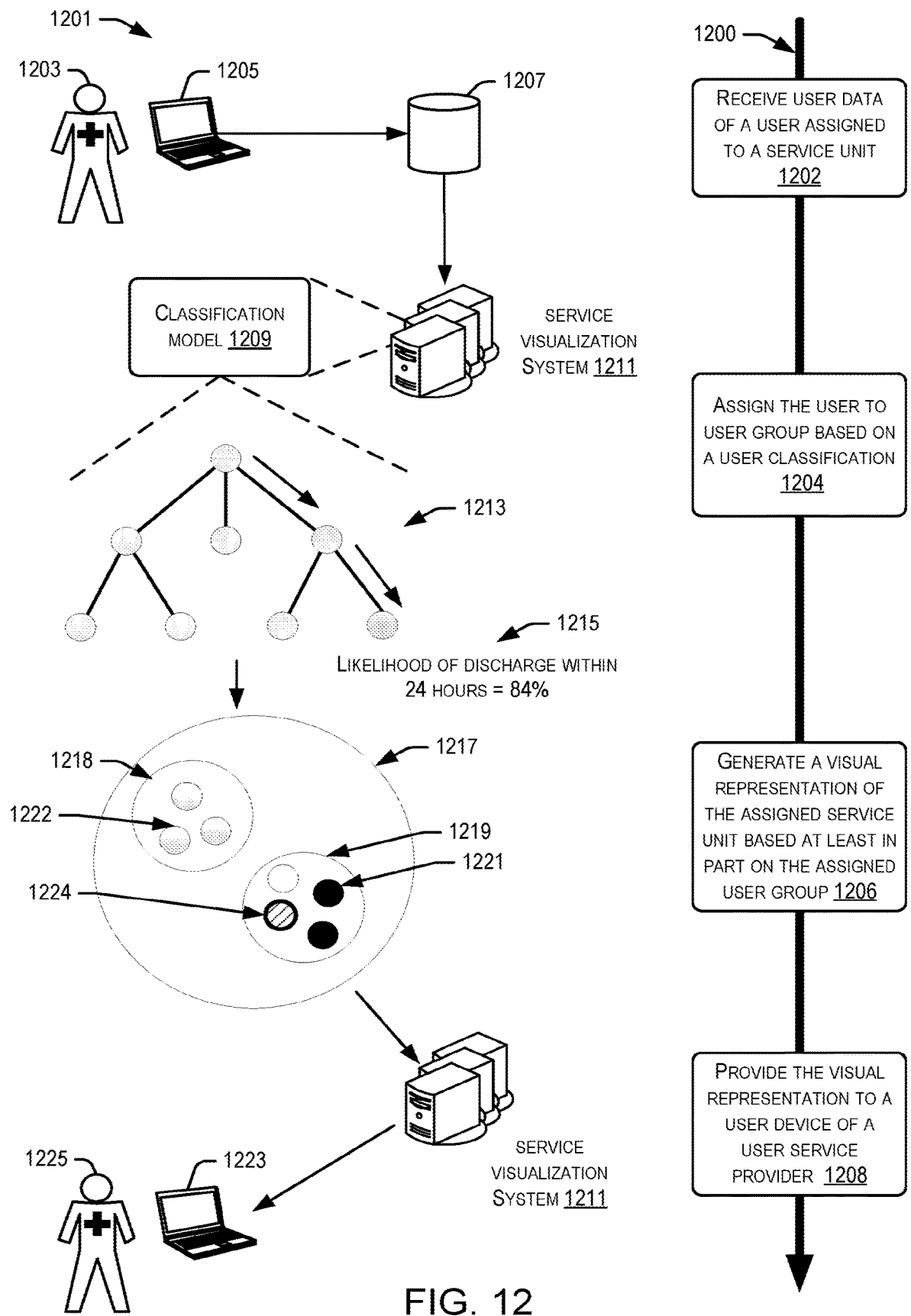
FIG. 12 is an example flowchart illustrating a process for coordinating user service based on user and/or resource classifications, according to at least one example.

FIG. 12 illustrates a simplified block diagram 1201 depicting an example process 1200, in accordance with at least one example. The process 1200 is an example process for providing a visual representation of a service unit to a user device of a USP using a prediction (e.g., classification)

model. The prediction model may be trained to classify users and/or resources into one or more classifications. The diagram 1201 depicts example states that correspond to the blocks of the process 1200. The diagram 1201 includes devices 1205 and 1223, a data store 1207 (e.g., which may be similar to data store 226 of the transformative processing engine 202), and SV system 1211 (e.g., which may be similar to SV system 1102 of FIG. 11), that perform at least a portion of the process 1200.

The process 1200 begins at block 1202 whereby an SV system receives, from a device, user data for a user of a service facility. The user may be assigned to a service unit (e.g., a branch of the ED) of a plurality of service units of the service facility. In some examples, the service facility may be one of a plurality of service facilities affiliated with a service organization. The service organization may be associated with a service management system that maintains user data for the user. The service management system may be affiliated with the SV system 1211. Turning to diagram 1201 in further detail, device 1205 may be operated by a USP of a service facility and may receive input related to the particular user's service/condition. For example, the device 1205 may correspond to a generation component (e.g., generation component 906 of FIG. 9), such as a blood chemistry analyzer, a laptop, a service imaging device, etc. As described herein, the user data may include structured or unstructured user data, and may be associated with a present condition (e.g., an injury or illness) or a present service status (e.g., an order for user discharge, and order to admit the user as an inpatient) of the user. Some non-limiting examples of the user data may include blood lab data, vital signs (e.g., body temperature, blood pressure, etc.), user age, user body mass index (BMI), admission data, user demographics, etc. Upon receiving input, the device 1205 may transmit the user data for the particular user over a network to the SV system 1211 (and/or an affiliated service management system) for storage in data store 1207 of the service management system. The user data may be incorporated into a new or existing user service record of the user. It should be understood that, although in this example, a user data for a single user is described, in other examples, user data for multiple users may be received (e.g., for an entire service facility, department within a facility (e.g., Emergency Department), division, or enterprise). The user data may be received according to any suitable cadence (e.g., in substantially real-time, whenever a user's record is updated, or on a predetermined schedule).

At block 1204, the SV system 1211 may assign the user to a user group based on a user classification. For example, in a first step, the SV system 1211 may retrieve the user data from the data store 1207 of the service management system for input into the trained classification model 1209. In some examples, the trained classification model 1209 may be trained according to one or more machine learning algorithms (e.g., a boosted decision tree 1213), as described in reference to FIG. 10 (e.g., blocks 1002-1006). The trained classification model 1209 may be trained to determine a classification for the user, whereby the classification may correspond to at least one of a condition or service status of the user. In an example, the trained classification model 1209 may output a score based in part on the received user data, whereby the score corresponds to a level of confidence of a particular classification of the user (among a plurality of candidate classifications). In some examples, the particular classification may be associated with the present condition (e.g., the user has a fever) or the present service status of the user (e.g., the user has a Foley catheter inserted). In some examples, the classification may be associated with a predicted future condition (e.g., the user is likely to acquire an infection) or future service status (e.g., the user is likely to require antibiotics) of the user. Continuing with diagram 1201 of FIG. 12 for illustration, the trained classification model 1209 (e.g., utilizing the boosted decision tree 1213) may output of a probability score 1215 of 0.84 (i.e., 84%) corresponding to a prediction of a future service status of the user (i.e., that the user is likely to be discharged within 24 hours). The SV system 1211 may then classify the user as likely to be discharged within 24 hours. As described herein, this classification may be based at least in part on the score being in accordance with (e.g., greater than or equal to) a classification threshold (e.g., 80%), which may be associated with a level of confidence of the score. The SV system 1211 may then assign the user to a user group based at least in part on the classification of the user. Members of the user group may be determined based at least in part on each member having the same classification in common with other members of the user group. Using the example above, the user group may include a set of users which have each been classified as being likely to be discharged within the next 24 hours.

It should be understood that the SV system 1211 may classify a user according to more than one classification. For example, the user may be classified as both: (1) likely to be discharged within 24 hours, and (2) likely to require readmission to a service facility within a predefined period of time (e.g., 30 days). Also, in some examples, a user group may be composed of users who are classified with more than one classification. For example, a particular user group may composed by members who are both likely to be discharged within 24 hours, and likely to require readmission to a service facility within a predefined period of time.

At block 1206, the SV system 1211 may generate a visual representation of at least a portion of the service unit in which the user is assigned, based at least in part on the assigned user group. Continuing with diagram 1201 for further illustration, the visual representation may include at least a portion of one or more service units. For example, service unit 1217 may correspond to an ED of a service facility, and may be represented by a circle shape. The service unit 1217 may include one or more other service units (e.g., service unit 1218 and service unit 1219), each of which may also be represented by circle shapes within service unit 1217 (i.e., forming concentric circles that may indicate a hierarchical relationship). In an example, service unit 1218 may correspond to a first branch of the ED, and service unit 1219 may correspond to a second branch of the ED. Each service unit may include one or more users and/or one or more resources (e.g., beds). In some examples, the assigned user group(s) of at least a portion of the users within a service unit may be represented by the visual representation. For example, as depicted in diagram 1201, service unit 1219 may contain four beds. One bed 1224 may be occupied by the user that was predicted at block 1204 (e.g., with probability score 1215) to have a likelihood of discharge within 24 hours. In this example, the assigned user group (e.g., based on the user classification) may be visually signified by a particular pattern within the circle. In another example, if another user were to be similarly classified (e.g., with a likelihood of discharge within 24 hours), and thus assigned to the same (i.e., common) user group, they may also be indicated within the visual representation by a similar indicator (e.g., the particular pattern within the circle).

In some examples, the visual representation may also indicate an assigned resource group of one or more resources within the portion of the service unit(s) represented. For example, similar to as described above in regards to user data, the SV system 1211 may determine resource status data corresponding to a status of a resource associated with the represented service units. For example, the SV system 1211 may receive input from a clinician or other entity (e.g., a monitoring camera) indicating that a resource (e.g., a bed) is clean or dirty. In this example, a dirty bed may indicate that the bed needs to be cleaned so that another user (e.g., currently in the waiting room) may be checked in and occupy the bed. A clean bed may indicate an available bed which may be assigned to a user. The SV system 1211 may assign the resource to a particular resource group (e.g., a group of beds that are classified as dirty (or clean)). Continuing with the example of diagram 1201, service unit 1219 may contain three other beds in addition to bed 1224. Two of the beds (e.g., including bed 1221) may be dirty and unoccupied (e.g., respectively signified by black circles), and one bed may be clean and unoccupied (e.g., signified by a white circle). Also, service unit 1218 may contain three beds, all of which are currently occupied by respective users (respectively signified by shaded circles). In this example, the three beds may be assigned to a common resource group that corresponds to beds that are currently occupied by users. In this way, the visual representation may present a hierarchical view of one or more service units of a service facility. The visual representation may indicate any suitable presentation of assigned user groups of users and/or assigned resource groups of resources. It should also be understood that any suitable combination of indicators (e.g., of assigned user groups and/or assigned resource groups) may be depicted within a visual representation. For example, a circle that contains a first pattern inside the circle (e.g., similar to bed 1224) and a first line thickness corresponding to the circumference of the circle may indicate both that the user has a likelihood of discharge within 24 hours (e.g., one user grouping) and that they are predicted to have a high probability of readmission within 30 days (another user grouping). In another example, a circle with different indicators from the previous example (e.g., a second pattern inside the circle, surrounded by a line circumference with a second line thickness) may indicate both that a user has special needs (e.g., they are disabled and require wheelchair access) and that the bed is a specially equipped bed for disabled persons. It should also be understood that the various indicators and groupings described herein are for illustration purposes only. Any suitable visual indicators, groupings, and/or combinations thereof may be suitable for performing examples of the present disclosure. For example, although as primarily depicted herein, service units are represented by circles, examples of the present disclosure should not be construed to be so limited (e.g., rectangular shapes or other suitable depictions could be used). Also, as discussed further herein, the SV system 1211 may be used to determine one or more recommendations that may be presented via the visual representation generated by the SV system 1211. These recommendations may also be presented in any suitable form, including, but not limited to, color indicators, shape indicators, text, images, etc. For example, a circle that is filled with solid color may correspond to a recommendation that a user currently assigned to the bed should receive specialized service (e.g., due to having special needs, such as an IV drip). In some examples, users that are assigned to the same user grouping may be associated with similar recommendations (e.g., and may be also have similar visual indicators).

In some examples, the hierarchical view provided by the visual representation of SV system 1211 may correspond to any suitable level of abstraction (or hierarchical visualization). For example, the visual representation may be abstracted (e.g., zoomed out) to represent a service facility view of not only the ED service unit, but also other service units within the service facility that are at a similar hierarchical level as the ED. In another example, the visual representation may represent an enterprise-wide view that includes multiple service facilities. It should be understood that, as the visual representation is zoomed out, the details presented may be abstracted to be suitable for the particular view. For example, while the service unit 1217 that is depicted in FIG. 12 is suitable to present individual users and/or beds, another visual representation may aggregate user details for multiple users (e.g., to a per department, per facility, per division level, or any other suitable aggregation). In one example, a particular visual representation may correspond to presenting service units that are classified as "hot spots" (e.g., signifying a high workload and/or urgent tasks). In this example, the visual representation may not indicate each user within service unit (e.g., the ED), but instead, may highlight the entire service unit as a hot spot. If a clinician drills down (e.g., by clicking on the particular service unit), the SV system 1211 may present another view that allows the clinician to see more details on a per-user level. In this way, the visual representation may present a hierarchical view of one or more service units of a service facility.

At block 1208, the SV system 1211 may provide the visual representation to a user device of a USP. In some examples, the visual representation may be used to coordinate service for the user, for example, among various service units of the service facility. Using diagram 1201 for illustration, the SV system 1211 may transmit data corresponding to the visual representation to a user device 1223 of a USP 1225 (e.g., a nurse, a physician, an operating room (OR) scheduling coordinator, a facility emergency services coordinator, etc.). In some examples, the user device 1223 may then display the visual representation (e.g., via a Web browser, native application, etc.). As discussed herein, the visual representation may be updated in substantially real-time as new data (e.g., user data and/or resource status data) is received and processed by the SV system 1211. In this way, the USP 1225 may have up-to-date information for making decisions (e.g., following recommendations provided by the SV system 1211) about user service and resource management throughout one or more service facilities of an enterprise.

Figure 13:
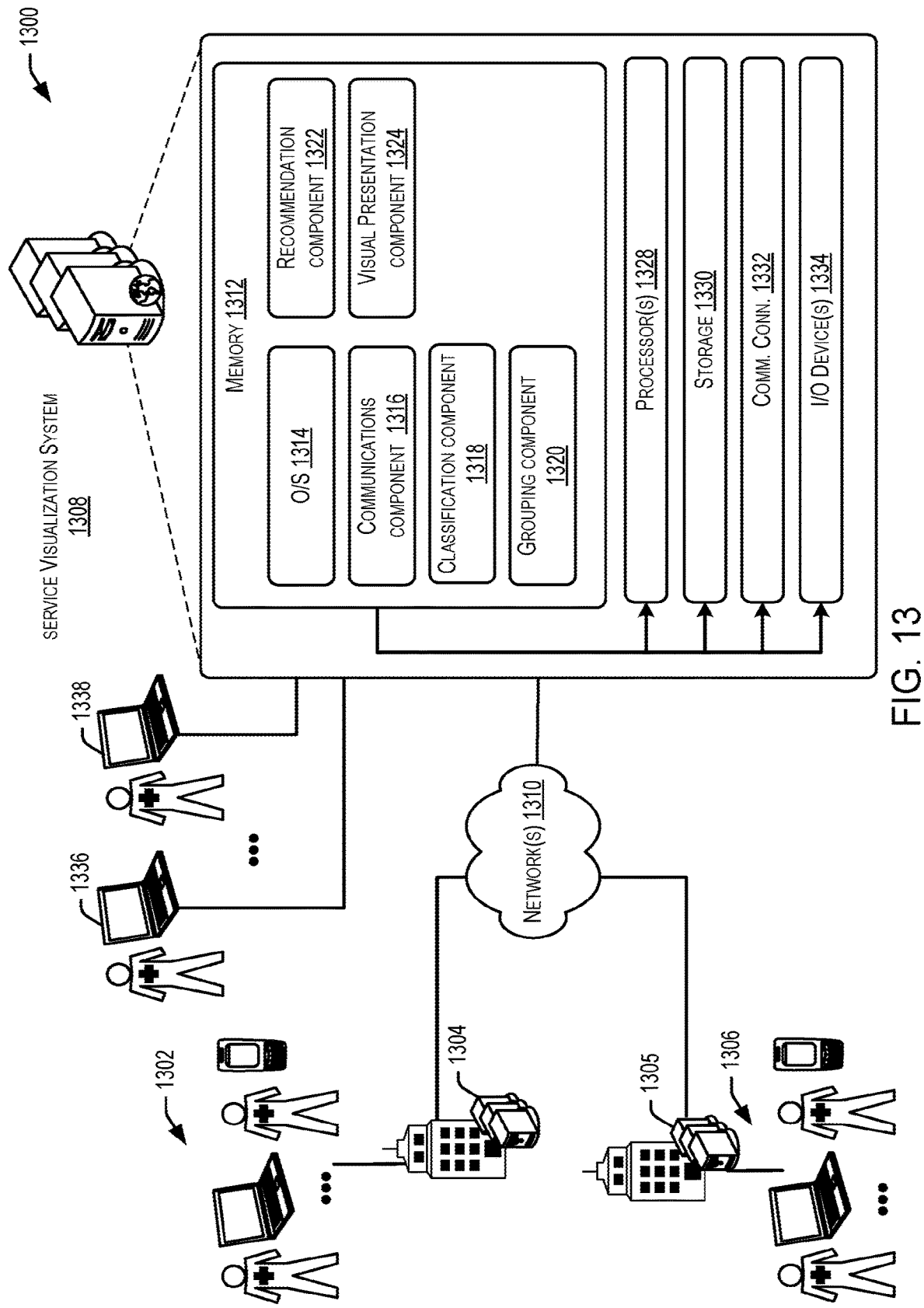
FIG. 13 is another example architecture illustrating a system in which techniques relating to coordinating user service based on user and/or resource classifications may be implemented, according to at least one example.

FIG. 13 illustrates a simplified block diagram depicting an example architecture 1300 of an SV system, in accordance with at least one example. The diagram depicts a plurality of service facilities, whereby each service facility may be affiliated with a service organization that maintains a service management system. Each service facility may further be associated with (e.g., employ) one or more USP's (e.g., respectively represented in FIG. 13 by USP's 1302 and 1306). Each USP (e.g., including physicians, nurses, etc.) may be responsible for service for one or more users. A device (e.g., tablet, mobile phone, laptop, desktop, server, lab equipment, etc.) associated with the USP may receive input from the USP and generate user data (and/or resource status data) that is transmitted to a system associated with the particular service facility. For example, as depicted in architecture 1300, the respective service facilities are each associated with an EMR system (e.g., EMR systems 1304, 1305). Upon receiving user data, an EMR system (e.g., the EMR system 1304) may then transmit the user data over a network 1310 to an SV system 1308 (which may be similar to SV system 1102 or 1211). The SV system 1308 may process the user data, as described below, and subsequently transmit data for presentation on one or more devices (e.g., represented by device 1336 and device 1338) to be used in coordinating user service.

It should be understood that a service facility may be associated with any number and/or type of suitable systems (e.g., resource management systems, third party service provider systems, etc.). Also, it should be understood that, although the EMR systems 1304 and 1305 are depicted in FIG. 13 as being respectively associated with a particular service facility, embodiments should not be construed to be so limited. For example, the service management system (e.g., maintained by the service organization) may be associated with a plurality of EMR systems that are distributed in any suitable fashion (e.g., geographically dispersed per division, per department, etc.). Also, the devices 1336 and 1338 may each be associated with different types of USP's and/or present different types of data, depending on the context, as described herein. For example, in one context, device 1336 may be associated with a floor nurse that manages user throughput on a facility floor, while device 1338 may be associated with an OR scheduling coordinator. In each of these contexts, the respective devices may present a visual representation via a GUI of the respective device (e.g., a dashboard) suitable for the role of the respective user.

It should further be understood that the user data and/or resource status data received by the SV system 1308 may be representative of a large number of users and/or resources (e.g., over 300,000 users of the service organization). This data may be used to define one or more sets of training data, as described in reference to FIGS. 9-10 (e.g., the data preparation engine 914 of FIG. 9). The one or more sets of training data may be stored in a data store (e.g., data store 915) of the SV system 1308.

Turning to network 1310 in further detail, the network 1310 may include any suitable communication path or channel such as, for instance, a wire or cable, fiber optics, a telephone line, a cellular link, a radio frequency (RF) link, a WAN or LAN network, the Internet, or any other suitable medium. The network 1310 may include any one or a combination of many different types of networks, such as cable networks, the Internet, wireless networks, cellular networks, and other private and/or public networks. In some examples, as described above components of the architecture 1300 (e.g., EMR systems 1304 and 1305, devices 1302, 1306, 1336, and/or 1338) may communicate over the network 1310 with the user navigator system via HL7 formatted messages or any other suitable format.

Turning to the contents of the SV system 1308 in more detail, the SV system 1308 may be a computer system that includes at least one memory 1312, one or more processing units (or processor(s)) 1328, a storage unit 1330, a communication device 1332, and an I/O device 1334. The processor(s) 1328 may be implemented as appropriate in hardware, computer-executable instructions, firmware or combinations thereof. Computer-executable instructions or firmware implementations of the processor(s) 1328 may include computer-executable or machine executable instructions written in any suitable programming language to perform the various functions described.

The memory 1312 may store program instructions that are loadable and executable on the processor(s) 1328, as well as data generated during the execution of these programs. Depending on the configuration and type of SV system 1308, the memory 1312 may be volatile (such as random access memory (RAM)) and/or non-volatile (such as read-only memory (ROM), flash memory, etc.). In some implementations, the memory 1312 may include multiple different types of memory, such as static random access memory (SRAM), dynamic random access memory (DRAM) or ROM. The SV system 1308 may also include additional storage 1330, such as either removable storage or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some examples, the additional storage 1330 may include (or be affiliated with) one or more data stores of the transformative processing engine 202 of the service management system.

The SV system 1308 may also contain communications connection(s) 1332 that allow the SV system 1308 to communicate with a stored database, another computing device or server, user terminals, and/or other devices on the network(s) 1310 (e.g., generation component(s) 1108 of FIG. 11). The SV system 1308 may also include input/output (I/O) device(s) and/or ports 1334, such as for enabling connection with a keyboard, a mouse, a pen, a voice input device, a touch input device, a display, speakers, a printer, etc.

Turning to the contents of the memory 1312 in more detail, the memory 1312 may include an operating system 1314 and one or more application programs or services for implementing the features disclosed herein, including a communications component 1316, a classification component 1318, a grouping component 1320, a recommendation component 1322, and a visual presentation component 1324.

The operating system 1314 may provide executable program instructions for the general administration and operation of SV system 1308 and typically will include a computer-readable storage medium (e.g., a hard disk, random access memory, read only memory, etc.) storing instructions that, when executed by a processor of the SV system 1308, allow the SV system 1308 to perform its intended functions. Suitable implementations for the operating system and general functionality of the servers are known or commercially available and are readily implemented by persons having ordinary skill in the art, particularly in light of the disclosure herein.

The communications component 1316 may include code that causes the processor 1328 to generate messages, forward messages, reformat messages, and/or otherwise communicate with other entities (e.g., using an HL 7 format or any other suitable format). For example, the communications component 1316 may receive user data associated with a user from an EMR system (e.g., 1304) and/or one or more devices (e.g., 1302). As described above, it should be understood that the communications component 1316 may receive data (e.g., user data, resource status data) from any suitable source (e.g., emergency department (ED) discharge systems, service clinics, monitoring cameras, lab equipment, etc.). In some examples, the communications component 1316 may further communicate with an enterprise master user index (EMPI) (e.g., of the service management system) to ensure that user data received from various devices and/or EMR systems are consistent for a given user (e.g., utilizing a unique identifier for a given user of the service management system). In some examples, the communications component 1316 may receive messages that correspond to a data stream (e.g., a sequences of messages transmitted in substantially real-time). In some examples, the data stream may be transmitted from one or more sources (e.g., EMR systems) to an intermediary data store, before being eventually stored in an electronic data warehouse (EDW). The communications component 1316 may analyze (e.g., parse) the messages from the data stream while stored in the intermediary data store, and determine if they should be further processed (e.g., trigger occurrence detection, as described herein) and/or stored by the SV system 1308 (e.g., in storage 1330).

The classification component 1318 may include code that causes the processor 1328 to classify a user or a resource with a particular classification. In some examples, as described herein, the classification component 1318 may employ one or more trained prediction models (e.g., as described in reference to FIGS. 9-10). In some examples, a user and/or resource may be classified into more than one classification.

The grouping component 1320 may include code that causes the processor 1328 to assign an entity to a group. For example, the grouping component 1320 may assign a user to a user group and/or or a resource to a resource group. In some examples, the particular members of the group may have at least one classification in common with other members of the group. For example, the grouping component 1320 may assign a clean bed to a particular bed group, whereby all the members of the particular bed group have been classified as being clean beds. In some examples, a user and/or resource may be assigned to more than one respective group.

The recommendation component 1322 may include code that causes the processor 1328 to generate a recommendation for a user or a resource of a service facility. In some examples, the recommendation component 1322 may generate the recommendation based at least in part on a previous classification and/or assigned grouping of the user or the resource. For example, a user that is classified as being likely to be a readmitted user within 30 days of discharge from the current admission may be assigned to a particular user group. The recommendation component 1322 may generate a recommendation for users within that user group, for example, indicating that the user should receive specialized service (e.g., scheduling follow-up appointments with the user's primary service physician), to reduce the risk of being a readmitted user. In some example, users within the user group may receive a similar recommendation for service. In other examples, the recommendation component 1322 may generate a customized recommendation for the particular user. For example, the user may be assigned to multiple user groups (e.g., users having a fever, users having a Foley catheter inserted, and users allergic to a specific medication). The recommendation component 1322 may generate a custom recommendation for the user, taking into account characteristics of each of the assigned user groups. For example, the recommendation may indicate that the particular user has a high risk of contracting a catheter-associated urinary tract infection (CAUTI), and should receive an alternate form of medication from what is typically prescribed to users at risk of a CAUTI. The recommendation component 1322 may utilize any suitable algorithm (e.g., a heuristic algorithm or machine learning algorithm, as described herein) to determine the recommendation. Similarly, the recommendation component 1322 may generate recommendations for resources (e.g., a recommendation for cleaning a bed). It should be understood that the recommendation component 1322 may take into account both assigned user groups and resource groupings when making recommendations. For example, the recommendation component 1322 may determine that a bed in the ICU is dirty (e.g., assigned to a "dirty beds" group), and also that a user in the ED is a candidate for being transferred to the ICU. The recommendation component 1322 may thereby determine that the bed should be cleaned, so that the user may be transferred, thereby increasing user throughput.

The visual presentation component 1324 may include code that causes the processor 1328 to generate a visual representation. The visual representation may correspond to any suitable portion of an enterprise (e.g., one or more service facilities, one or more departments within a service facility, etc.). The visual representation may include one or more service units, whereby each service unit may include (and/or be associated with) one or more users and/or resources (e.g., beds). The visual representation may be represented using any suitable expression (e.g., HTML code, XML-based languages) and transmitted by the SV system 1308 to a user device (e.g., 1336, 1338).

FIGS. 14-21 respectively illustrate different visual representations of GUIs that may be displayed on a user device, according to various examples. Each of the visual representations depicted by FIGS. 14-21 may be generated by an SV system (e.g., SV system 1308 of FIG. 13, SV system 1211 of FIG. 12) and transmitted to a user device for presentation on the device (e.g., user device 1336 or 1338 of FIG. 13). In some examples, the visual representation may correspond to a dashboard presentation. The dashboard presentation may allow a user to view different views, for example, depending on the type of user (and/or job function/task). The dashboard may allow the user to toggle between different views. In some examples, a particular view of the dashboard may allow the user to drill-down to view a more detailed view (e.g., by clicking on a portion of the view, such as a particular service unit), as described below in reference to FIGS. 15-16. Alternatively, the dashboard may also allow the user to zoom out to see a more abstracted view (e.g., a view of an entire service facility). It should be understood that, while some of the GUIs illustrated herein may have similar graphical presentations (e.g., FIGS. 14-17 and 19-21, using circles to depict service units), other GUIs also generated by the SV system may have different graphical presentations (e.g., FIGS. 18, using columns to depict service units within a schedule-based visual representation).

Figure 14:
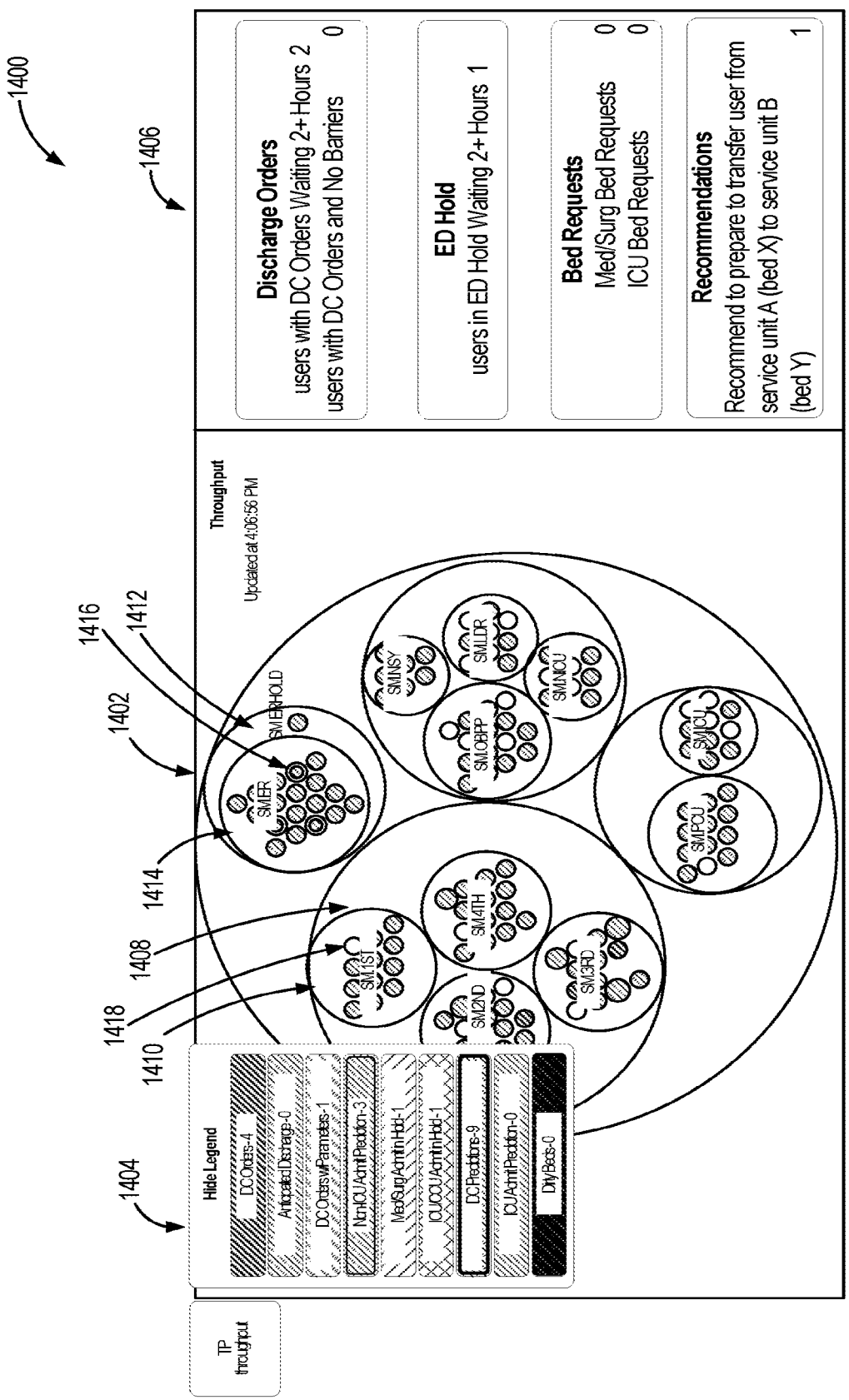
FIG. 14 illustrates an example graphical user interface (GUI) for coordinating user service based on user and/or resource classifications, according to at least one example.

Turning to FIG. 14 in further detail, FIG. 14 illustrates a GUI 1400 of a display of a user device, according to at least one example. The GUI 1400 includes several components, including a legend 1404, a view 1402, and an information pane 1406. In this example, the view 1402 provides a visual representation that may allow a USP to track user throughput among one or more service units of a particular service facility. As described herein, any of the components of GUI 1400 may be updated in substantially real-time, as new data is received (e.g., resource data, user data), and in any other suitable manner. In view 1402, multiple service units are depicted, whereby each service unit corresponds to a circle shape (e.g., service unit 1412 (e.g., the ED), and service unit 1408 (e.g., the Med/Surg department)). Using service unit 1412 for illustration, two service units are contained within the service unit 1412 (e.g., the emergency room (ER) 1414, and a holding room). Similarly, service unit 1408 contains four service units, which may each correspond to different floors of the Med/Surg department. Drilling down further, service unit 1414 contains a plurality of beds, each bed corresponding to a circle within service unit 1414. The status of each bed may be indicated according to one or more visual indicators, illustrated by the legend 1404. For example, the circle corresponding to bed 1416 has an outline around the circle, and the outline may have a particular color (e.g., blue). In legend 1404, this may correspond to a prediction that a user that is currently assigned to bed 1416 is predicted to be require admission to the Med/Surg service unit (e.g., a "Non-ICU Admit Prediction"). In some examples, each visual indicator within the legend 1404 may correspond to a particular assigned group (e.g., a user group and/or resource group) to which a user and/or resource is assigned (e.g., based on a previously determined classification by the SV system). In other non-limiting examples, the legend 1404 may provide visual indicators that correspond to whether a user: has discharge (DC) orders, is anticipated to be discharged (e.g., received via input from a USP), has DC orders with parameters (e.g., special instructions for an assigned discharge nurse), is predicted to be discharged (e.g., by a prediction model of the SV system), whether a bed is dirty and unoccupied (e.g., a black circle), whether a bed is clean and unoccupied (e.g., a white circle), whether the user is predicted to be admitted to the ICU (or the Med/Surg unit), whether the user has been admitted, but is in holding and waiting for a bed, etc. In the example illustrated by GUI 1400, service unit 1410 is shown to contain at least one clean bed 1418.

The GUI 1400 further contains the information pane 1406. The information pane 1406 may contain further information related to the view 1402. In one example, the information pane 1406 may contain information that summarizes data that is visually presented in the view 1402. For example, the information pane 1402 may indicate that there are currently 2 users with DC orders that have been waiting for at least 2 hours. This type of information may serve as a form of recommendation to a USP that these users should be prioritized to be discharged, for example, to improve user satisfaction and/or to make room for other users who are waiting for clean beds. In another example, the information pane 1406 may explicitly recommend an action to be taken. For example, as depicted in the information pane 1406, and continuing with the above illustration, the SV system may recommend that the user currently assigned to bed 1416 ("bed X") of service unit 1414 (e.g., "Service Unit A") should be prepared to be transferred to bed 1418 ("bed Y") of service unit 1410 (e.g., "Service Unit B"). In another example, the information pane 1406 may recommend that a particular bed be cleaned or that the bed itself should be transferred to another service unit. As described herein, it should be understood that any suitable types of recommendations and/or corresponding recommendation indicators may be presented within a visual representation. For example, a visual indicator of legend 1404 may be used to indicate a particular recommendation for one or more users within view 1402 (e.g., without corresponding text in the information pane 1406). In another example, audio (e.g., a beep, audio instruction, etc.) or video feed (e.g., showing the room where the user should be transferred to) may be used to signal a recommendation. By providing indicators (e.g., visual indicators) within the view 1402 and/or summaries of relevant information that may be actionable by a USP, the SV system may enable improved user throughput within/ across service units of a service facility.

Figure 15:
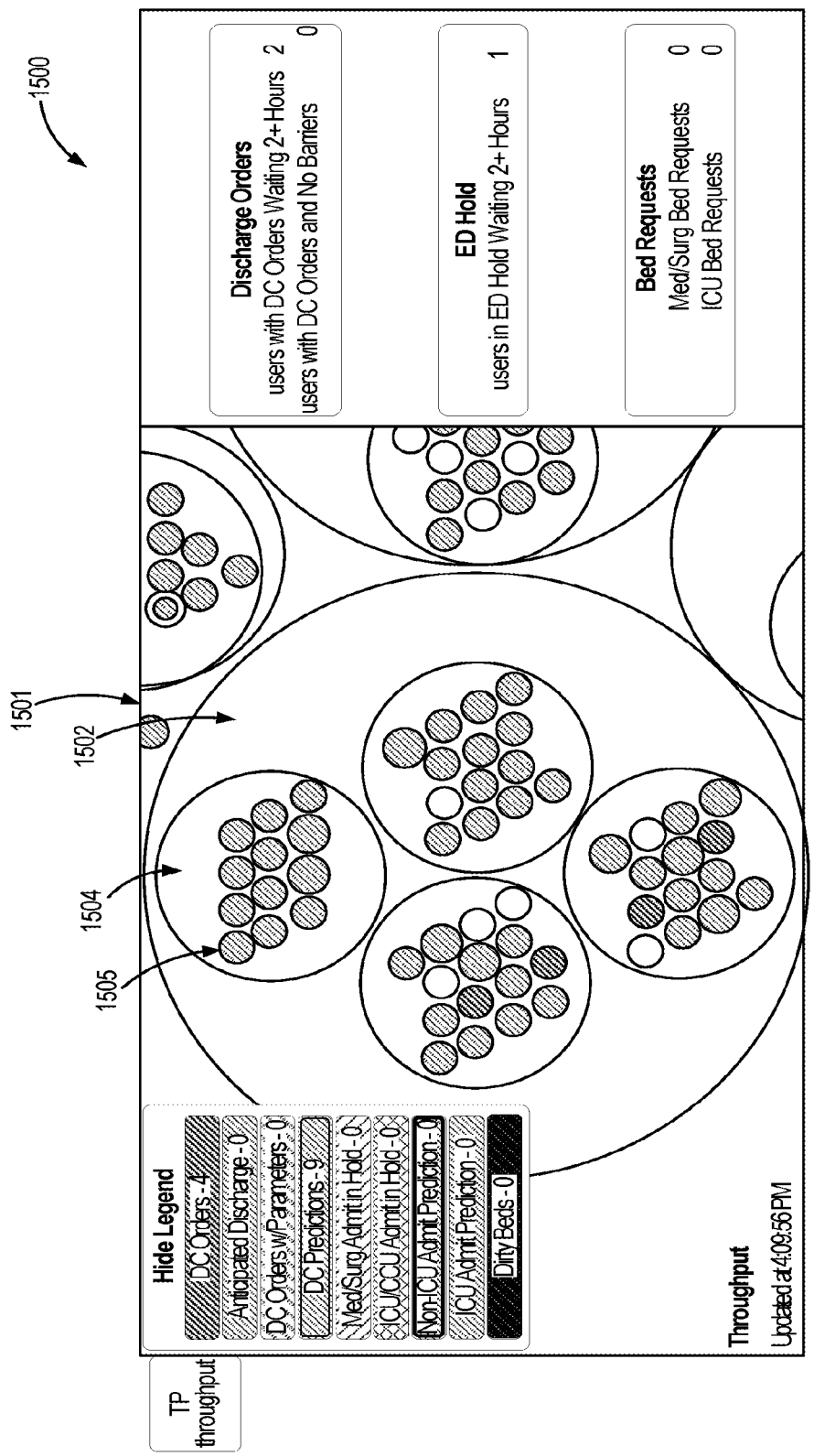
FIG. 15 illustrates another example GUI utilizable for coordinating user service based on user and/or resource classifications, according to at least one example.

FIG. 15 illustrates a GUI 1500 of a display of a user device, according to at least one example. As described above, GUI 1500 may be similar to GUI 1400 of FIG. 14. For example, GUI 1500 may contain a legend, a view 1501, and an information pane. In the view 1501 of FIG. 15, a zoomed in portion of a service unit 1502 is depicted. For example, the user device may receive user input (e.g., a click on the service unit 1502), which may signal to the user device to zoom in on the particular service unit 1502. In one example, the service units within the zoomed in service unit 1502 may respectively correspond to service units of the Med/Surg service unit 1408 of FIG. 14. For example, the service unit 1504 may correspond to service unit 1410. In this example, each of the beds within service unit 1504 indicate a identifier (e.g., a room number, a bed ID, etc.). It should be understood that the view of service unit 1502 may provide more details (e.g., per bed) than the view 1402 depicting service unit 1410. For example, bed 1505 may be indicated by "416" (not shown), which may indicate a particular room identifier for bed 1505. In some examples, the additional details per bed may be displayed as text that is overlaid on the respective corresponding circle, or any suitable layout (e.g., beside the circle, displayed when hovering over the circle, etc.). In some examples, further details may be displayed by zooming in. For example, as illustrated below in FIG. 16, by clicking on service unit 1504, the user device may display more user details for each bed that is occupied by a user.

Figure 16:
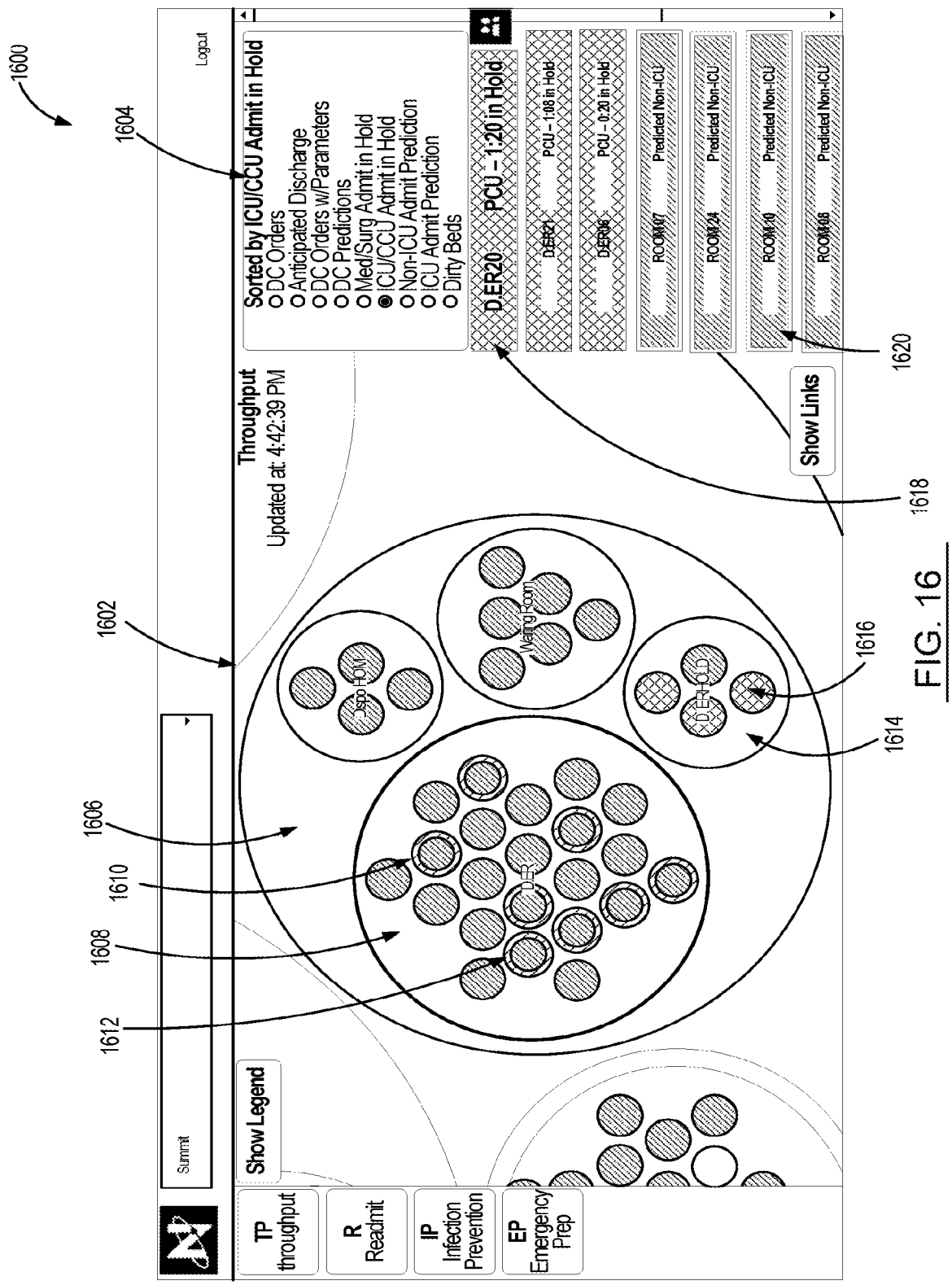
FIG. 16 illustrates another example GUI utilizable for coordinating user service based on user and/or resource classifications, according to at least one example.

FIG. 16 illustrates a GUI 1600 of a display of a user device, according to at least one example. As described above, GUI 1600 may also be similar to GUI 1400 of FIG. 14. For example, GUI 1600 may contain a legend (e.g., collapsed), a view 1602, and an information pane 1604. Similar to FIG. 15, the GUI 1600 of FIG. 16 depicts a zoomed in throughput view 1602. In this example, a zoomed in service unit 1606 is depicted, which may correspond to the ED of a service facility. The ED may contain other service units, for example, an ER service unit 1608 (e.g., including users that are being treated), an ER holding room service unit 1614 (e.g., corresponding to a Progressive Care Unit (PCU)), etc. Note that the two users respectively assigned to bed 1610 and bed 1612 may both be assigned to the same user group (e.g., similar visual indicators, with an outlined circle). In this example, the zoomed in view 1602 activates the information pane 1604 to show more details about each user. For example, panel 1620 indicates that the user assigned to bed 1612 is predicted to be transferred to "Room 10" (e.g., a non-ICU service unit) for service. Similarly, panel 1618 indicates that the user assigned to bed 1616 in service unit 1614 is in holding room 20 of the PCU, and has been waiting for 1 hour and 20 minutes. As depicted, the information pane 1604 may allow a user to sort, for example, according to users who have been waiting the longest time. This may further enable increased throughput of users, by enabling a USP user to properly prioritize which users to service.

Figure 17:
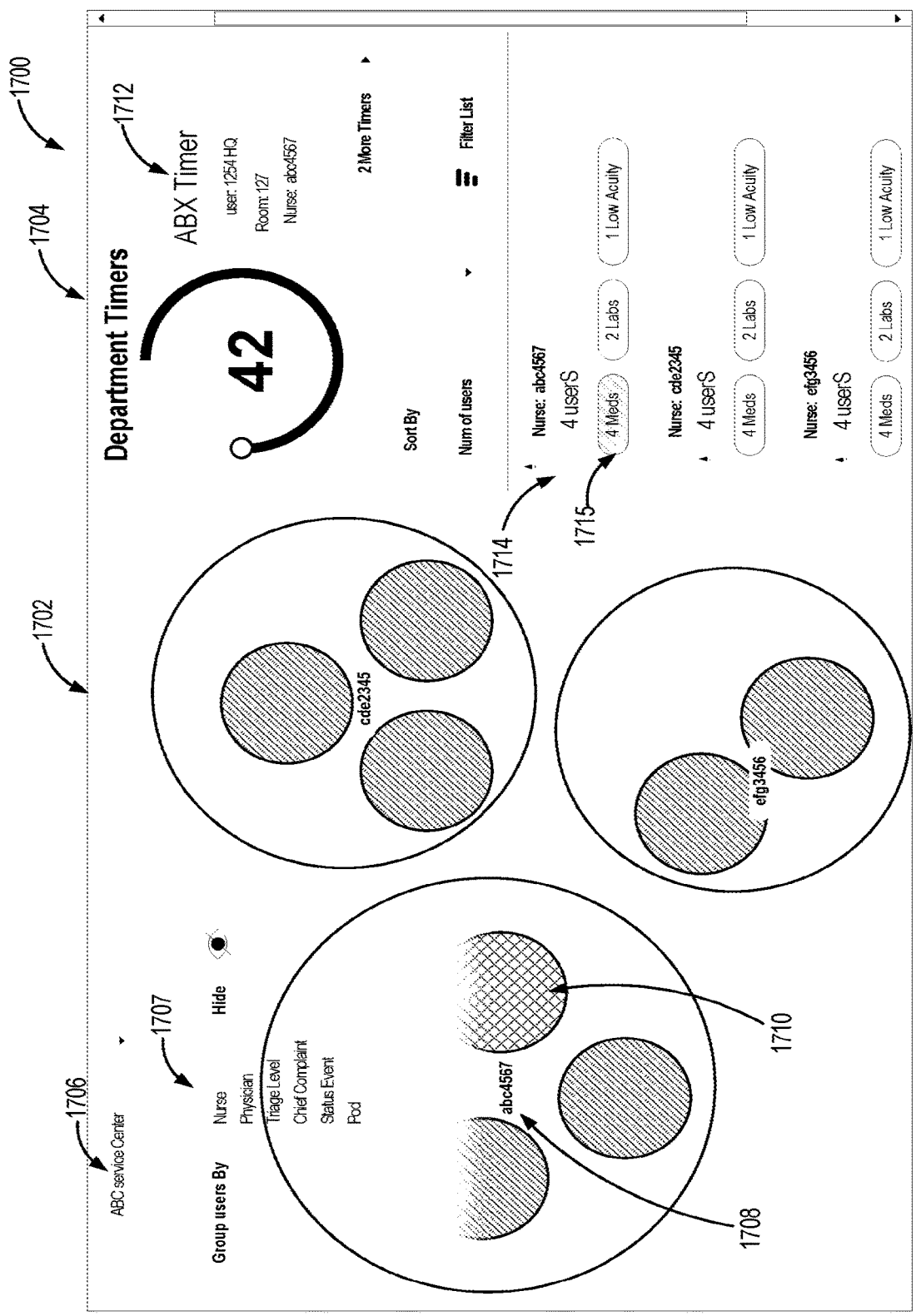
FIG. 17 illustrates another example GUI utilizable for coordinating user service based on user and/or resource classifications, according to at least one example.

FIG. 17 illustrates a GUI 1700 of a display of a user device that may be used to visual one or more hot spots, according to at least one example. In this example, the GUI 1700 depicts a view 1702 and an information pane 1704. The view 1702 depicts three service units. For example, service unit 1708 is indicated by "abc4567," which in turn corresponds to an identifier for a service resource (e.g., a nurse) that is assigned to service for users (e.g., including user 1710) within this service unit 1708. The view 1702 also contains a first dropdown menu 1706 that allows a user to filter by service facility and a second dropdown menu 1707 that allows a user to group users according to different parameters. It should be understood that this dynamic grouping mechanism may allow service units to be generated and/or visualized on demand by a user. For example, instead of visualizing users according to which nurse they are assigned to, a user may visual users by assignments to physicians. As discussed further below, they may be used to indicate hot spots according to any suitable category (e.g., a nurse hot spot, a physician hot spot, etc.).

The information pane 1704 may be used to visualize one or more hot spots. For example, a timer panel 1712 of the information pane 1704 may indicate one or more timers. Each timer may indicate the amount of time that is remaining for a particular task to be completed by a USP (e.g., nurse "abc4567" of service unit 1708). In this example, nurse "abc4567" may have 42 minutes left to complete the task for user "1254HQ" (which may correspond to user 1710 of view 1702). The timer may be used to indicate an urgency (or priority) for completing the task (e.g., administering medication to the user on a predefined cadence). Meanwhile, a hot spot panel 1714 of the information pane 1704 may be used to indicate one or more hot spots. For example, hot spot panel 1714 indicates that nurse "abc4567" is at risk for not being able to complete at least one of the tasks in the timer panel 1712. In this example, the nurse "abc4567" is at risk for not being able to fulfill one or more of 4 medications that are scheduled to be administered to users assigned to the nurse (i.e., within service unit 1708). Here, this is indicated by a patterned indicator 1715. It should be understood that any suitable hot spot indicator may be used. For example, the at risk user 1710 may have a different pattern than other users who are not at risk for having a timer lapse. In some cases, these hot spot indicators may indicate that a clinician is overloaded with tasks, and/or the allotted time for a task currently assigned is too stringent to be completed on time. Accordingly, a user of the GUI 1700 may take action, for example, by reassigning another nurse to assist nurse "abc4567." As described herein, these predictions of which service units (and/or associated clinicians) are hot spots may be generated by the SV system using any suitable technique, for example, as described in reference to FIGS. 9-10. For example, the SV system may use heuristics to determine an average amount of time that a type of task is expected to take. The SV system may then calculate whether a clinician is at risk for not completing the task within the allotted time.

Figure 18:
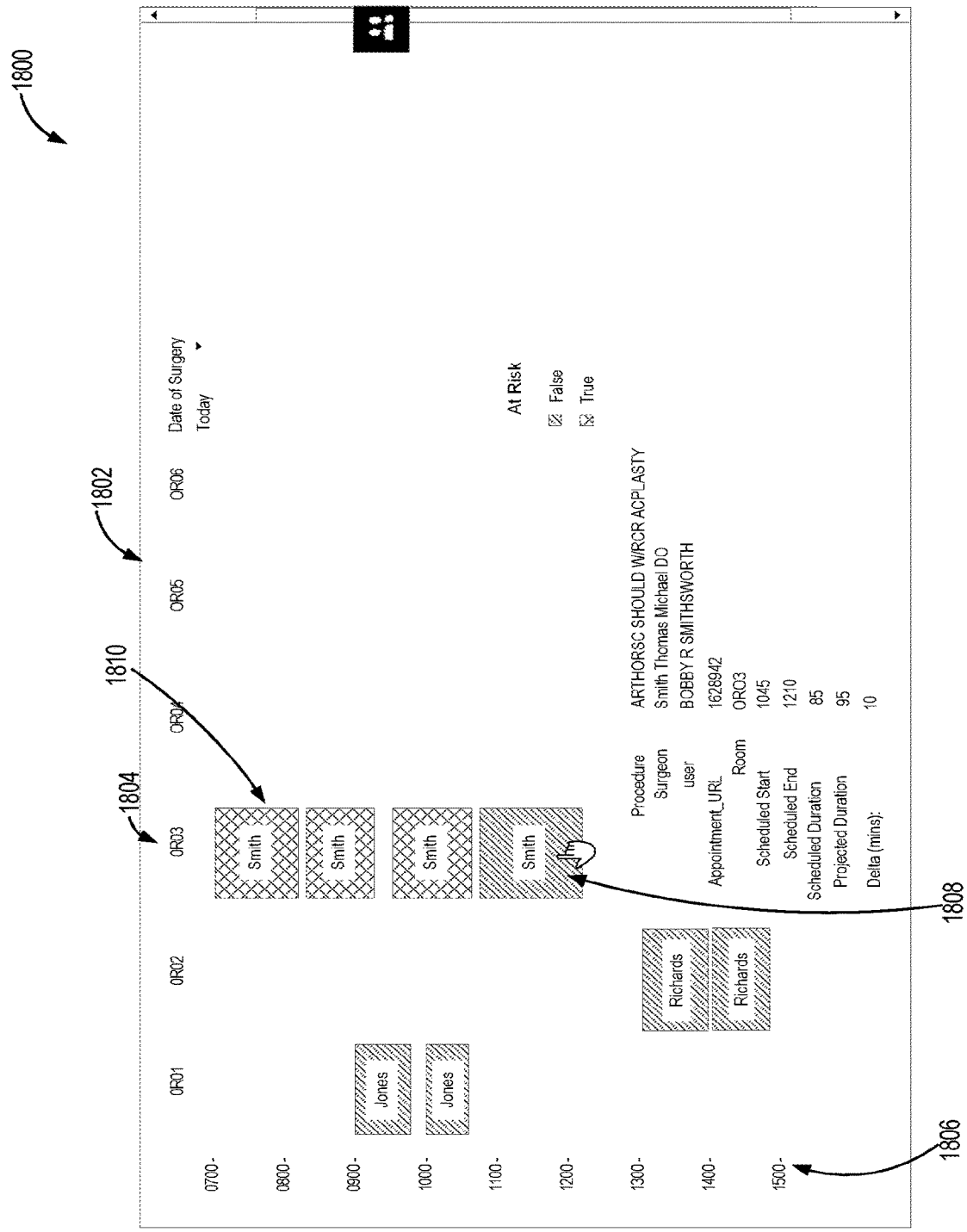
FIG. 18 illustrates another example GUI utilizable for coordinating user service based on user and/or resource classifications, according to at least one example.

FIG. 18 illustrates a GUI 1800 of a display of a user device that may be used to schedule procedures, according to at least one example. For example, GUI 1800 may contain a view 1802 that displays a schedule of appointments for one or more service units (e.g., each service unit corresponding to an operating room for surgeries). The schedule may indicate how long each appointment is scheduled for, according to a time schedule 1806. In one example, operating room 1804 ("OR03") may have four surgery procedures currently scheduled. Each surgery is scheduled to be performed by Dr. Smith. Each procedure may have a visual indicator that indicates whether the procedure is at risk (or not) of not being completed within the projected time slot. For example, procedure 1808 may not be at risk, as indicated by the legend in view 1802. The user may hover over the procedure 1808 and determine details about the procedure, including, for example, a scheduled duration, a projected duration, a time delta (in minutes) between the scheduled duration and the projected duration, etc. In this case, the time delta may be only 10 minutes, and therefore may be considered to be at low risk. However, for the other three procedures currently scheduled for operation room 1804 (e.g., including procedure 1810), they may be determined to be at risk for not completing on time. In some examples, an SV system may utilize a prediction model to predict a duration of a procedure performed by a particular clinician. For example, the prediction model may be trained to predict a duration of a procedure based at least in part on: (1) durations of previous procedures performed by the clinician that are substantially equivalent to the given procedure, and/or (2) durations of previous procedures performed by other clinicians (e.g., within the enterprise) that are substantially equivalent to the procedure. In this way, the SV system may provide recommendations to a user for scheduling a procedure. For example, if a scheduled procedure is at risk for not completing within the allotted timeframe, the procedure may be moved to another OR and/or timeslot. In another example, the SV system may determine a time slot that will fit a planned procedure, and then recommend that the procedure be scheduled within that time slot. This may help to optimally utilize resources (e.g., operating rooms), while reducing the risk of overbooking resources.

Figure 19:
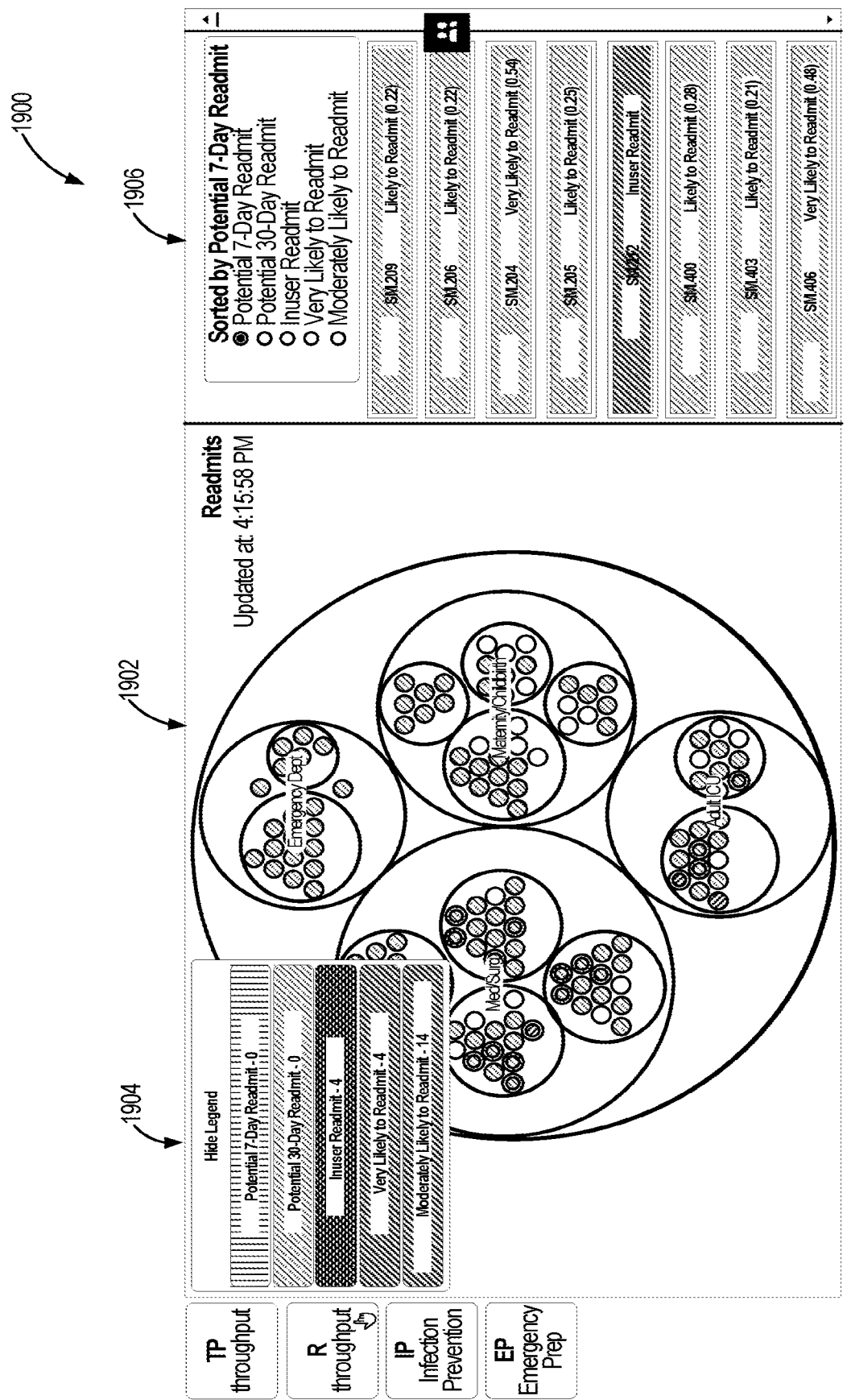
FIG. 19 illustrates another example GUI utilizable for coordinating user service based on user and/or resource classifications, according to at least one example.

FIG. 19 illustrates a GUI display 1900 of a user device that may be used to coordinate user service based at least in part on readmission predictions determined from user data, according to one example. For example, similar to GUI 1400 of FIG. 14, GUI 1900 may include a view 1902, a legend 1904, and an information pane 1906. Also, similar to FIG. 14, the view 1902 depicts multiple service units (e.g., ED, Maternity/Childbirth, Med/Surg, Adult ICU), each of which contain other child service units. Each child service unit depicts a status (e.g., via visual indicators identified by the legend 1904) for one or more users and/or resources (e.g., beds), as described herein. However, whereas in FIG. 14 the visual indicators are primarily used for managing user throughput among service units of the service facility, in FIG. 19, the visual indicators are used primarily to coordinate service for users who may be likely to be readmitted to the service facility in the future. For example, legend 1404 of GUI 1400 identifies visual indicators such as whether a user is predicted to be discharged, whether the user is predicted to be admitted to the ICU (or the Med/Surg unit), whether the user has been admitted, but is in holding and waiting for a bed, etc. These visual indicators are useful, for example, in determining whether a bed should be cleaned or otherwise made available in the ICU (or the Med/Surg unit) to make room for a user that will be transferred from the ED service unit. In the case of legend 1904 of GUI 1900, however, the visual indicators may indicate, for example: whether the user has a moderate potential of being readmitted within 7 days (or 30 days), whether the user currently is classified as an inpatient readmit, whether the user is very likely to be readmitted, or whether the user is moderately likely to be readmitted. As described above, just as a prediction model of the SV system may classify the user with more than one classification (e.g., and thus assign the user to more than one user group), the view 1902 may depict a bed associated with the user as having multiple visual indicators (e.g., respectively associated with each assigned grouping). For example, a user may be very likely to be readmitted, and, for that readmission to be within 7 days of discharge from the present admission.

Similar to information pane 1604 of FIG. 16, information pane 1906 depicts more details about each user. In some examples, these details may be used by a USP to take appropriate action for a user. For example, the USP may determine that the users identified by "SM.204" and "SM.406" are very likely to be readmitted. The USP may then prioritize these users for receiving special follow-up service following their discharge. This may help to reduce the likelihood of the user requiring readmission, and/or decreasing the severity of any future readmission. As described above, the details presented in the information pane 1906 may also include one or more recommendations for the USP to consider when treating the user (e.g., a recommendation to schedule a follow-up visit for the user to their primary service provider shortly after discharge). In some examples, the recommendation may include a suggested prioritization for one or more tasks for a user (and/or task prioritization for tasks involving multiple users). Also, in some examples, the identifier for each user shown in the information pane 1906 may also correspond to an identifier for the user in the view 1902 (e.g., so that the USP may be provided with better visual context of the user within the service unit of the service facility). This may be helpful when coordinating service for multiple users across multiple service units.

Figure 20:
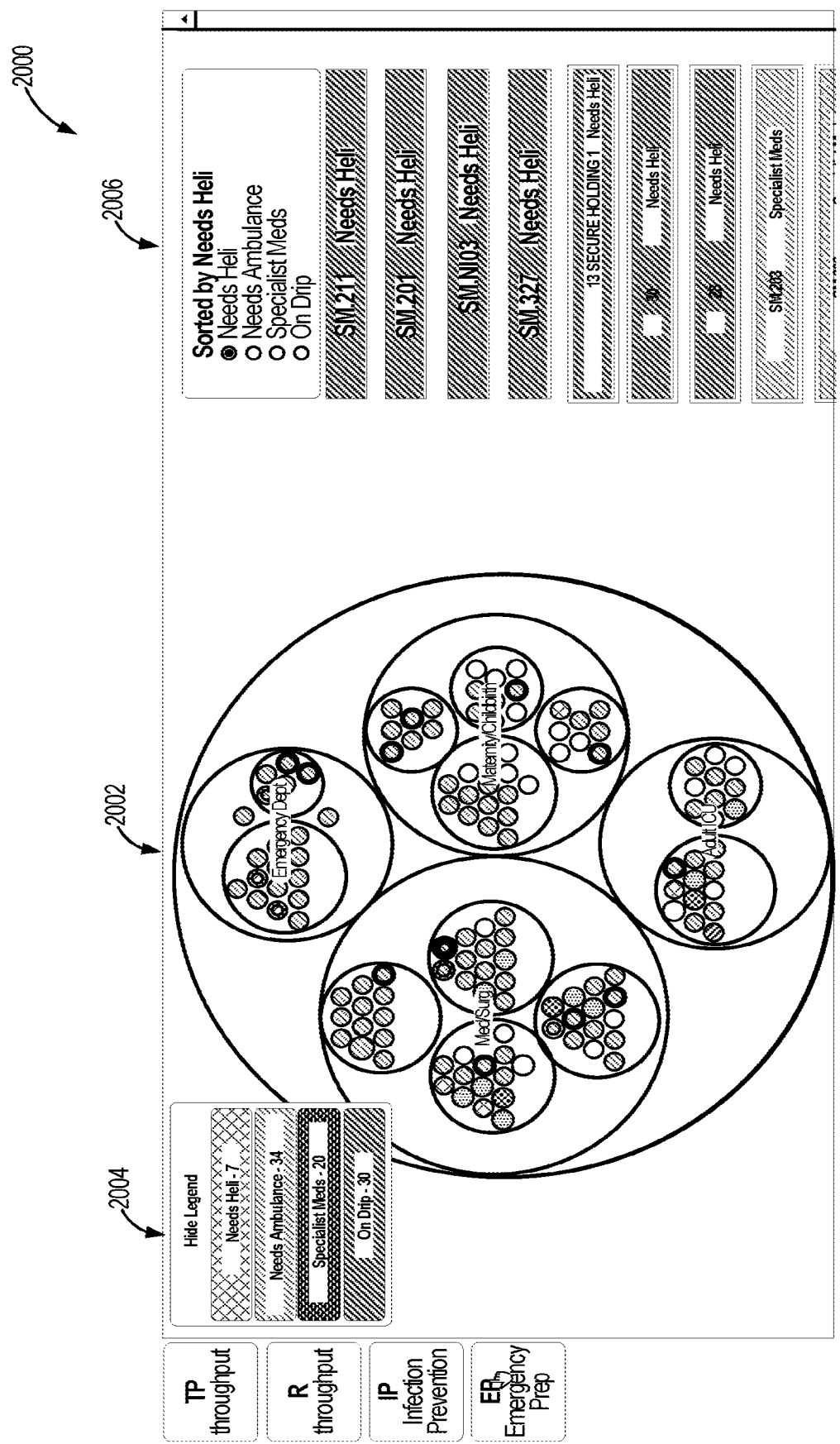
FIG. 20 illustrates another example GUI utilizable for coordinating user service based on user and/or resource classifications, according to at least one example.

FIG. 20 illustrates a GUI display 2000 of a user device that may be used to coordinate user service based at least in part on user data related to emergency preparedness, according to one example. The GUI 2000 may be similar to GUI 1900 of FIG. 19, including a view 2002, a legend 2004, and an information pane 2006. However, in this example, the legend 2004 identifies visual indicators that are used primarily to coordinate providing specialized service for users, especially in the event of an emergency. For example, these visual indicators may correspond, respectively, to whether a user may require helicopter evacuation in an emergency situation, whether the user needs an ambulance in an emergency situation, whether the user requires specialized medication, or whether the user is connected to an IV drip. Also, the information pane 2006 may indicate more details about users (or beds) depicted in the view 2002. For example, the information pane 2006 may indicate that the user in room "SM.211" may require helicopter evacuation in an emergency. The information pane 2006 may also provide recommendations for managing user service during an emergency and/or preparing for an emergency. For example, the information pane 2006 may recommend that the user in room "SM.211" be transferred to another service unit that is closer to the helicopter landing zone. As described above, recommendations may be surfaced within the GUI 2000 in any suitable way, for example, by a visual indicator displayed within view 2002 (e.g., a flashing color, etc.).

Figure 21:
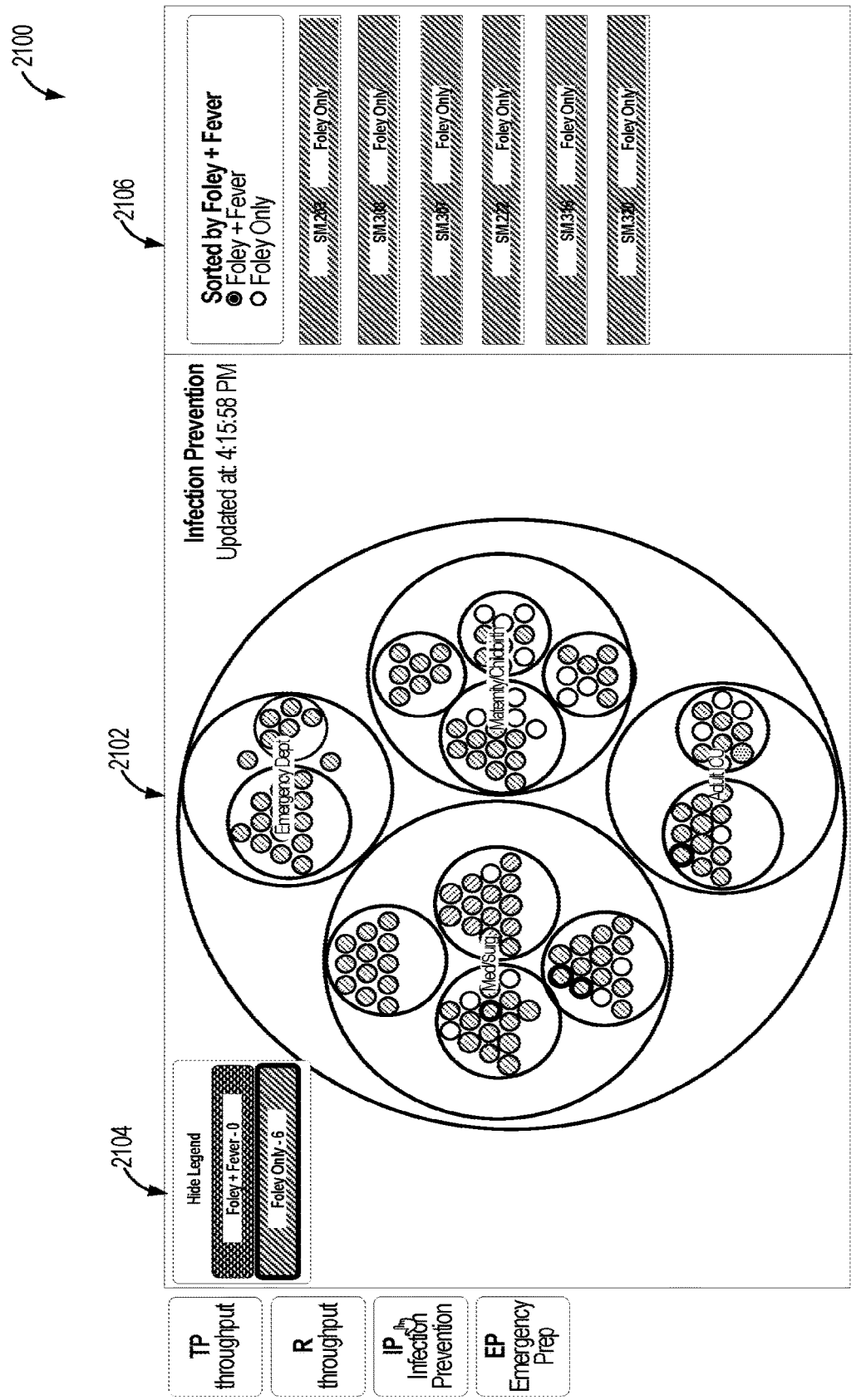
FIG. 21 illustrates another example GUI utilizable for coordinating user service based on user and/or resource classifications, according to at least one example.

FIG. 21 illustrates a GUI display 2100 of a user device that may be used to coordinate user service based at least in part on user data related to infection prevention, according to one example. The GUI 2100 may be similar to GUI 1900 of FIG. 19, including a view 2102, a legend 2104, and an information pane 2106. However, in this example, the legend 2104 identifies visual indicators that are used primarily to coordinate providing specialized service for users, especially related to infection (or illness) prevention and/or service. In some non-limiting examples, these visual indicators may correspond, respectively, to whether a user may have a Foley catheter inserted (with no fever), or may present with both a Foley catheter and a fever. Also, the information pane 2106 may indicate more details about users (or beds) depicted in the view 2102. For example, the information pane 2106 may indicate that the user in room "SM.203" only has a Foley catheter inserted, with no fever. This may correspond to a lower risk of infection (or illness), although a USP may be alerted to watch the user more closely, to mitigate against risk of infection. In another example, if the user were to also present with a fever, the SV system may an alert that the user is at a higher risk for contracting a CAUTI. Accordingly, the SV system may generate a recommendation that the user may be treated with medication to prevent infection. As described above, the recommendation may be presented in any suitable form (e.g., within view 2102 and/or information pane 2106).

Figure 22:
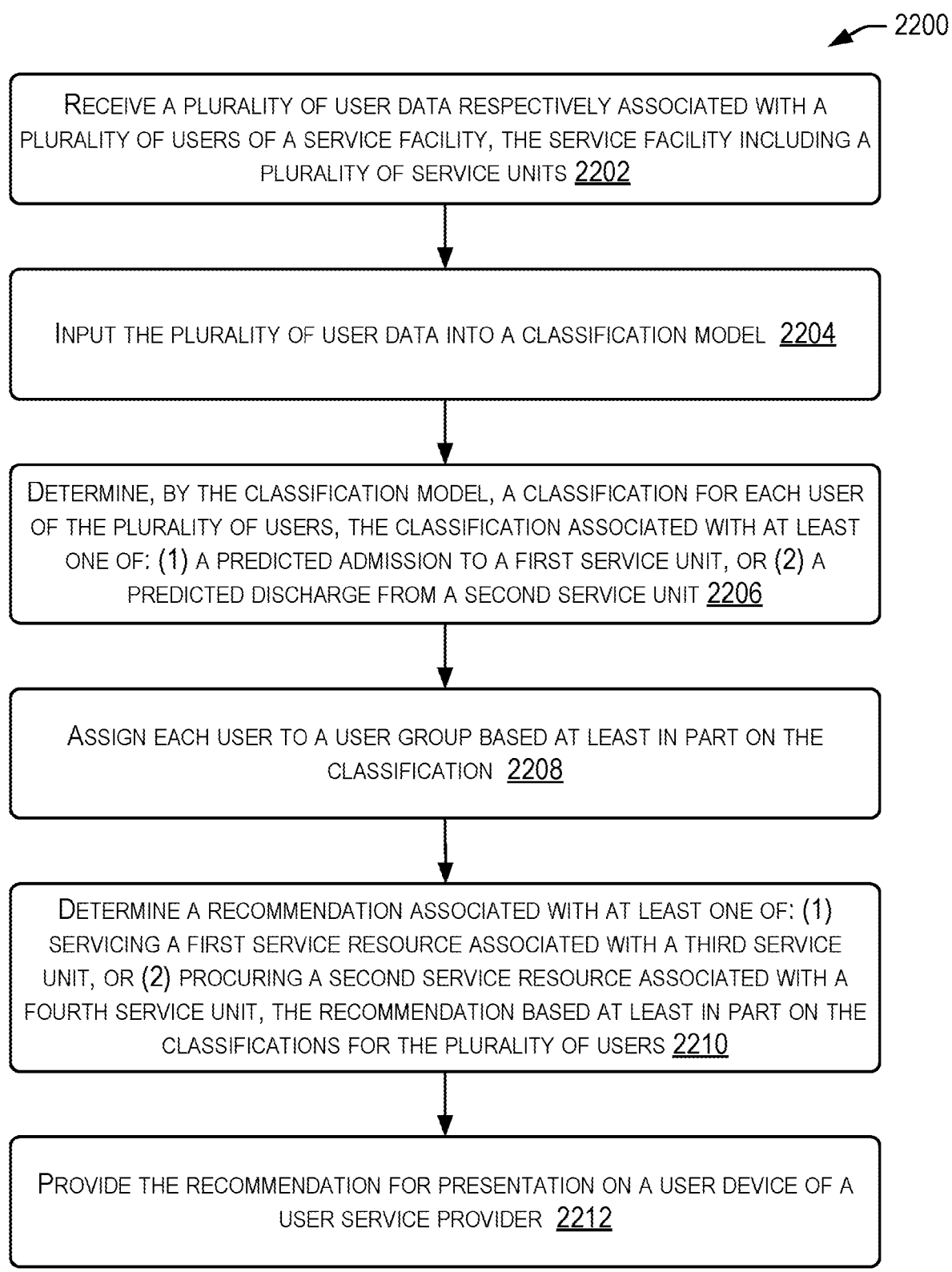
FIG. 22 illustrates a process for coordinating user service based on user and/or resource classifications, according to at least one example.

FIG. 22 illustrates an example flow diagram illustrating a process 2200 for an SV system providing recommendations for improving user throughput within a service facility, according to some examples of the present disclosure. In some examples, the recommendations may be provided within a visual representation that is presented on a user device of a USP. In some examples, the SV system that performs the process 2200 (or other processes as described in FIGS. 22-30, variations, and/or combinations thereof) may be similar to any one or more of the SV systems described herein (e.g., SV system 1211 and/or SV system 1308). Also, in some examples, the user device may correspond to user device 1336 (or 1338) of FIG. 13, and/or user device 1223 of FIG. 12.

The process 2200 may start at block 2202, whereby the SV system may receive a plurality of user data respectively associated with a plurality of users of a service facility. In some examples, the service facility may include a plurality of service units, whereby each user of the plurality of users is assigned to a service unit of the plurality of service units. In some examples, the operations of block 2202 may be similar to at least a portion of the operations described in reference to block 1202 of FIG. 12.

At block 2204, the SV system may input the plurality of user data into a classification model of the service visualization system. The classification model may be trained to output a classification for a user, and the classification may be associated with at least one of: (1) a predicted admission to a first service unit of the plurality of service units, or (2) a predicted discharge from a second service unit of the plurality of service units. In some examples, the operations of block 2204 may be similar to at least a portion of the operations described in reference to block 1204 of FIG. 12.

At block 2206, the classification model of the SV system may determine a classification for each user of the plurality of users. In some examples, the operations of block 2206 may be similar to at least a portion of the operations described in reference to block 1204 of FIG. 12.

At block 2208, the SV system may assign each user to a user group based at least in part on the classification of the respective user. In some examples, the classification may be common among members of the respective user group. In some examples, the operations of block 2208 may be similar to at least a portion of the operations described in reference to block 1204 of FIG. 12.

At block 2210, the SV system may determine a recommendation associated with at least one of: (1) servicing a first service resource (e.g., a service bed) associated with a third service unit (e.g., a branch of an ED), or (2) procuring a second service resource (e.g., a clinician, a bed) associated with a fourth service unit (e.g., which may be the same or different as the third service unit). In some examples, the recommendation may be based at least in part on the classifications and/or assigned groups for the plurality of users. In some examples, the operations of block 2210 may be similar to at least a portion of the operations described in reference to block 1206 of FIG. 12 and/or recommendation component 1322 of FIG. 13.

At block 2212, the SV system may provide the recommendation for presentation on a user device of a user service provider for use in coordinating user service among the plurality of service units of the service facility. In some examples, the recommendations may be provided within a visual representation that is presented on a user device of a USP. In some examples, the operations of block 2210 may be similar to at least a portion of the operations described in reference to block 1208 of FIG. 12. Also, in some examples, the visual representation may be similar to GUI 1400 of FIG. 14, GUI 1500 of FIG. 15, or GUI 1600 of FIG. 16.

FIG. 23 illustrates an example flow diagram illustrating a process 2300 for an SV system providing recommendations for assigning a user to a service unit, according to some examples of the present disclosure.

The process 2300 may start at block 2302, whereby the SV system may receive user data associated with a user of a plurality of users of a service facility. In some examples, the service facility may include a plurality of service units, whereby the user is assigned to a first service unit (e.g., the ED) of the plurality of service units. In some examples, the operations of block 2202 may be similar to at least a portion of the operations described in reference to block 1202 of FIG. 12.

At block 2304, the SV system may determine, by a classification model of the SV system, a classification for the user. In some examples, the classification model may be trained to output the classification based at least in part on the user data. In some examples, the classification may also be associated with a predicted future condition of the user. For example, the prediction future condition may correspond to a prediction that a severity of the user's condition is likely to increase, and will require intensive service from a clinician. In some examples, the operations of block 2304 may be similar to at least a portion of the operations described in reference to block 1204 of FIG. 12.

At block 2306, the SV system may assign the user to a user group based at least in part on the classification of the respective user. In some examples, the classification may be common with other members of the user group. In some examples, the operations of block 2306 may be similar to at least a portion of the operations described in reference to block 1204 of FIG. 12.

At block 2308, the SV system may determine, based at least in part on the classification, a recommendation associated with assigning the user to a second service unit of the plurality of service units. In some examples, the second service unit may be different from the first service unit. For example, continuing with the example above, the SV system may determine a recommendation to reassign the user from the ED to the ICU. In some examples, by transferring the user to the ICU, where they may receive more specialized service than they may otherwise receive in the Med/Surg service unit, this may increase the probability of a successful user outcome in the long-term. In another example, the SV system may determine that the user should be transferred from the ED to a behavioral health service unit for further service. However, the behavioral health service unit in the current service facility may not have clean beds (or open rooms) available for the user. The SV system may determine that an affiliated service facility (e.g., within the enterprise) does have a clean bed, and may recommend that the user be transferred to the other service facility. In some examples, this may facilitate quicker discharge for the user, rather than the user needing to wait for extended periods of time for a bed (or other resource) to become available. In some examples, the operations of block 2308 may be similar to at least a portion of the operations described in reference to block 1206 of FIG. 12.

At block 2310, the SV system may provide the recommendation for presentation on a user device of a user service provider for use in coordinating user service among the plurality of service units of the service facility. In some examples, the operations of block 2202 may be similar to at least a portion of the operations described in reference to block 1208 of FIG. 12.

FIG. 24 illustrates an example flow diagram illustrating a process 2300 for an SV system predicting bed availability within a service unit of a service facility, according to some examples of the present disclosure. In some examples, the bed availability predictions may be presented within a visual representation on a user device.

The process 2400 may start at block 2402, whereby the SV system may receive from a camera a plurality of images that identifies a bed cleaning process of a bed. In some examples, the bed cleaning process may be performed within a portion of a service unit (e.g., a room within the ED) of a service facility. In some examples, the portion of the service unit may be within a field of view of the camera. For example, the camera may be a monitoring (e.g., surveillance) camera that is mounted within the service unit and may monitor one or more beds. In some examples, the bed cleaning process may of a bed within the service unit may be performed in any suitable way. For example, an environmental services (EVS) technician may clean the bed by changing sheets, covers, etc. Upon capturing the plurality of images (e.g., a sequence of frames) that identifies the bed cleaning process, the camera may transmit the plurality of images to the SV system.

At block 2404, the SV system may input the plurality of images into a classification model of the service visualization system. In some examples, the classification model may be trained to determine a status of the bed based at least in part on identifying at least one of: (1) a recognition of the EVS technician within the portion of the service unit, (2) a movement of the EVS technician within the portion of the service unit, or (3) a duration of time that the EVS technician is detected or not detected within the portion of the service unit. For example, as described in reference to FIGS. 9-10, the classification model may be trained to perform facial recognition of EVS technician faces using a neural network. In another example, the classification model may be trained to recognize movements by the EVS technician that correspond to moving (e.g., replacing) sheets on the bed.

At block 2406, the SV system may determine, by the classification model, the status of the bed. In some examples, the status may indicate at least one of a plurality of possible bed states, including: (1) clean, (2) needs cleaning, (3) occupied, or (4) unoccupied. In some examples, the operations of block 2406 may be similar to at least a portion of the operations described in reference to block 1206 of FIG. 12.

At block 2408, the SV system may assign the bed to a bed group based at least in part on the determined status of the bed. In some examples, the determined status may be common with other beds of the service facility that are members of the bed group. In some examples, the operations of block 2408 may be similar to at least a portion of the operations described in reference to block 1206 of FIG. 12.

At block 2410, the SV system may generate a visual representation of the assigned bed group of the bed within the service unit. In some examples, the operations of block 2410 may be similar to at least a portion of the operations described in reference to block 1206 of FIG. 12.

At block 2412, the SV system may provide the visual representation to a user device of a user service provider for use in coordinating bed management among service units of the service facility. In some examples, the operations of block 2412 may be similar to at least a portion of the operations described in reference to block 1208 of FIG. 12.

FIG. 25 illustrates an example flow diagram illustrating a process 2500 for an SV system providing recommendations for assigning clinicians (e.g., nurses) to users for providing user service, according to some examples of the present disclosure.

The process 2500 may start at block 2502, whereby the SV system may receive user data associated with a user of a service unit of a service facility. In some examples, the service unit may be one of a plurality of service units of the service facility. Also, in some examples, each service unit may be associated with at least one clinician (e.g., a nurse). For example, the user may be one of a plurality of users within a room (e.g., a service unit) of an ED of the service facility. In this example, the nurse may be assigned to service for users within the room of the ED.

At block 2504, the SV system may maintain, based at least in part on the user data, at least one task associated with user service for the user and assigned to the at least one clinician. In some examples, the at least one task may be associated with a timer that corresponds to a target timeframe in which the task should be performed. For example, as described in reference to FIG. 17, the task may be associated with administering medication to the user within a predefined time interval (e.g., once per hour). It should be understood that multiple tasks (and/or timers) may be assigned to a given clinician.

At block 2506, the SV system may determine, by a prediction model of the SV system, a first risk that the at least one task will not be performed within the target timeframe. In some examples, the operations of block 2506 may be similar to as described in reference to FIG. 17.

At block 2508, the SV system may classify the service unit as a hot spot based at least in part on the first risk. For example, the SV system may determine, based on a risk threshold value, that the first risk (e.g., 86%) matches (e.g., equals or exceeds) the risk threshold value (e.g., 80%). Accordingly, the SV system may classify the service unit (and/or the associated clinician) as being a hot spot. As described herein, the hot spot may indicate that the service unit (e.g., and/or associated clinician) that may require more resources in order to accomplish the task in a timely fashion. In one example, this may be because the currently assigned nurse is overloaded with many tasks of high priority.

At block 2510, the SV system may determine a recommendation that a second clinician be assigned to the service unit. In some examples, the second clinician may be currently assigned to another service unit of the plurality of service units, whereby the other service unit is not currently classified as being a hot spot. In this way, for example, the recommendation may enabled a better balancing of resources across service units, and time-sensitive tasks may be completed on time.

At block 2512, the SV system may provide the recommendation for presentation on a user device of a user service coordinator for use in coordinating clinician assignments among the plurality of service units of the service facility. In some examples, the operations of block 2512 may be similar to at least a portion of the operations described in reference to block 1208 of FIG. 12 and/or in reference to FIG. 17.

Figure 26:
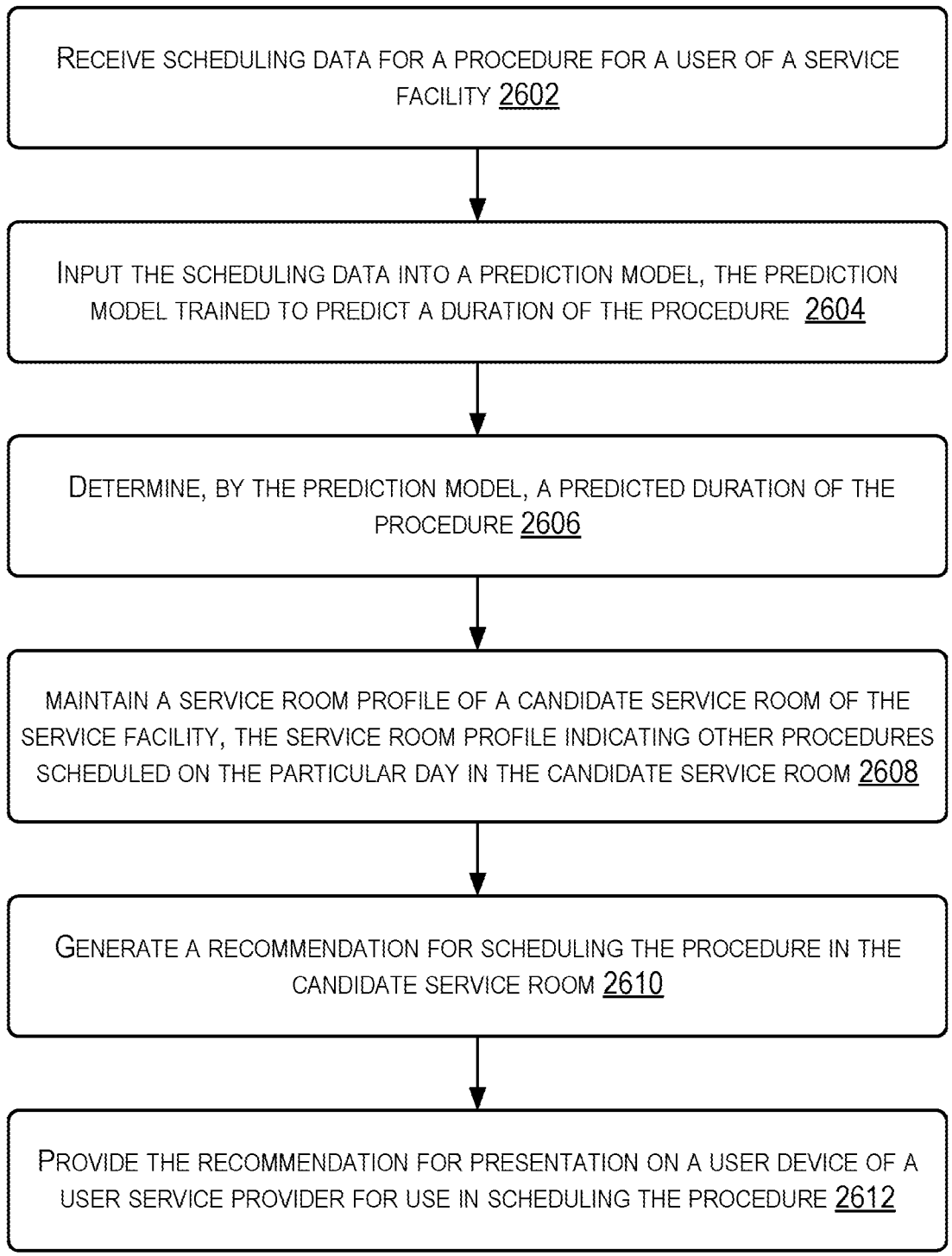
FIG. 26 illustrates another process for coordinating user service based on user and/or resource classifications, according to at least one example.

FIG. 26 illustrates an example flow diagram illustrating a process 2600 for an SV system providing recommendations for scheduling service rooms of a service facility, according to some examples of the present disclosure.

The process 2600 may start at block 2602, whereby the SV system may receive scheduling data for a procedure for a user of a service facility. In some examples, the scheduling data may indicate a clinician (e.g., a surgeon) of a plurality of clinicians of a service organization who will perform the procedure (e.g., a surgery) on a particular day. In some examples, the service facility may include a plurality of service rooms (e.g., operating rooms) and may be one of a plurality of service facilities affiliated with the service organization. Also, each service room of the plurality of service rooms may be a candidate room for performing the procedure.

At block 2604, the SV system may input the scheduling data into a prediction model of the service visualization system. In some examples, the prediction model may be trained to predict a duration of the procedure based at least in part on at least one of: (1) durations of previous procedures performed by the clinician that are substantially equivalent to the procedure, or (2) durations of previous procedures performed by other clinicians of the plurality of clinicians that are substantially equivalent to the procedure. For example, the SV system may compute a mean duration based on previous similar procedures performed by the physician, and similarly, a mean duration associated with similar procedures performed by other clinicians. The mean durations may be weighted to determine predicted time. In some cases, other data inputs may be used to predict the duration of the procedure, including, but not limited to, characteristics of the user's condition, a number of years of practice of the physician, etc.

At block 2606, the SV system may determine, by the prediction model, a predicted duration of the procedure.

At block 2608, the SV system may maintain a service room profile of a candidate service room of the service facility. The service room profile may indicate other procedures scheduled on the particular day in the candidate service room. It should be understood that the SV system may maintain the service room profile even before beginning the process 2600. In some examples, details of each procedure scheduled for the service room may also be stored in association with the profile. For example, as depicted in FIG. 18, the room profile may include information corresponding to a procedure type, the surgeon's name, the user's name, a room identifier (e.g., a room number), scheduled start and end times of the procedure, a projected duration, a confidence level in the projected duration, etc.

At block 2610, the SV system may generate a recommendation for scheduling the procedure in the candidate service room. In some examples, the recommendation may include at least one of: (1) a room identifier for the candidate service room, (2) a start time, or (3) a time duration of the procedure, the recommendation based at least in part on at least one of the service room profile and the predicted duration. In some examples, the operations of block 2610 may be similar to as described in reference to FIG. 18.

At block 2612, the SV system may provide the recommendation for presentation on a user device of a user service provider for use in scheduling the procedure. In some examples, the operations of block 2612 may be similar to as described in reference to FIG. 18 (e.g., GUI 1800).

Figure 27:
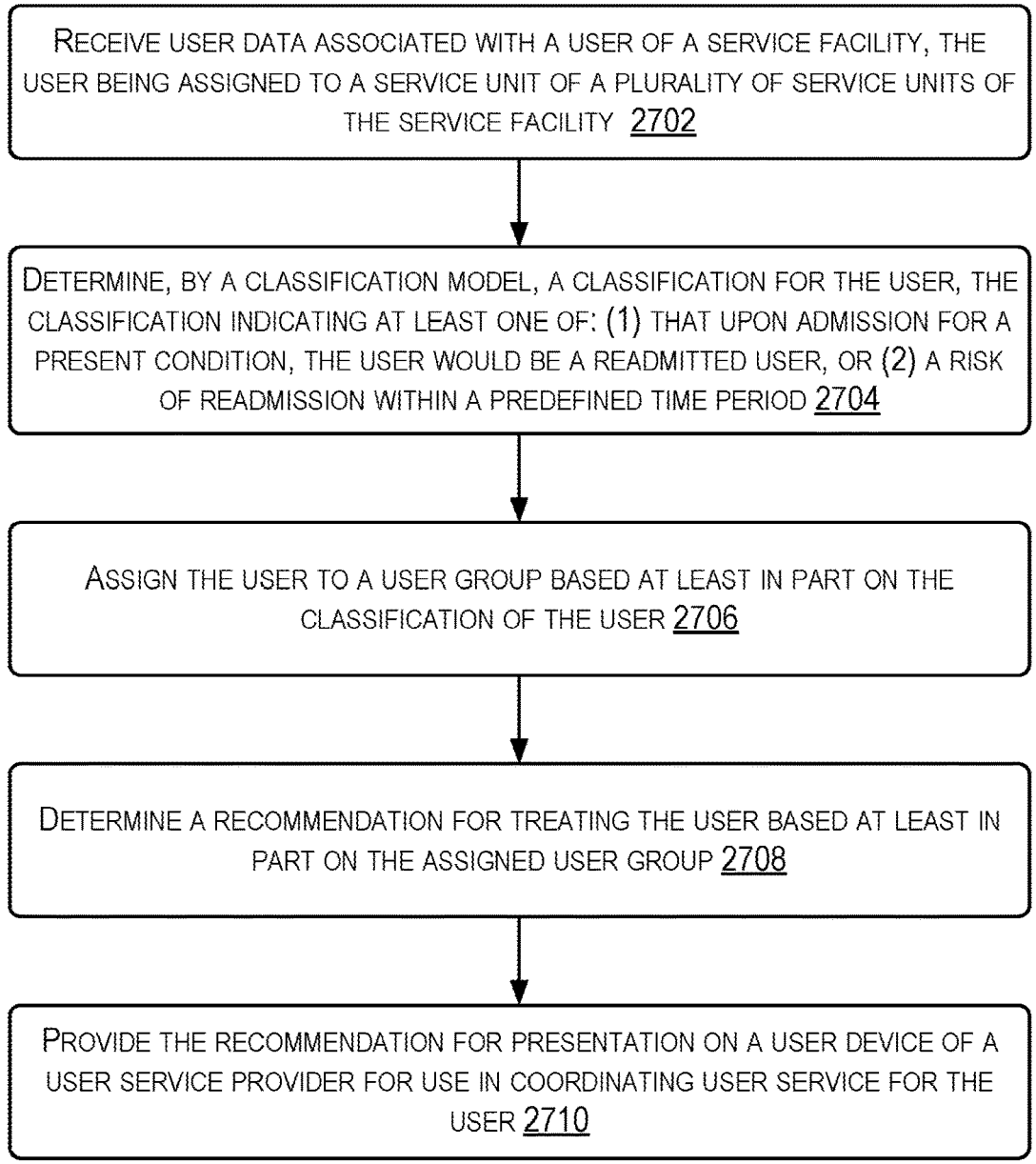
FIG. 27 illustrates another process for coordinating user service based on user and/or resource classifications, according to at least one example.

FIG. 27 illustrates an example flow diagram illustrating a process 2700 for an SV system providing recommendations for coordinating user service based on user readmission prediction data, according to some examples of the present disclosure.

The process 2700 may start at block 2702, whereby the SV system may receive user data associated with a user of a service facility. In some examples, the user may be assigned to a service unit of a plurality of service units of the service facility. In some examples, the operations of block 2702 may be similar to at least a portion of the operations described in reference to block 1202 of FIG. 12.

At block 2704, the SV system may determine, by a classification model of the SV system, a classification for the user. In some examples, the classification model may be trained to output the classification based at least in part on the user data. In some examples, the classification may indicate at least one of: (1) that upon admission for a present condition, the user would be a readmitted user, or (2) a risk of readmission within a predefined time period following a discharge of the user from the service facility. In the first case, the SV system may maintain data associated with previous visits by the user to the service facility. Accordingly, the SV system may determine that, if the user were to be admitted (e.g., as an inpatient) for the present condition, that would constitute a readmission. In the second case, the SV system may use a prediction model (e.g., as described in reference to FIGS. 9-10) to predict a likelihood that the user will be readmitted. In some examples, the prediction may indicate that the user is likely to be readmitted within a certain time interval.

At block 2706, the SV system may assign the user to a user group based at least in part on the classification of the user, the classification being common with members of the user group. In some examples, the operations of block 2706 may be similar to at least a portion of the operations described in reference to block 1204 of FIG. 12.

At block 2708, the SV system may determine a recommendation for treating the user based at least in part on the assigned user group. In some examples, the operations of block 2708 may be similar to as described in reference to FIG. 19.

At block 2710, the SV system may provide the recommendation for presentation on a user device of a user service provider for use in coordinating user service for the user. In some examples, the presentation may indicate the assigned user group of the user within the assigned service unit. In some examples, the operations of block 2710 may be similar to as described in reference to FIG. 19.

FIG. 28 illustrates an example flow diagram illustrating a process 2800 for an SV system providing recommendations for coordinating user service based on user data related to emergency preparedness, according to some examples of the present disclosure.

The process 2800 may start at block 2802, whereby the SV system may receive user data associated with a user of a service facility. In some examples, the user may be assigned to a service unit of a plurality of service units of the service facility. In some examples, the operations of block 2802 may be similar to at least a portion of the operations described in reference to block 1202 of FIG. 12.

At block 2804, the SV system may determine, by a classification model of the service visualization system, a classification for the user based at least in part on the user data. In some examples, the classification may be associated with a condition or service status of the user for which specialized service for the user is beneficial during an emergency event. For example, the user may be disabled or otherwise immobilized. In another example, the user may be connected to an IV drip to receive service, and may require assistance if needed to be transported during an emergency event (e.g., a natural disaster).

At block 2806, the SV system may assign the user to a user group based at least in part on the classification of the user. In some examples, the classification may be common with members of the user group. In some examples, the operations of block 2806 may be similar to at least a portion of the operations described in reference to block 1204 of FIG. 12.

At block 2808, the SV system may determine a recommendation for providing the specialized service for the user based at least in part on the assigned user group. In some examples, the specialized service may be associated with at least one of: (1) a resource to be used for treating the user during the emergency event, (2) a navigation path suitable for evacuating the user, or (3) assigning the user to a second service unit of the plurality of service units based at least in part on the suitable navigation path. For example, a helicopter or ambulance may be recommended for use in transporting the user during an emergency event. In another example, the SV system may recommend that the user be moved to another service unit that is near a suitable location for evacuating the user. In another example, the recommended navigation path may include instructions and/or procedural steps for evacuating the user. For example, the user may first be taken to a location where they are fitted with equipment suitable for being transporting the user during an evacuation.

At block 2810, the SV system may provide the recommendation for presentation on a user device of a user service provider for use in coordinating user service for the user during the emergency event. In some examples, the operations of block 2810 may be similar to as described in reference to FIG. 20.

FIG. 29 illustrates an example flow diagram illustrating a process 2900 for an SV system providing recommendations for coordinating user service based on one or more service triggers, according to some examples of the present disclosure.

The process 2900 may start at block 2902, whereby the SV system may receive user data associated with a user of a service facility. In some examples, the user may be assigned to a service unit of a plurality of service units of the service facility. In some examples, the operations of block 2902 may be similar to at least a portion of the operations described in reference to block 1202 of FIG. 12.

At block 2904, the SV system may detect an occurrence of a service trigger of a plurality of service triggers based at least in part on the user data. In some examples, the plurality of service triggers may be respectively associated with one or more infection (or illness) risk indicators. The service trigger may correspond to a rule (or mechanism) that is activated when one or more conditions are met. For example, as described above, a trigger may correspond to a rule that activates upon detecting that a user has a Foley catheter inserted. Another trigger be associated with the user presenting with a fever. In some examples, the one or more conditions may respectively correspond to indicators of infection risk (or any other user condition that is being monitored, such as cancer, cardiac toxicity, etc.).

At block 2906, the SV system may determine, by a classification model of the service visualization system, a classification for the user based at least in part on the occurrence of the service trigger. In some examples, the operations of block 2906 may be similar to at least a portion of the operations described in reference to block 1204 of FIG. 12. For example, a prediction model of the SV system may classify the user as being at high risk of having (or acquiring) an infection (e.g., a CAUTI) based on the occurrence of the service trigger.

At block 2908, the SV system may assign the user to a user group based at least in part on the classification of the user, the classification being common with members of the user group. In some examples, the operations of block 2908 may be similar to at least a portion of the operations described in reference to block 1204 of FIG. 12.

At block 2910, the SV system may determine a recommendation for treating the user based at least in part on the assigned user group. In some examples, the recommendation may be associated with at least one of: (1) a priority for treating the user, (2) a specialized service for the user (e.g., a particular antibiotics), or (3) assigning the user to a second service unit of the plurality of service units based at least in part on the specialized service (e.g., to isolate the user from other users and thereby reduce the risk of infection).

At block 2912, the SV system may provide the recommendation for presentation on a user device of a user service provider for use in coordinating user service for the user. In some examples, the operations of block 2912 may be similar to at least a portion of the operations described in reference to block 1208 of FIG. 12 and/or FIG. 21.

Figure 30:
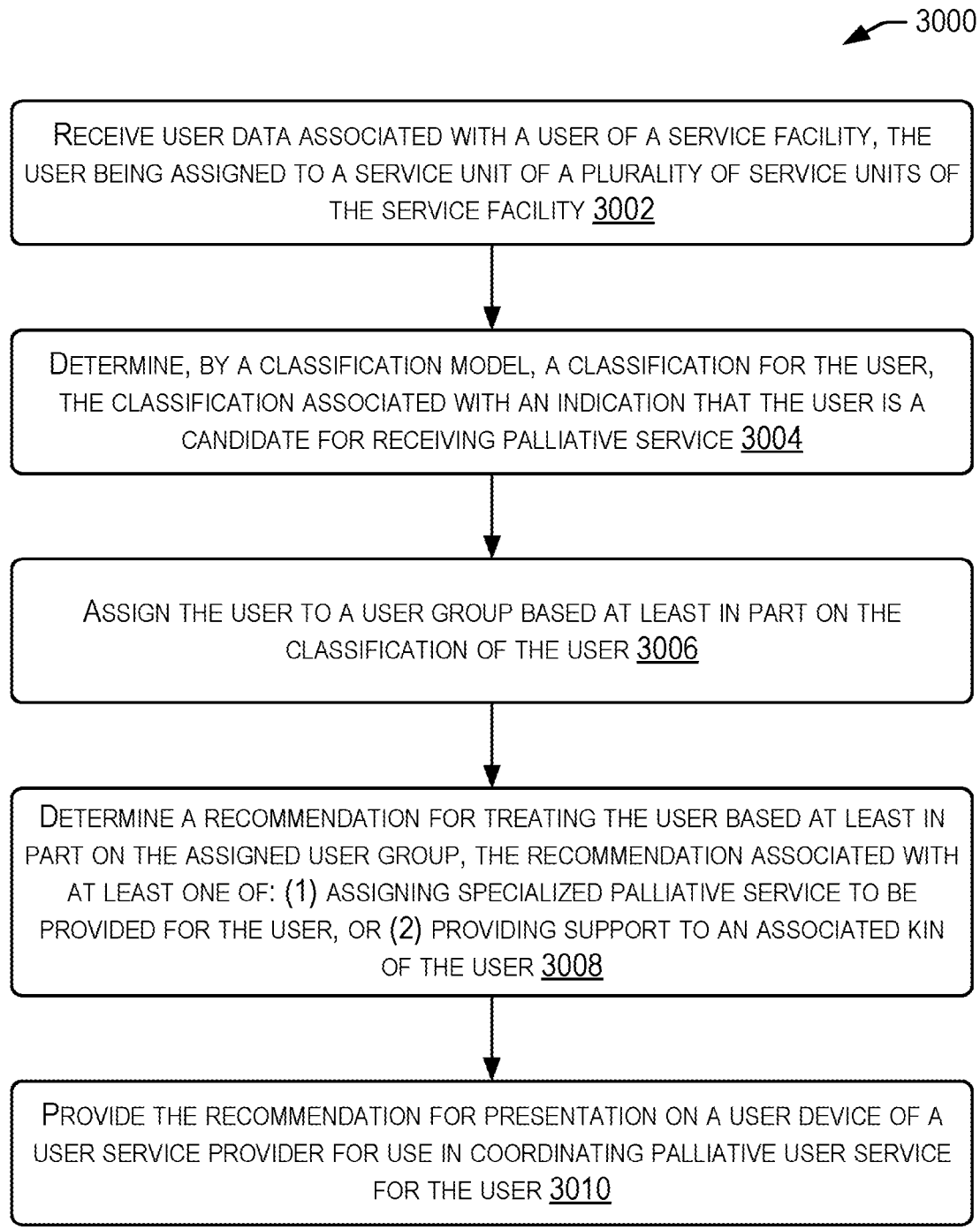
FIG. 30 illustrates another process for coordinating user service based on user and/or resource classifications, according to at least one example.

FIG. 30 illustrates an example flow diagram illustrating a process 3000 for an SV system providing recommendations for coordinating palliative service for a user based on user data, according to some examples of the present disclosure.

The process 3000 may start at block 3002, whereby the SV system may receive user data associated with a user of a service facility. In some examples, the user may be assigned to a service unit of a plurality of service units of the service facility. In some examples, the user data may include characteristics of the user, for example, a user's age, a severity of the user's condition, a likelihood of recovery, etc. In some examples, the operations of block 3002 may be similar to at least a portion of the operations described in reference to block 1202 of FIG. 12.

At block 3004, the SV system may determine, by a classification model of the SV system, a classification for the user. In some examples, the classification model may be trained to output the classification based at least in part on the user data. In some examples, the classification may be associated with an indication that the user is a candidate for receiving palliative service. In some examples, the operations of block 3004 may be similar to at least a portion of the operations described in reference to block 1204 of FIG. 12.

At block 3006, the SV system may assign the user to a user group based at least in part on the classification of the user, the classification being common with members of the user group. In some examples, the operations of block 3006 may be similar to at least a portion of the operations described in reference to block 1204 of FIG. 12.

At block 3008, the SV system may determine a recommendation for treating the user based at least in part on the assigned user group. In some examples, the recommendation may be associated with at least one of: (1) assigning specialized palliative service to be provided for the user, or (2) providing support to an associated kin of the user (e.g., one or more family members, close friends, etc.). For example, the recommendation may include instructions for connecting the user with a specialist that may offer counseling for the user or quality-of-life enhancement measures. The specialist may also provide support to associated kin of the user as they participate in the user journey alongside the user. In some examples, the operations of block 3008 may be similar to at least a portion of the operations described in reference to block 1206 of FIG. 12.

At block 3010, the SV system may provide the recommendation for presentation on a user device of a user service provider for use in coordinating palliative user service for the user. In some examples, the operations of block 3010 may be similar to at least a portion of the operations described in reference to block 1208 of FIG. 12.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method, comprising:
   receiving, by a service visualization system, a plurality of patient data respectively associated with a plurality of patients of a service facility, the service facility including a plurality of service units, each patient of the plurality of patients assigned to a service unit of the plurality of service units;
   inputting, by the service visualization system, the plurality of patient data into a classification model of the service visualization system, the classification model trained to output a classification for a patient, the classification being associated with at least one of: (1) a predicted admission to a first service unit of the plurality of service units, or (2) a predicted discharge from a second service unit of the plurality of service units;
   determining, by the classification model, a classification for each patient of the plurality of patients;
   assigning, by the service visualization system, each respective patient to a respective patient group based at least in part on the classification of the respective patient, the classification being common with members of the respective patient group;
   determining, by the service visualization system, a recommendation associated with at least one of: (1) servicing a first service resource associated with a third service unit, or (2) procuring a second service resource associated with a fourth service unit, the recommendation based at least in part on the classifications for the plurality of patients; and
   providing, by the service visualization system, the recommendation for presentation on a user device of a patient care provider for use in coordinating patient care among the plurality of service units of the service facility.

2. The computer-implemented method of claim 1, wherein the classification of each patient of the plurality of patients is based at least in part on a predicted future condition of each patient.

3. The computer-implemented method of claim 1, wherein the first service resource or the second service resource corresponds to a bed, the first service resource or the second service resource being one of a plurality of service resources associated with the third service unit or the fourth service unit, and wherein a resource status data indicates whether the service resource is at least one of: (I) clean, (II) needs cleaning, (III) occupied, or (IV) unoccupied.

4. The computer-implemented method of claim 1, wherein the presentation of the recommendation on the user device includes a visual indicator associated with the recommendation.

5. The computer-implemented method of claim 1, wherein servicing the first service resource associated with the third service unit comprises:
   scheduling a cleaning of the first service resource, following a discharge of a particular patient from the third service unit.

6. The computer-implemented method of claim 1, wherein procuring the second service resource associated with the fourth service unit comprises:
   transferring a particular patient from a current service resource associated with a current service unit to the second service resource associated with the fourth service unit.

7. The computer-implemented method of claim 6, wherein the current service unit is associated with a first service facility and the fourth service unit is associated with a second service facility, wherein the first service facility and the second service facility are separate facilities.

8. A service visualization system, comprising:
   a memory configured to store computer-executable instructions; and
   a processor configured to access the memory and execute the computer-executable instructions to at least:
      receive a plurality of patient data respectively associated with a plurality of patients of a service facility, the service facility including a plurality of service units, each patient of the plurality of patients assigned to a service unit of the plurality of service units;
      input the plurality of patient data into a classification model of the service visualization system, the classification model trained to output a classification for a patient, the classification being associated with at least one of: (1) a predicted admission to a first service unit of the plurality of service units, or (2) a predicted discharge from a second service unit of the plurality of service units;
      determine, by the classification model, a classification for each patient of the plurality of patients;
      assign each respective patient to a respective patient group based at least in part on the classification of the respective patient, the classification being common with members of the respective patient group;
      determine a recommendation associated with at least one of: (1) servicing a first service resource associated with a third service unit, or (2) procuring a second service resource associated with a fourth service unit, the recommendation based at least in part on the classifications for the plurality of patients; and
      provide the recommendation for presentation on a user device of a patient care provider for use in coordinating patient care among the plurality of service units of the service facility.

9. The service visualization system of claim 8, wherein the classification of each patient of the plurality of patients is based at least in part on a predicted future condition of each patient.

10. The service visualization system of claim 8, wherein the first service resource or the second service resource correspond to a bed, the first service resource or the second service resource being one of a plurality of service resources associated with the third service unit or the fourth service unit, and wherein a resource status data indicates whether the service resource is at least one of: (I) clean, (II) needs cleaning, (III) occupied, or (IV) unoccupied.

11. The service visualization system of claim 8, wherein the presentation of the recommendation on the user device includes a visual indicator associated with the recommendation.

12. The service visualization system of claim 8, wherein servicing the first service resource associated with the third service unit comprises:
  scheduling a cleaning of the first service resource, following a discharge of a particular patient from the third service unit.

13. The service visualization system of claim 8, wherein procuring the second service resource associated with a fourth service unit comprises:
  transferring a particular patient from a current service resource associated with a current service unit to the second service resource associated with the fourth service unit.

14. The service visualization system of claim 13, wherein the current service unit is associated with a first service facility and the fourth service unit is associated with a second service facility, wherein the first service facility and the second service facility are separate facilities.

15. One or more non-transitory computer-readable storage devices comprising computer-executable instructions that, when executed by one or more computer systems of a service visualization system, cause the one or more computer systems to perform operations, comprising:
  receiving a plurality of patient data respectively associated with a plurality of patients of a service facility, the service facility including a plurality of service units, each patient of the plurality of patients assigned to a service unit of the plurality of service units;
  inputting the plurality of patient data into a classification model of the service visualization system, the classification model trained to output a classification for a patient, the classification being associated with at least one of: (1) a predicted admission to a first service unit of the plurality of service units, or (2) a predicted discharge from a second service unit of the plurality of service units;
  determining, by the classification model, a classification for each patient of the plurality of patients;
  assigning each respective patient to a respective patient group based at least in part on the classification of the respective patient, the classification being common with members of the respective patient group;
  determining a recommendation associated with at least one of: (1) servicing a first service resource associated with a third service unit, or (2) procuring a second service resource associated with a fourth service unit, the recommendation based at least in part on the classifications for the plurality of patients; and
  providing the recommendation for presentation on a user device of a patient care provider for use in coordinating patient care among the plurality of service units of the service facility.

16. The one or more non-transitory computer-readable storage devices of claim 15, wherein the classification of each patient of the plurality of patients is based at least in part on a predicted future condition of each patient.

17. The one or more non-transitory computer-readable storage devices of claim 15, wherein the first service resource or the second service resource correspond to a bed, the first service resource or the second service resource being one of a plurality of service resources associated with the third service unit or the fourth service unit, and wherein a resource status data indicates whether the service resource is at least one of: (I) clean, (II) needs cleaning, (III) occupied, or (IV) unoccupied.

18. The one or more non-transitory computer-readable storage devices of claim 15, wherein the presentation of the recommendation on the user device includes a visual indicator associated with the recommendation.

19. The one or more non-transitory computer-readable storage devices of claim 15, wherein servicing the first service resource associated with the third service unit comprises:
  scheduling a cleaning of the first service resource, following a discharge of a particular patient from the third service unit.

20. The one or more non-transitory computer-readable storage devices of claim 15, wherein procuring the second service resource associated with the fourth service unit comprises:
  transferring a particular patient from a current service resource associated with a current service unit to the second service resource associated with the fourth service unit.

* * * * *